(12) United States Patent
Jaeger et al.

(10) Patent No.: US 11,154,734 B2
(45) Date of Patent: Oct. 26, 2021

(54) GAS DELIVERY SYSTEM

(71) Applicant: RainMaker Solutions, Inc., El Segundo, CA (US)

(72) Inventors: Eduard Albert Jaeger, El Segundo, CA (US); Robert Gregory Stahl, Culver City, CA (US); Jacob Timm Bowles, El Segundo, CA (US)

(73) Assignee: RainMaker Solutions, Inc., El Segundo, CA (US)

( * ) Notice: Subject to any disclaimer, the term of this patent is extended or adjusted under 35 U.S.C. 154(b) by 237 days.

(21) Appl. No.: 15/817,083

(22) Filed: Nov. 17, 2017

(65) Prior Publication Data

US 2018/0193677 A1 Jul. 12, 2018

Related U.S. Application Data

(63) Continuation of application No. 15/813,157, filed on Nov. 15, 2017, now abandoned.
(Continued)

(51) Int. Cl.
*F16L 37/00* (2006.01)
*F16L 37/56* (2006.01)
(Continued)

(52) U.S. Cl.
CPC .............. *A62B 18/086* (2013.01); *A42B 1/24* (2013.01); *A42B 3/0406* (2013.01); *A42B 3/048* (2013.01);
(Continued)

(58) Field of Classification Search
CPC ......... A42B 1/24; A42B 3/048; A42B 18/086; A42B 3/28; A42B 3/286; A42B 3/283;
(Continued)

(56) References Cited

U.S. PATENT DOCUMENTS 2,453,813 A * 11/1948 Warren ................... F16L 19/05
285/89
2,793,057 A * 5/1957 McGugin .............. F16L 37/004
285/9.1
(Continued)

FOREIGN PATENT DOCUMENTS

| WO | 2008129514 A2 | 10/2008 |
|---|---|---|
| WO | 2018007966 A1 | 1/2018 |
| WO | 2018017545 A1 | 1/2018 |

OTHER PUBLICATIONS

International Searching Authority, Patent Cooperation Treaty, PCT, Notification Of Transmittal Of The International Search Report And The Written Opinion Of The International Searching Authority, Or The Declaration, dated Mar. 8, 2018; International Application No. PCT/US17/62287, International Filing Date, Nov. 17, 2017 (Nov. 17, 2017); Applicant, Rainmaker Solutions, Inc.; p. 1-1.
(Continued)

*Primary Examiner* — Justin M Larson
(74) *Attorney, Agent, or Firm* — Hackler Daghighian Martino & Novak

(57) ABSTRACT

A magnetic quick connect for a fluid delivery system includes a male coupling member and a female coupling member. The male coupling member defines a first outer fluid communication path and includes a first magnetic material. A first inner member is disposed within the first outer fluid communication path and defines a first inner communication path. The female coupling member defines a second outer fluid communication path and includes a second magnetic material. A second inner member is disposed within the second outer fluid communication path and defines a second inner communication path. The male and female coupling members are detachably held together by an attractive force between the first and second magnetic materials such that the first and second outer communication
(Continued)

paths are held in fluid communication, and the first and second inner communication paths are held in fluid communication.

5 Claims, 31 Drawing Sheets

Related U.S. Application Data

(60) Provisional application No. 62/423,430, filed on Nov. 17, 2016.

(51) Int. Cl.

| | |
|---|---|
| *A42B 3/28* | (2006.01) |
| *A42B 3/04* | (2006.01) |
| *A62B 18/08* | (2006.01) |
| *A62B 18/10* | (2006.01) |
| *A42B 1/24* | (2021.01) |
| *A62B 18/04* | (2006.01) |
| *F16L 55/00* | (2006.01) |
| *A42B 3/06* | (2006.01) |
| *A62B 9/04* | (2006.01) |
| *F16L 55/115* | (2006.01) |
| *F16L 39/00* | (2006.01) |
| *A61F 9/06* | (2006.01) |
| *A62B 18/00* | (2006.01) |
| *F16L 41/02* | (2006.01) |

(52) U.S. Cl.
CPC ............... *A42B 3/06* (2013.01); *A42B 3/283* (2013.01); *A42B 3/285* (2013.01); *A42B 3/286* (2013.01); *A62B 18/04* (2013.01); *A62B 18/08* (2013.01); *A62B 18/10* (2013.01); *F16L 37/004* (2013.01); *F16L 55/00* (2013.01); *A61F 9/068* (2013.01); *A62B 9/04* (2013.01); *A62B 18/006* (2013.01); *A62B 18/045* (2013.01); *F16L 37/565* (2013.01); *F16L 39/005* (2013.01); *F16L 41/021* (2013.01); *F16L 55/115* (2013.01); *F16L 2201/80* (2013.01)

(58) Field of Classification Search
CPC ..... F16L 37/004; F16L 2201/80; F16L 37/00; F16L 37/005; F16L 39/005; F16L 37/56; F16L 37/565; A62B 18/04; A62B 18/045; A62B 18/08; A62B 18/086
USPC .......................... 224/181, 183, 148.2; 285/9.1
See application file for complete search history.

(56) References Cited

U.S. PATENT DOCUMENTS

| | | | |
|---|---|---|---|
| 2,802,592 A | 8/1957 | Clifton | |
| 2,879,343 A * | 3/1959 | Finken | H04M 1/05 379/430 |
| 3,181,895 A * | 5/1965 | Cator | F16L 37/004 285/1 |
| 3,211,178 A | 10/1965 | Kiszko | |
| 3,586,048 A | 6/1971 | Arnold | |
| 4,300,597 A | 11/1981 | Delay, Sr. | |
| 4,304,415 A | 12/1981 | Wolf et al. | |
| 4,362,327 A * | 12/1982 | Mieth | F16L 23/024 285/332.3 |
| 4,491,088 A * | 1/1985 | Hostetler | A01K 39/0213 119/72.5 |
| 4,502,480 A | 3/1985 | Yamamoto | |
| 4,549,541 A * | 10/1985 | Sundahl | A42B 3/08 128/201.19 |
| 4,706,834 A | 11/1987 | Farney | |
| 4,763,683 A * | 8/1988 | Carmack | F16L 37/32 137/594 |
| 5,060,833 A * | 10/1991 | Edison | A45F 3/16 215/388 |
| 5,085,349 A * | 2/1992 | Fawcett | A45F 3/20 220/703 |
| 5,355,961 A * | 10/1994 | Gariepy | E21B 33/04 166/387 |
| 5,401,064 A | 3/1995 | Guest | |
| 5,482,297 A * | 1/1996 | Burns | F16J 15/062 277/644 |
| 5,571,260 A * | 11/1996 | Krug | A45F 3/16 222/175 |
| 5,727,714 A * | 3/1998 | Fawcett | A45F 3/16 222/175 |
| 5,984,145 A * | 11/1999 | McAllister | A45F 3/16 222/175 |
| 6,070,767 A * | 6/2000 | Gardner | A45F 3/16 220/703 |
| 6,192,934 B1 | 2/2001 | Coates, III et al. | |
| 6,283,344 B1 * | 9/2001 | Bradley | A42B 1/24 222/175 |
| 6,523,833 B1 * | 2/2003 | Ishigaki | F16J 15/025 277/549 |
| 6,758,213 B1 * | 7/2004 | Brekken | B63C 11/02 128/202.15 |
| 6,997,181 B2 | 2/2006 | Fletcher | |
| 7,073,688 B2 * | 7/2006 | Choi | A45F 3/20 141/379 |
| 7,130,439 B2 * | 10/2006 | Chen | A62B 23/02 381/376 |
| 7,252,112 B1 * | 8/2007 | Imler | F16L 37/004 137/614.04 |
| 7,490,740 B2 * | 2/2009 | Robins | A45F 3/20 222/175 |
| 7,793,987 B1 * | 9/2010 | Busch | A61M 16/0816 285/9.1 |
| 8,079,600 B2 * | 12/2011 | Shojima | F16J 15/062 277/644 |
| 8,181,972 B2 * | 5/2012 | Tsuji | F16K 51/02 277/644 |
| 8,210,572 B2 | 7/2012 | Davis | |
| 8,770,190 B2 * | 7/2014 | Doherty | A61M 16/021 128/202.27 |
| 8,973,173 B2 | 3/2015 | Elam et al. | |
| 9,140,393 B2 * | 9/2015 | Wolff | F16L 37/004 |
| 9,243,734 B2 * | 1/2016 | Aubert | B08B 15/002 |
| 9,322,498 B2 | 4/2016 | Wolff et al. | |
| 9,402,119 B2 * | 7/2016 | Contreras Hernandezs | A62B 18/08 |
| 9,440,248 B2 * | 9/2016 | Pouliaude | B05B 11/0008 |
| 9,803,787 B2 * | 10/2017 | Scott | F16L 37/004 |
| 10,016,569 B2 | 7/2018 | Flower et al. | |
| 10,125,753 B2 | 11/2018 | Poertner | |
| 10,179,726 B2 * | 1/2019 | Steele | B67D 1/1243 |
| 10,357,073 B1 * | 7/2019 | Stahl | A42B 3/048 |
| 10,492,552 B2 * | 12/2019 | Jaeger | H04R 1/04 |
| 10,969,046 B2 * | 4/2021 | Leidefeldt | B62D 33/067 |
| 2003/0154983 A1 | 8/2003 | Marx | |
| 2003/0209861 A1 * | 11/2003 | Keene | E21B 33/1212 277/603 |
| 2005/0238193 A1 * | 10/2005 | Chen | A62B 23/02 381/376 |
| 2005/0241641 A1 * | 11/2005 | Fletcher | A62B 18/086 128/205.22 |
| 2006/0180154 A1 * | 8/2006 | Stone | A42B 3/048 128/207.11 |
| 2007/0241560 A1 | 10/2007 | Malone | |
| 2008/0029972 A1 * | 2/2008 | Smathers | F16J 15/062 277/641 |
| 2008/0143098 A1 * | 6/2008 | Zimmermann | H01M 8/04201 285/9.1 |
| 2009/0146412 A1 * | 6/2009 | Schoenoff | F16L 37/004 285/9.1 |
| 2009/0160137 A1 * | 6/2009 | Smathers | F16J 15/062 277/642 |

(56) References Cited

U.S. PATENT DOCUMENTS

| | | | | |
|---|---|---|---|---|
| 2010/0066082 A1* | 3/2010 | Aubert | ............... | F01N 13/1805 285/408 |
| 2010/0307497 A1 | 12/2010 | Busch et al. | | |
| 2010/0322826 A1* | 12/2010 | Locascio | ............. | B01J 19/0093 422/537 |
| 2011/0042485 A1* | 2/2011 | McNulty | .............. | B05B 15/628 239/203 |
| 2011/0084474 A1* | 4/2011 | Paden | .................. | F16L 37/004 285/9.1 |
| 2011/0204622 A1 | 8/2011 | Lewis et al. | | |
| 2012/0013117 A1* | 1/2012 | Bernshtein | ........... | F16L 37/004 285/9.1 |
| 2012/0246809 A1* | 10/2012 | Elam | ..................... | A42B 3/048 2/424 |
| 2014/0318650 A1* | 10/2014 | Wolff | ................... | F16L 37/004 137/614.02 |
| 2015/0059445 A1* | 3/2015 | Tragsdorf | ............. | B65D 43/22 73/49.2 |
| 2015/0250972 A1 | 9/2015 | Haibach et al. | | |
| 2017/0370513 A1 | 12/2017 | Waugh et al. | | |
| 2018/0035787 A1* | 2/2018 | Jaeger | .................. | B67D 1/0888 |
| 2018/0192724 A1* | 7/2018 | Jaeger | .................... | H04R 1/083 |
| 2018/0193676 A1* | 7/2018 | Jaeger | .................... | A42B 3/285 |
| 2018/0195654 A1* | 7/2018 | Jaeger | .................... | A42B 3/048 |
| 2020/0116284 A1* | 4/2020 | Ashida | ................. | F16L 37/004 |
| 2020/0352270 A1* | 11/2020 | Stahl | ...................... | A42B 1/245 |
| 2020/0386354 A1* | 12/2020 | Zoe | ......................... | F16G 11/10 |

OTHER PUBLICATIONS

International Searching Authority, Patent Cooperation Treaty, PCT, International Search Report (PCT Article 18 and Rules 43 and 44), dated Mar. 8, 2018, International Application No. PCT/US17/62287, International Filing Date, Nov. 17, 2017 (Nov. 17, 2017); pp. 1-2.

International Searching Authority, Patent Cooperation Treaty, PCT, Written Opinion Of The International Searching Authority (PCT Rule 43 bis.1), dated Mar. 8, 2018, International Application No. PCT/US17/62287, International Filing Date, Nov. 17, 2017 (Nov. 17, 2017); pp. 1-6.

* cited by examiner

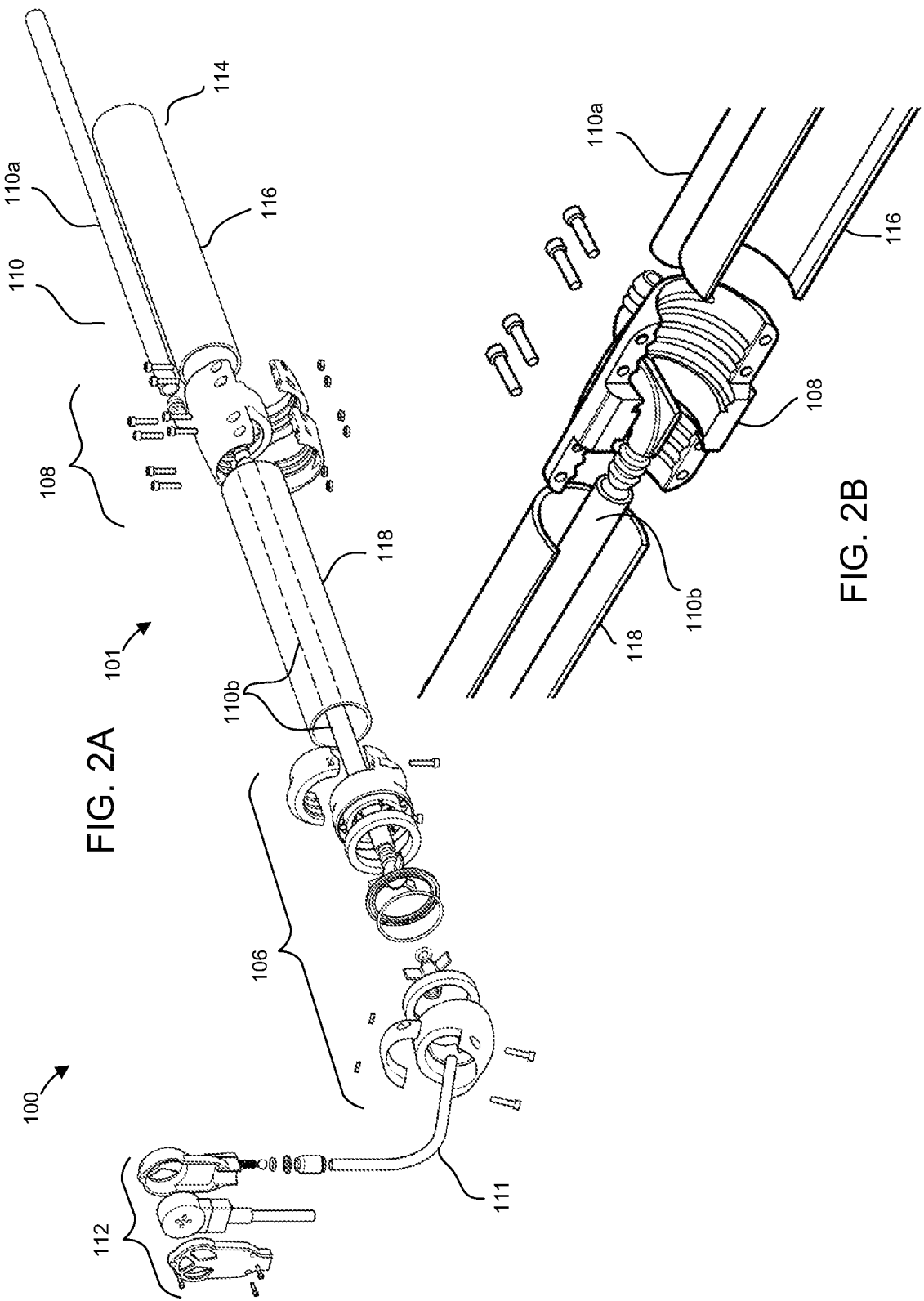

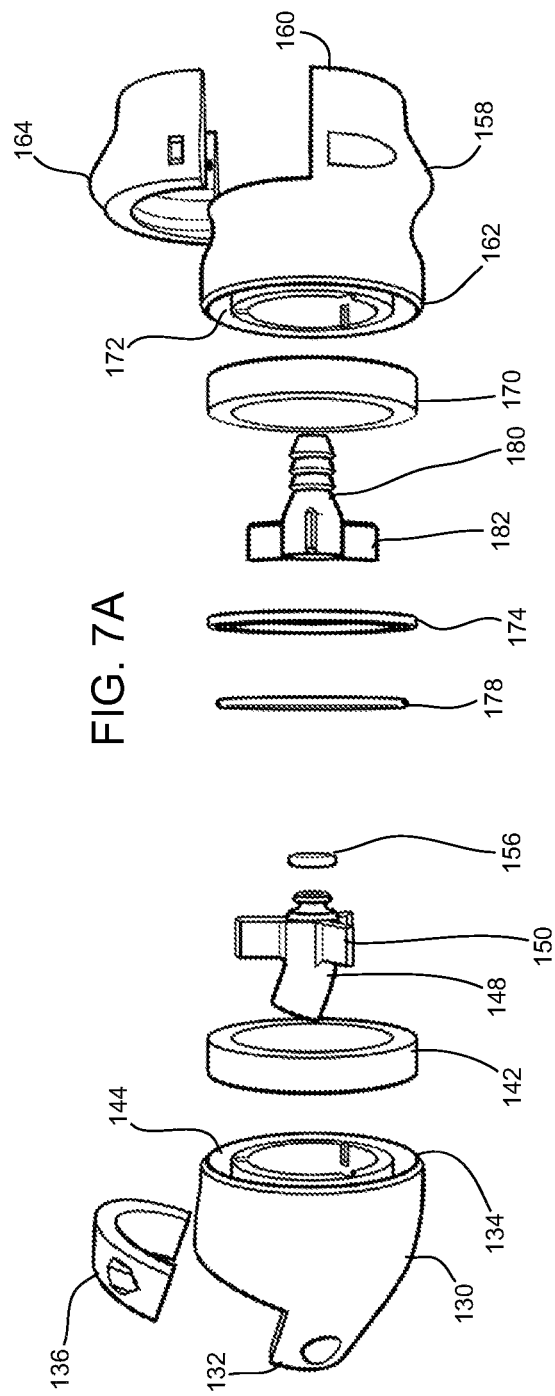
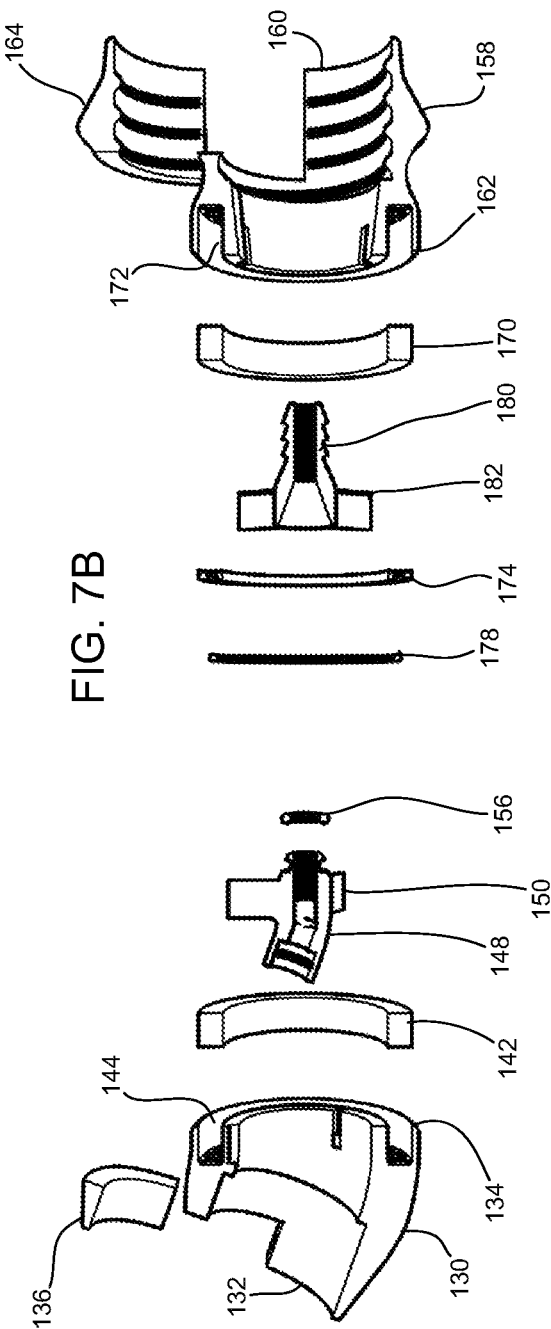
FIG. 7A
FIG. 7B

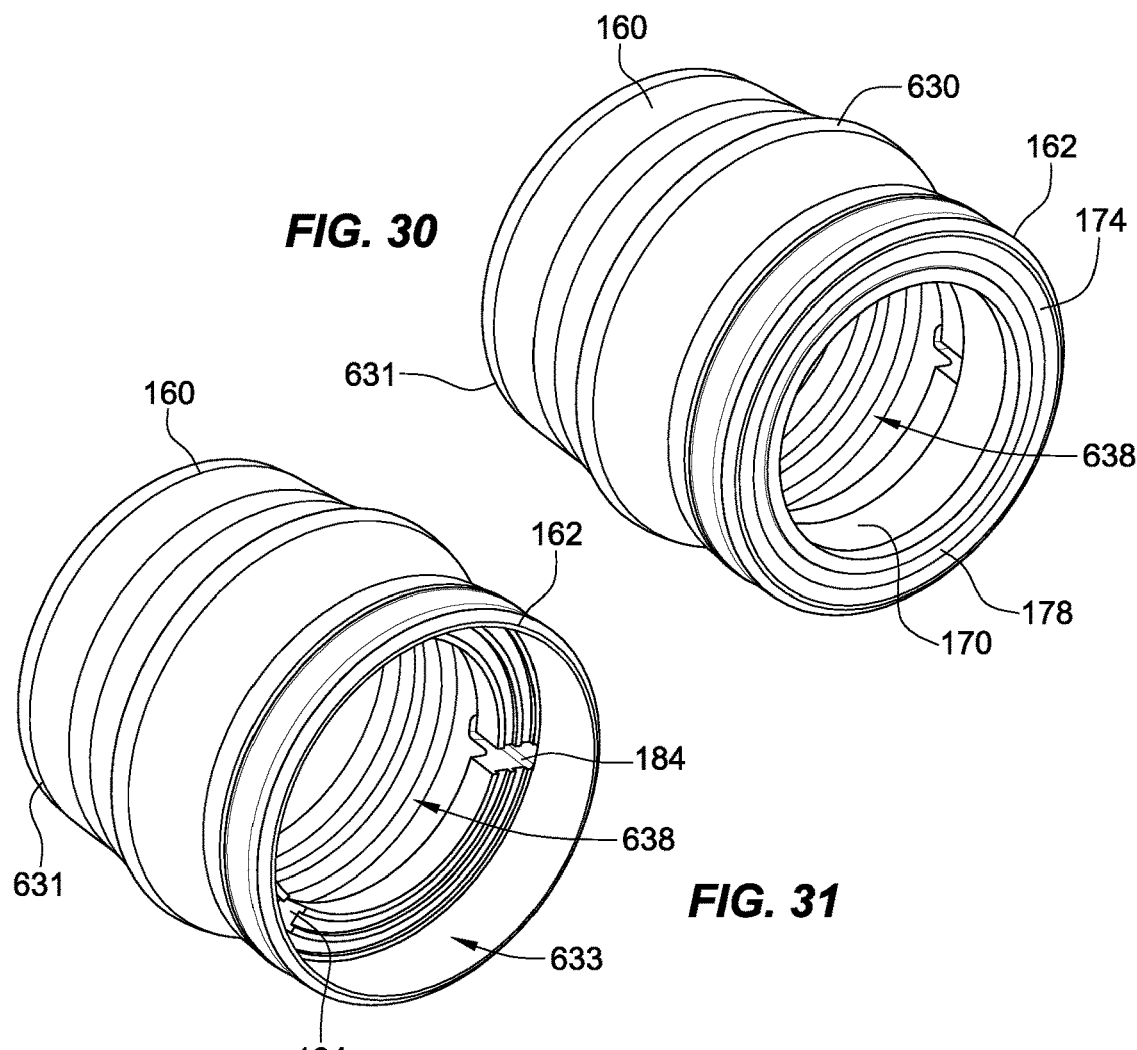
FIG. 30
FIG. 31
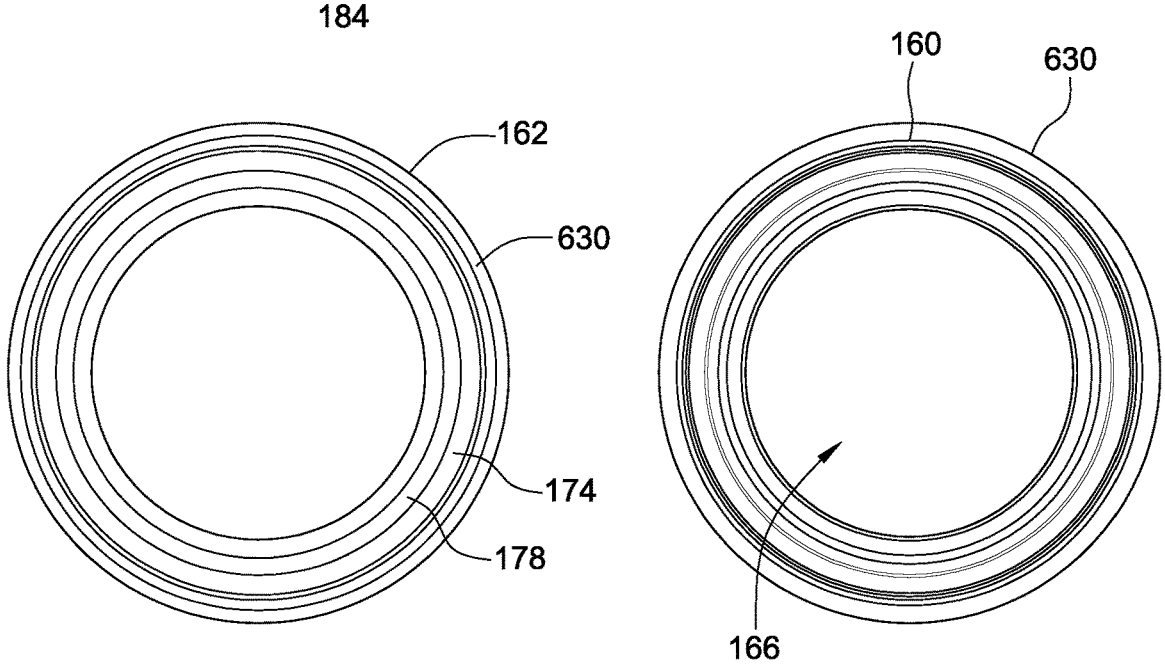
FIG. 32  FIG. 33

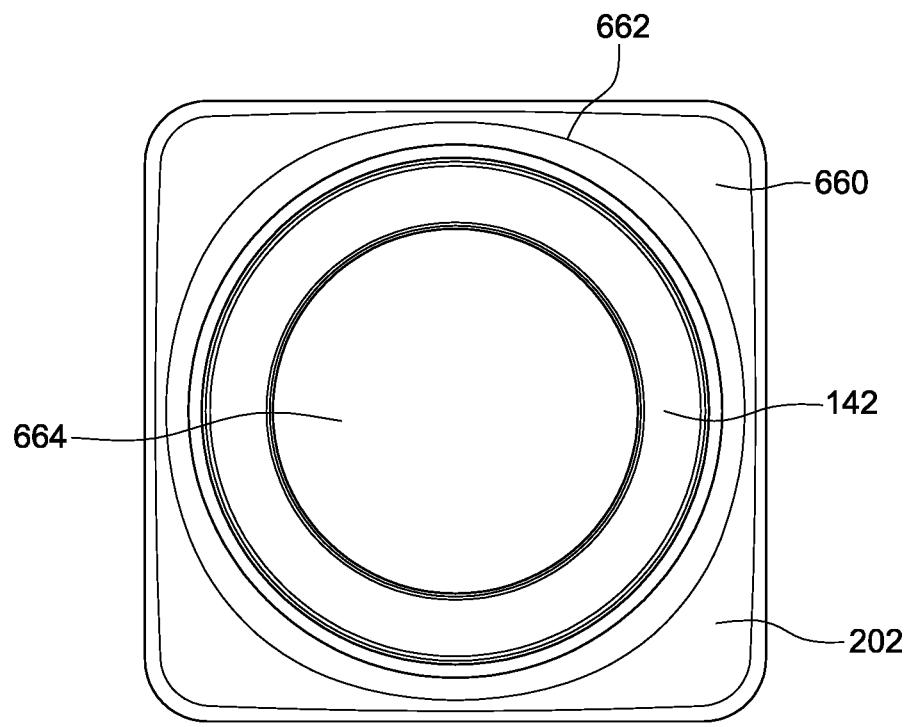
FIG. 44
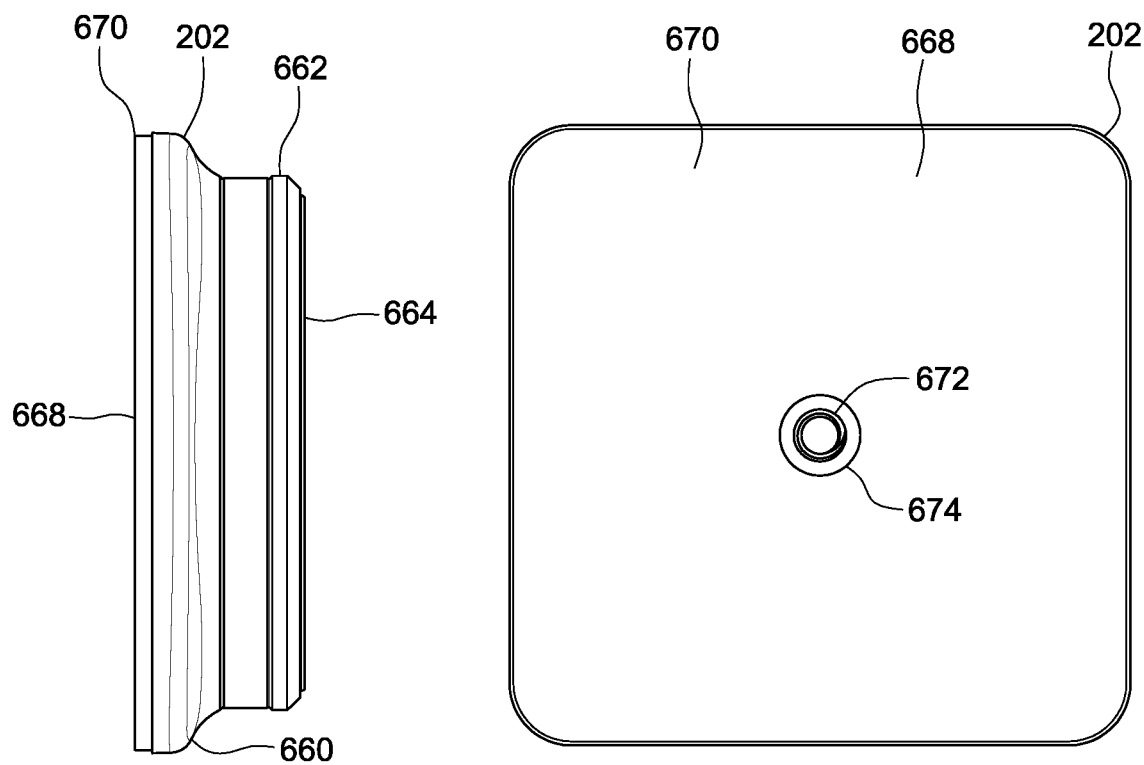
FIG. 45  FIG. 46

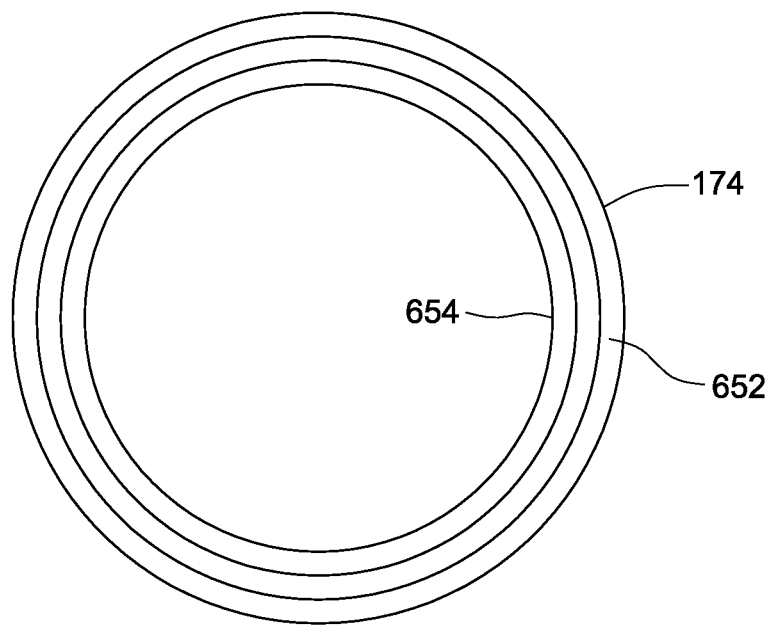
FIG. 47
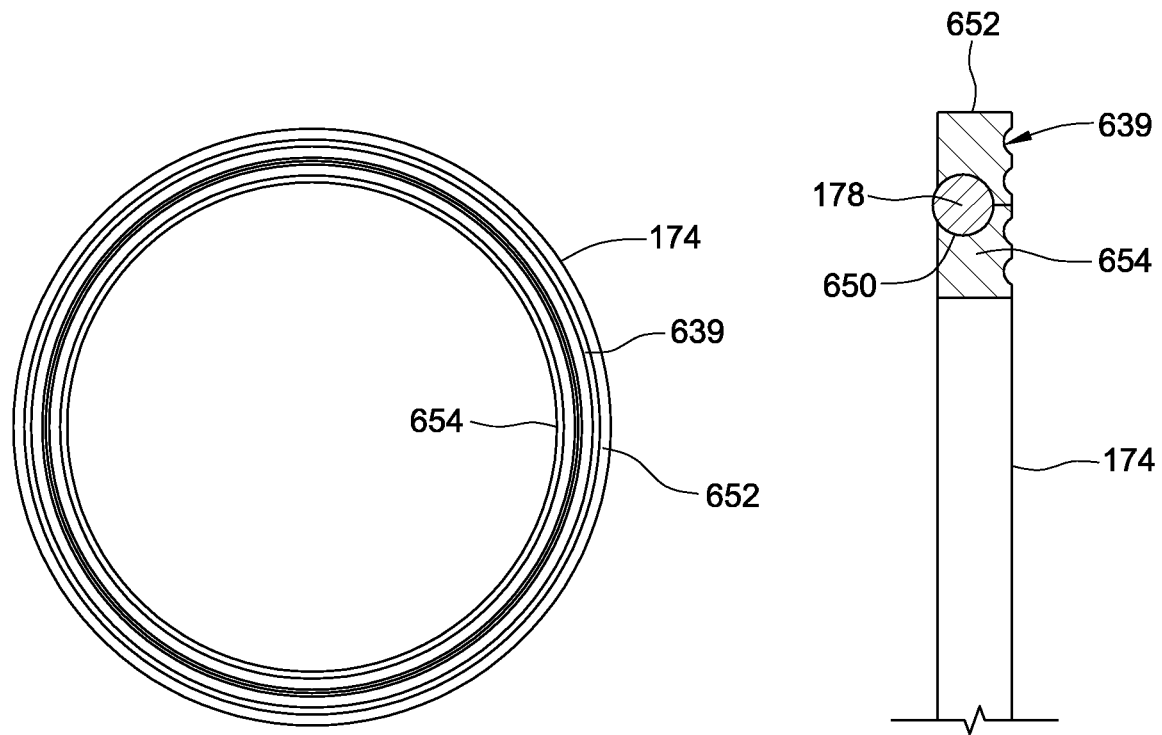
FIG. 48  FIG. 49

GAS DELIVERY SYSTEM

CROSS-REFERENCE TO RELATED APPLICATIONS

This application is a continuation of U.S. patent application Ser. No. 15/813,157, filed Nov. 15, 2017, which in turn claims the benefit of U.S. Provisional Application No. 62/423,430, filed Nov. 17, 2016, both of which are hereby incorporated by reference as if fully set forth herein.

This application is also related to U.S. Provisional Application No. 62/363,334, filed Jul. 18, 2016, which is incorporated herein by reference as if fully set forth herein.

This application is also related to the Application entitled HYDRATION AND AUDIO SYSTEM that was assigned U.S. Provisional Application No. 62/423,415, the disclosure of which is incorporated herein by reference as if fully set forth herein.

This application is also related to the Application entitled HYDRATION SYSTEMS AND COMPONENTS THEREOF that was assigned U.S. Provisional Application No. 62/423,756, the disclosure of which is incorporated herein by reference as if fully set forth herein.

TECHNICAL FIELD

This disclosure generally relates to fluid delivery systems and various components of fluid delivery systems. More particularly, the disclosure relates to fluid delivery systems having a magnetic quick connect and magnetic quick connects for fluid delivery systems. Certain embodiments relate even more particularly to fluid delivery systems and magnetic quick connects that include two fluid delivery channels, such as one for a hydration fluid and another for air.

BACKGROUND

Medical research has demonstrated the importance of maintaining adequate hydration to maintain a person's physical and mental health. Serious consequences can occur due to the lack of proper hydration. These consequences can range in severity from fatigue and nausea to loss of consciousness and even death. To maintain optimum health, physicians generally recommend that under normal conditions individuals drink at least eight 8 ounce (240 ml) glasses of water a day (for a total of a gallon of water per day). When an individual is under physical exertion, exposed to extreme environmental conditions, and/or over weight, the amount of fluids that the individual needs to consume generally increases because the individual's rate of fluid loss increases under such circumstances. Thus, regardless of whether a person is exercising, working, or simply resting, maintaining proper hydration and peak performance (both physical and mental) requires the regular ingestion of fluids, which in turn requires the availability of fluids to ingest.

Various portable devices have been developed to help address the availability problem. These devices have included, for example, aluminum canteens and plastic water bottles. While these devices are reasonably light, durable, and inexpensive, they do not allow hands-free fluid consumption, which may be desirable or even extremely important in some applications. In addition, they are often awkwardly mounted to a waist belt or in a pocket of a backpack, making the process of accessing them during certain activities impractical and even unsafe. As a result, individuals using these types of portable devices often go without fluids longer than they should. Frequently, this is because the user has to wait for a suitable break in their activity before safely reaching for the water bottle or canteen. Because of the inconvenience and/or safety issues, individuals using these types of devices also often wait until they feel thirsty before finding a suitable break in whatever activity they are engaged to have a drink. The problem with this approach, however, is that by the time a person is thirsty, they are already dehydrated and thus their body is no longer capable of optimal performance. In addition, if an individual waits too long to properly hydrate, their body can begin to cramp, causing pain and a further reduction in the individual's ability to engage in physical activity. Moreover, a person does not immediately recover from dehydration by drinking water. This is because the cells of the human body begin to shut down once the human body becomes dehydrated, and it is only through a slow process of re-hydration that the cells of the body can recover and begin to function properly again.

More recently, personal hydration systems have been developed that offer a number of advantages over water bottles and canteens, including improved fluid delivery capabilities and convenience. These systems frequently include either a semi-rigid or flexible bag-like fluid reservoir that may be carried in a pack on the user's back or waist. These systems permit a user to drink more frequently while engaged in a variety of sporting, recreational, and work-related activities because a long flexible drink tube is connected to the reservoir through an exit port at one end and terminates in a mouthpiece with a bite valve at the other end. The tube is long enough to allow the mouthpiece to be carried in the user's mouth to enable the user to draw water from the reservoir at will. Examples of personal hydration systems of this type and mouthpieces therefor are disclosed in U.S. Pat. Nos. 5,727,714, 5,060,833, 5,085,349, 6,070,767, and 7,490,740.

Although personal hydration systems have generally provided a significant advance over traditional water bottles, they continue to suffer from a number of shortcomings. One shortcoming, for example, has been that the components of the hydration system downstream from the fluid reservoir have historically been either permanently secured together or secured together via a tight friction fit that tends to be difficult to establish or release. Although these types of connection structures provide suitable fluid-tight seals, they are not optimal in terms of both providing a fluid-tight seal and permitting components downstream of the reservoir to be quickly and repeatedly interchanged by a user. Moreover, these structures are not designed to permit downstream components to be easily and safely disconnected in the event of an emergency or in the event of something snagging one of the downstream components.

Mechanical quick connects, such as those described in U.S. Pat. No. 7,073,688, have been employed to allow downstream components in a personal hydration system to be quickly and repeatedly connected and disconnected. Mechanical quick connects also allow a user to quickly and easily interchange downstream components. As a result, mechanical quick connects are quite useful in many applications. One drawback of mechanical quick connects, however, is that once they are connected they can only be disconnected by pressing a release button. This can pose a significant safety problem in a number of sporting and work-related activities. Furthermore, depending on the location of the mechanical quick connect in the fluid delivery system, two hands may actually be required to connect and/or disconnect the male and female members of the quick connect provided on the mating components of the hydration system. And certainly, mechanical quick connects are not designed to permit users to attach or detach components with a single hand, or without the benefit of the user visualizing the male and female members of mechanical quick connect that are to be connected or disconnected.

Another shortcoming in these conventional systems is that the drink tube is left dangling. As a result, when the user releases the mouthpiece located on the terminal end of the of the drink tube from the user's mouth, the tube will fall away from the user's mouth and require the user to retrieve the drink tube and put the mouthpiece back in his or her mouth the next time another drink is desired. However, it may not be practical (or even safe) for a user to manipulate the drink tube in this manner during certain activities, for example, when the user is traveling at a high rate of speed, such as on bicycle, in a race car, or on a motorcycle. Yet, it is also not always practical, or even desirable, for the user to keep the mouthpiece in his or her mouth at all times.

Headgear has been developed to facilitate hands-free hydration. The headgear is designed to permit the bite-valve of the drink tube to be adjustably located in front of the user's mouth. A variety of different types of headgear of this type are described in U.S. Pat. No. 6,283,344 to Bradley, which is hereby incorporated by reference. The various types of headgear described in the Bradley patent are all designed to be worn on the user's head such that an intermediate portion of the drink tube is located vertically above the user's mouth. The configuration employed in the Bradley patent is designed so that when the user is riding a bicycle or the like, fluids can be provided from a back mounted hydration pack to the user via gravity or a siphon, thereby reducing the amount the user has to suck on the bite valve, which is located on the terminal end of the drink tube, to draw fluids from the hydration reservoir to the user's mouth. All of the connectors used in the headgear described in Bradley, however, are of the friction fit variety. As a result, the portion of the drink tube that extends from the headgear to the fluid reservoir are subject to being snagged by objects in the environment in which the user is performing his or her activity. For example, a tree limb could snag the drink tube as a bicyclist is riding past a tree. If the drink tube is snagged in this manner, the headgear can potentially be ripped from the user's head and/or the user can be injured.

Another shortcoming of personal hydration systems has been providing a reservoir that can be readily accessed by the user for cleaning. To address this problem, hydration bags have been developed that include an opening defined by generally opposed ribs that are sealed by compressing the ribs together, similar to how a ZIPLOCK™ brand storage bag is sealed. Another solution to this problem has been the use of a roll top, or folded top, which is closed by rolling or folding the top, much like a dry bag used in camping. Another proposed solution to this problem is described in U.S. Pat. No. 6,820,780, in which a personal hydration system is described that includes a hydration bag with a relatively large diameter fill port and mating cap. One disadvantage of each of these approaches is that because the hydration bags are extremely flexible, it is often awkward or difficult for a user to fill the hydration bag without spilling fluids. It is also difficult for the user to fill the bags to their maximum capacity. Further, to fill a hydration bag, the bag must be removed from its pack, and once filled the bag must then be stuffed back in the pack, which can be challenging.

Another shortcoming of the personal hydration systems of the type described above is that the user has to suck water up the lengthy drink tube. The process is much like drinking through a straw. The user bites on the bite-valve included in the mouthpiece and then sucks on the mouthpiece to draw water or other fluid from the fluid reservoir into the user's mouth. The rate at which fluid from the reservoir is delivered to the user will depend on the amount of suction, as well as the amount of resistance to fluid flow within the system. And while the process is fairly straight-forward and simple, in certain situations it can be taxing for the user. This can occur, for example, when the user is already exerting significant energy and breathing hard due to exercise or where the user is perhaps more elderly and/or frail. This is because these systems also require the user to hold their breath while they suck fluids from the reservoir to drink, which is not always practical, such as when the user is already breathing hard and short of breath.

Hydration systems have been provided with powered pumps or pressurizing mechanisms so that a user does not have to suck fluids from the reservoir or hold their breath while drinking. Hydration systems provided with these features have thus far still suffered from many of the other drawbacks discussed above. In addition, pump housings have not been designed to readily connect and disconnect to the outlet ports of the hydration bags. This can, for example, make it difficult to connect and disconnect the pump at will from the hydration bag. This can also result in the weight of the pump, power source, and housing being distributed in a manner that may not be ideal.

The actuation switch in systems including a pump also have room for improvement. For example, the actuation switch in some of these systems has been located on the fluid delivery tube itself, which requires a user to reach his hand to the tube to actually activate the pump. Depending on activity in which the user is engaged, this may or may not be practical. Actuation switches have also been located on handlebars of a bicycle, but this approach has required the user to remove one of his or her hands from the handlebar grips to activate the switch, which, depending on the conditions of the bike path and speed of the bike, may not be safe. U.S. Patent Publication 2004/0045980 A1 to Duncan Robins describes a personal hydration system in which a mouth activated switch is provided in the mouthpiece of the drink tube. The design described in the Robins publication, however, requires the user to keep the mouthpiece in his or her mouth during use, which is not always practical or even desirable during many activities. Alternatively, as with known suction-type (or pump-less) hydration systems discussed above, the user can allow the drink tube to dangle free between drinks and then grab the drink tube and place the mouthpiece in his or her mouth when a drink is desired. But, just as with conventional suction-type hydration systems, it may not always be practical (or even safe) for a user to manipulate the drink tube in this manner.

Further, as the use of liquids with dissolved salts and/or sugars increases in hydration systems (both pumped and pump-less), the cleanliness of hydration systems and their component parts will become a greater concern to users. This is because the use of sugars in a hydration system can lead to contamination due to trapped residue and/or accumulation of bacteria, particularly in the area of a bite-valve, mouthpiece, and/or pump. Thus, hydration systems and/or components thereof that are readily cleanable are desirable.

Forced air helmets are also known, for example, in the racing industry. The forced air helmets have a helmet interface with an input tube that is in communication with the interior of the helmet through a port in wall of the helmet. A supply of forced air (which may be cooled to help keep the driver cool and/or filtered to supply a source of clean air for the driver to breath) is connected to the input tube of the helmet interface. For example, the distal end of a hose can be connected to the helmet interface and the proximal end of the hose to the air supply. In known forced air systems, the hose is connected via an interference fit to the input tube. In many instances, the interference fit is supplemented by wrapping duct tape or zip ties around the distal end of the hose where it overlaps the input tube to further increase the strength of the interference fit between the hose and input tube, and to make sure sit does not fit does not fail during use. This, however, can pose safety risks when a driver is attempting to exit the vehicle, or needs to be extracted from a vehicle, during emergency situations

SUMMARY

A magnetic quick connect for a fluid delivery system includes a male coupling member and a female coupling member. The male coupling member includes a first end and a second mating end. The male coupling member has an interior wall defining a first outer fluid communication path extending within the male coupling member. The male coupling member further includes a first inner member disposed within the first outer fluid communication path. The first inner member defines a first inner communication path extending within the first outer fluid communication path. The male coupling member further includes a first magnetic material disposed adjacent to the second mating end.

The female coupling member includes a first end and a second mating end. The female coupling member has an interior wall defining a second outer fluid communication path extending within the female coupling member. The female coupling member further includes a second inner member disposed within the second outer fluid communication path. The second inner member defines a second inner communication path extending within the second outer fluid communication path. The female coupling member further includes a second magnetic material disposed adjacent to the second mating end.

In a coupled configuration, the male and female coupling members are detachably held together by an attractive force between the first and second magnetic materials such that the first and second outer communication paths are held in fluid communication, and the first and second inner communication paths are held in fluid communication.

In some approaches, at least a portion of the first inner communication path of the male coupling member extends coaxially within the first outer fluid communication path of the male coupling member. Similarly, in some approaches, at least a portion of the second inner communication path of the female coupling member extends coaxially within the second outer fluid communication path of the female coupling member.

The first inner member of the male coupling member may include a protrusion, and in some approaches a tapered protrusion. The second inner member of the female coupling member may include a recess adapted to receive the protrusion, and in some approaches the recess may be tapered.

In some approaches, the first inner member includes an inner O-ring disposed about the protrusion. The inner O-ring forms a liquid-tight seal between the protrusion and the recess of the second inner member when the male and female coupling members are in the coupled configuration.

The female coupling member may further include an outer O-ring. The outer O-ring forms a fluid-tight seal between the male coupling member and the female coupling member when the male and female coupling members are in the coupled configuration.

The female coupling member may further include a cap disposed adjacent to the second magnetic material.

The first outer and inner fluid communication paths preferably extend coaxially with the first magnetic material. Similarly, the second outer and inner fluid communication paths preferably extend coaxially with the second magnetic material.

In some approaches, the first magnetic material is ring-shaped and extends around the first outer fluid communication path, and the second magnetic material is ring-shaped and extends around the second outer fluid communication path.

Preferably, at least one of the first magnetic material and the second magnetic material is a permanent magnet. The first magnetic material and the second magnetic material may comprise a material selected from the group consisting of a ferromagnetic material and ferrimagnetic material.

In some approaches, an axial pull force that is greater than 48 ounce-force and less than 128 ounce-force between the male coupling member and female coupling member is required to decouple the male and female coupling members. In other approaches, an axial pull force that is greater than 64 ounce-force and less than 96 ounce-force between the male coupling member and female coupling member is required to decouple the male and female coupling members. In still other approaches, an axial pull force that is greater than 72 ounce-force and less than 88 ounce-force between the male coupling member and female coupling member is required to decouple the male and female coupling members.

The male coupling member may further include a first collar disposed at the second mating end of the male coupling member, and the female coupling member may further include a second collar disposed at the second mating end of the female coupling member.

In some approaches, the first magnetic material is disposed within the first collar and the second magnetic material is disposed within the second collar.

The first collar and second collar may define an annular channel that is open toward the abutting surfaces of the first and second collars. The first magnetic material is disposed within an annular channel defined by the first collar, and the second magnetic material is disposed within an annular channel defined by the second collar.

In some approaches, the first collar defines at least part of a surface of the male coupling member that abuts the female coupling member when the male and female coupling members are coupled together, and the second collar defines at least part of a surface of the female coupling member that abuts the male coupling member when the male and female coupling members are coupled together.

In some approaches, at least one of the male coupling member and female coupling member includes a clamp portion removably securable to the first end of at least one of the male coupling member and female coupling member. The clamp portion is adapted to secure a hose to the at least one coupling member.

In still other approaches, at least one of the first inner member and second inner member includes a barbed hose connector adapted to secure a hose to the at least one inner member.

BRIEF DESCRIPTION OF THE DRAWINGS

FIG. 2A is an exploded perspective view of a personal hydration and air cooling system with a two-channel fluid delivery system that includes a mouthpiece assembly, magnetic quick connect, tubing defining a first fluid channel for carrying a first fluid, and a splicer for introducing a second fluid into the tubing.

FIG. 2B is a cross-sectional perspective view of the splicer and tubing of the fluid delivery system of FIG. 2A.

FIG. 7A is a side elevation exploded view of the magnetic quick connect of FIG. 4A.

FIG. 7B is a sectioned side elevation exploded view of the magnetic quick connect of FIG. 4A.

FIG. 30 illustrates a perspective view of the hose side connector of the magnetic quick connect of FIG. 23 from its downstream end.

FIG. 31 illustrates a perspective view of the hose side connector of the magnetic quick connect of FIG. 23 from its downstream end with an end cap and a magnetic material removed.

FIG. 32 illustrates a downstream end view of the hose side connector of FIG. 30.

FIG. 33 illustrates an upstream end view of the hose side connector of FIG. 30.

FIG. 44 illustrates a front view of the quick connect holder of FIG. 43.

FIG. 45 illustrates a side view of the quick connect holder of FIG. 43.

FIG. 46 illustrates a back view of the quick connect holder of FIG. 43.

FIG. 47 illustrates a front view of the end cap and O-ring disposed at the downstream or mating end of the hose side connector shown in FIG. 30.

FIG. 48 illustrates a back view of the end cap disposed at the downstream or mating end of the hose side connector shown in FIG. 30.

FIG. 49 is a cross-sectional view through the end cap and O-ring combination shown in FIG. 47.

DETAILED DESCRIPTION

While it should be understood that the inventions described herein are described in connection with particular examples, the scope of the inventions are not limited to the specific examples. Rather, those skilled in the art will appreciate after reviewing the present disclosure that the following teachings can be used in a much wider variety of applications than the examples specifically mentioned herein.

Figure 1:
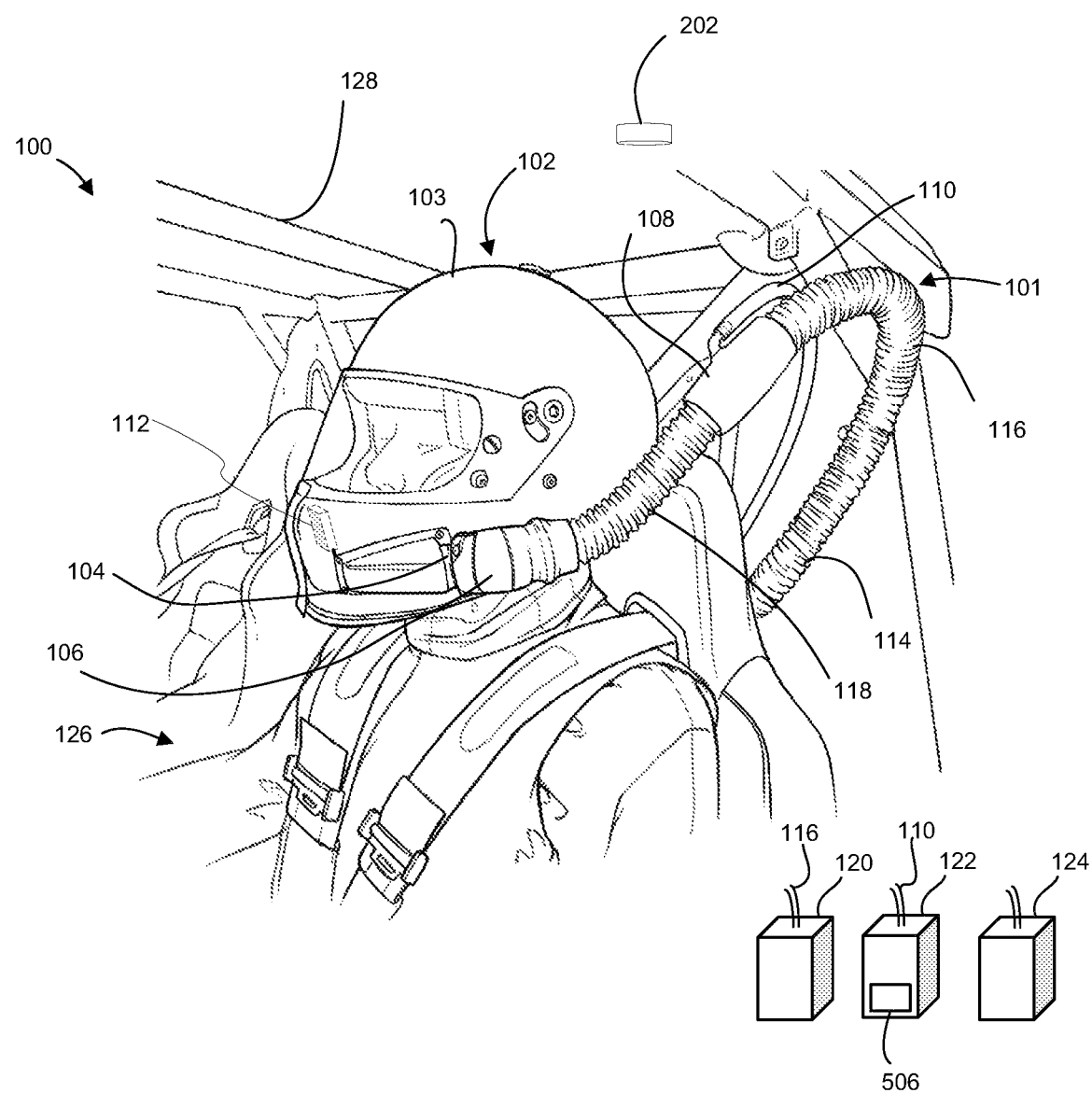
FIG. 1 illustrates an exemplary race car with a personal hydration and air cooling system that includes a two-channel fluid delivery system.

Referring now to the drawings in which like reference numerals designate like or corresponding components throughout the drawings, there is shown in FIGS. 1 and 2 a personal hydration and air cooling system 100 according to the present disclosure. The hydration and air cooling system 100 includes a number of distinct aspects. Distinct aspects of the hydration and air cooling system 100 include, for example, a fluid delivery system 101, a headgear assembly 102 having a helmet 103 with a helmet interface 104, a mouthpiece assembly 112, a magnetic quick connect 106, a tube 114 having first and second tubing portions 116, 118, and a splicer 108.

It is to be expressly understood that each of these various aspects, as well as other inventive features of the hydration and air cooling system 100 described below, both individually as well as in combination, all form distinct and separately patentable inventions contemplated by the present disclosure. Thus, for example, while each of these distinct aspects have all been incorporated into an illustrative embodiment of a hydration and air cooling system 100, it is to be expressly understood that because each of these aspects are separately patentable, they can be used individually or collectively in many other hydration systems, air delivery systems, and/or fluid delivery systems without departing from the spirit of the present disclosure. Thus, it is also to be expressly understood that the present patent disclosure is not restricted to the fluid delivery system embodiments described herein. Indeed, as will become apparent to those skilled in the art after reviewing the present disclosure, one or more aspects of the hydration and air cooling system 100 may readily be incorporated into other vehicles, personal hydration systems and/or fluid delivery systems without departing from the scope of the present disclosure. By way of illustration, but not limitation, the magnetic quick connects of the present disclosure, may, for example, be used in a host of fluid delivery systems unrelated to personal hydration systems, including in gas delivery systems, such as a variety of powered or supplied air delivery respirator systems. Furthermore, although shown on only the driver side of the vehicle 128, one or more hydration and air cooling systems 100 may be provided at any suitable location of the vehicle 128, such as at a passenger side or rear seat.

As discussed in greater detail herein, the personal hydration and air cooling system 100 includes a fluid delivery system 101 and one or more fluid sources (e.g., first fluid source 120 and second fluid source 122), and may further include an audio source (e.g., audio source 124). The fluid delivery system 101 includes everything downstream of the fluid sources 120, 122.

The fluid and audio sources may be supported directly or indirectly on the frame of a vehicle 128 without the user 126 having to carry the fluid and/or audio sources on his or her person. In particular, FIG. 1 illustrates a user 126 driving a vehicle 128 in the form of a race car. The fluid and/or audio sources may be disposed within the cabin of vehicle 128 so as to be supported directly or indirectly by the frame of the vehicle 128 at a location behind the user 126.

Referring to FIG. 1, a primary fluid delivery tube 114 has a first tube portion 116 and a second tube portion 118. The first tube portion 116 is connected at one end to a first fluid source 120. The first fluid source is preferably an air source, and may include a fan to move air to the user. The air may be drawn from the ambient air or may be drawn from an air reservoir. The first fluid source 120 may be used to provide air to a user 126. Providing air to user 126 may be desirable to provide a source of cooling for user 126. In some applications, providing filtered or clean air to user 126 will also ensure user 126 has a source of clean air to breathe, thereby limiting the inhalation of undesirable gasses or particles, such as dust particles, by user 126 during a race or other activity. In this way, the hydration and air cooling system 100 is provided with an air subsystem that supplies a source of cooling, as well as a source of breathable air to the user 126. A filter or other media may be included at any suitable portion of air subsystem of the hydration and air cooling system 100 to improve the quality of the air supplied to the user 126. For example, if source 120 comprises a fan, then a filter may be provided at the inlet to the fan.

The first tube portion 116 is connected at the other end to a splicer 108. As discussed in greater detail elsewhere herein, the splicer 108 includes a connector adapted to receive a portion of hydration input tube 110, namely tubing conduit 110*a*, to deliver a hydration liquid to mouthpiece assembly 112 of headgear assembly 102. The second tube portion 118 is connected at one end to the splicer 108 and at the other end to a magnetic quick connect 106. The magnetic quick connect 106 is secured at one end to headgear assembly 102. More particularly, the magnetic quick connect 106 is secured at one end to the helmet interface 104 of helmet 103. Interposing the magnetic quick connect 106 into the fluid delivery path of fluid delivery system 101 allows the upstream components of the fluid delivery system 101 to readily be attached to and detached from downstream components of the fluid delivery system 101.

Figure 3A:
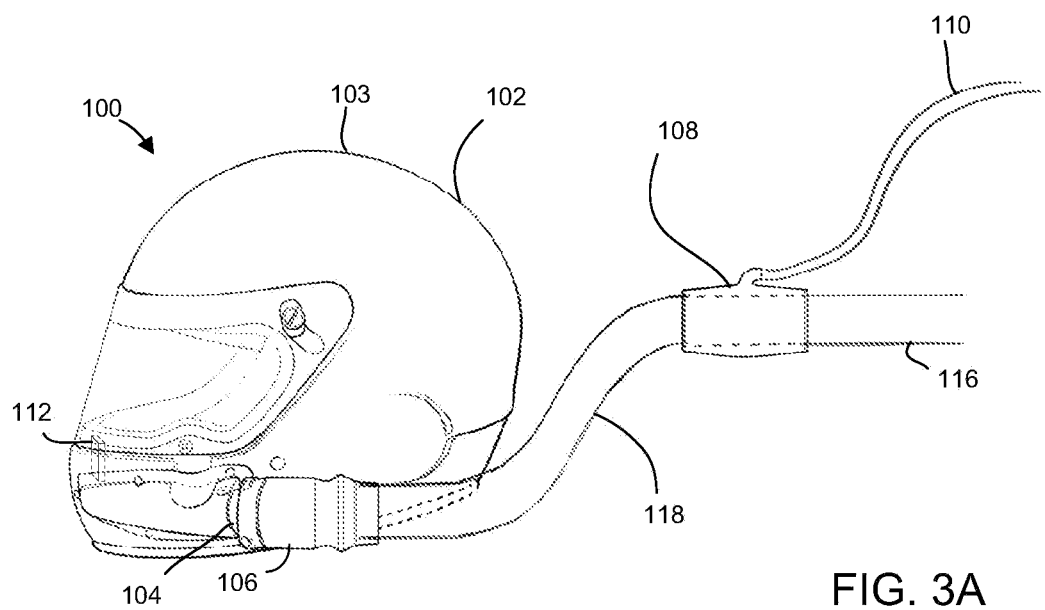
FIG. 3A illustrates an exemplary two-channel fluid delivery system helmet configuration.
Figure 3B:
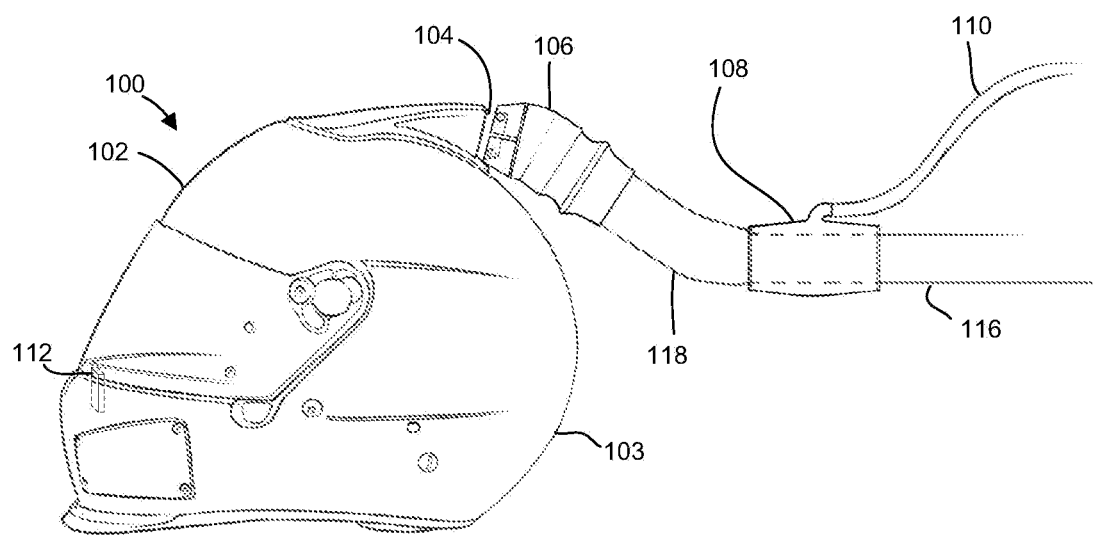
FIG. 3B illustrates another exemplary two-channel fluid system helmet configuration.

The magnetic quick connect 106 may be secured to a helmet interface 104 at a lower region of the helmet 103 as shown in in FIGS. 1 and 3A, or may be secured to an upper region of the helmet 103 as shown in FIG. 3B.

In some approaches, the magnetic quick connect 106 is coupled directly to the helmet 103 at the helmet interface 104. For example, the helmet interface 104 may include an input tube, and the magnetic quick connect 106 may be coupled to the input tube of the helmet interface 104. In still other approaches, described in greater detail elsewhere herein, a helmet-side portion of the magnetic quick connect 106 may be integrated directly into the helmet interface 104 of helmet 103. Those skilled in the art will also appreciate from reviewing the present patent document that a wide variety of potential applications exist for the liquid subsystem, air subsystem or both subsystems of the fluid delivery system 101. Further, many of the applications do not involve the fluid delivery system 101 being attached to a full-face helmet 103. Indeed, a user can use aspects of the fluid delivery system 101 according to the present patent document in a wide variety of non-helmeted and/or non-vehicle related applications. It is expressly contemplated that the hydration and air cooling system 100 may be used with a variety of headgear assemblies 102. An illustrative potential application of the two-channel fluid delivery system 101 includes, for example, fire fighter helmets equipped with a powered or supplied air respirator. Other protective systems, including safety helmets, welding helmets, face shields, chemical suits, bio-hazard suits, hoods, and headcovers configured to be connected to a powered or supplied air respirator system are also potential applications, as the two-channel fluid delivery system 101 of the present patent disclosure will allow the users of such systems to also be hydrated where those current systems presently lack a hydration option. Even if the hydration feature of fluid delivery system 101 is not desired for the users of those protective systems, however, the magnetic quick connect 106 may be interposed in the powered or supplied air delivery system of those protective systems to allow advantages in the coupling and uncoupling of the downstream components to the upstream components in the air delivery systems.

Aspects of the liquid subsystem of fluid delivery system 101 may likewise be used without the air subsystem. For example, a wide variety of helmets may be used to form a headgear assembly 102 of the present patent disclosure, including, but not limited to, motorcycle helmets (half, three quarter, open face, and full face), auto racing helmets (open face or full face), cycling helmets, skateboarding helmets, snowboarding and skiing helmets, mountain climbing helmets, military and other tactical helmets, fire helmets, safety helmets, and rescue helmets. The headgear assemblies 102 of the present patent disclosure may also be formed with headgear other than a helmet 103, such as with a head bracket. Illustrative potential applications of non-helmet-based headgear assemblies include, by way of example, backpackers, joggers, hikers, climbers, workers, firefighters, police, and military personnel.

Figure 4A:
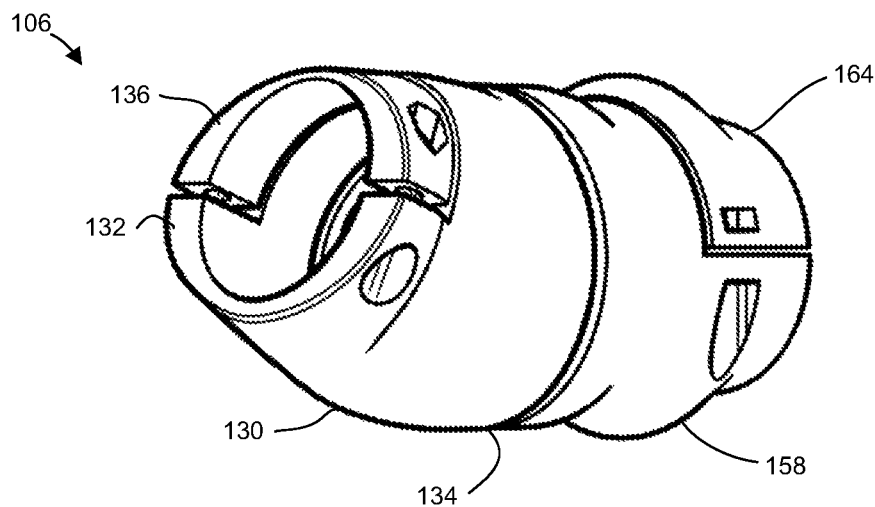
FIG. 4A is a perspective view of a magnetic quick connect.
Figure 4B:
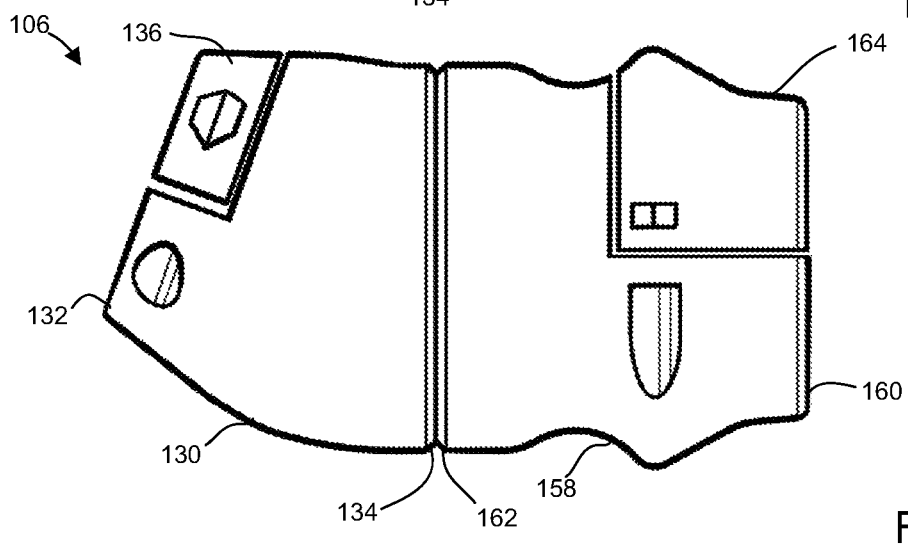
FIG. 4B is a side elevation view of the magnetic quick connect of FIG. 4A.
Figure 4C:
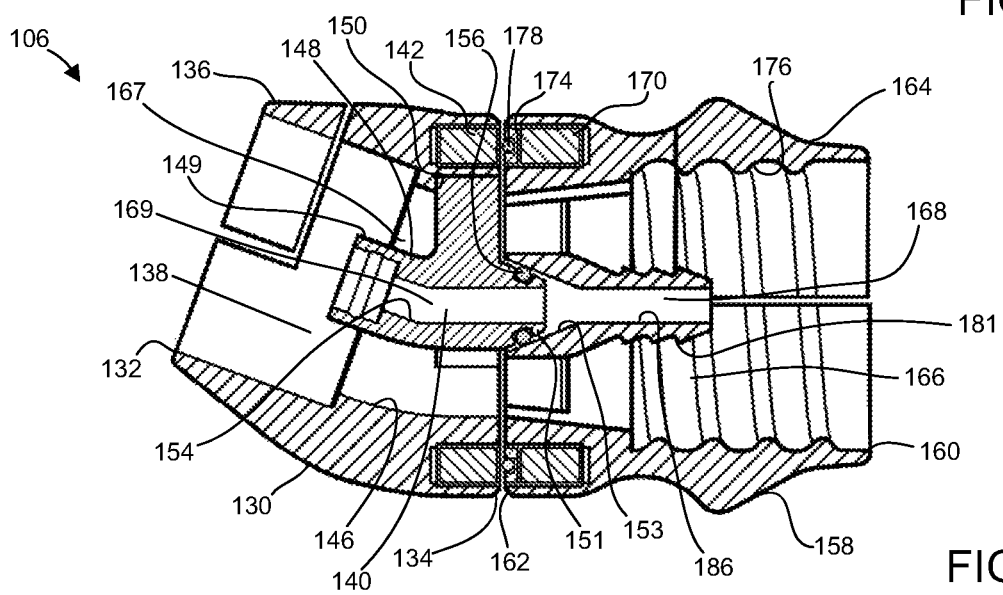
FIG. 4C is a sectioned side elevation view of the magnetic quick connect of FIG. 4A.

Referring now to FIGS. 4A-4C, the magnetic quick connect 106 includes a male coupling member 130 and a female coupling member 158. It is expressly contemplated that the features described herein with respect to the male coupling member 130 and the female coupling member 158 may be incorporated in either of the male coupling member 130 or the female coupling member 158. Further, the position of the male coupling member 130 and the female coupling member 158 may be reversed from that illustrated in FIG. 4A-4C. Thus, for example, the coupling members of the magnetic quick connect 106 may be referred generically to the downstream coupling member and upstream coupling member.

The male coupling member 130 has a first end 132 and a second mating end 134. The male coupling member 130 further includes an adjustable clamp portion 136. The adjustable clamp portion 136 may take the form of a "C-clamp", and may be removably connectable to the male coupling member 130, for example, through the use of screws or other fastening devices. In this way, the adjustable clamp portion 136 allows the male coupling member 130 to be secured to helmet interface 104 of helmet 103. For example, a user may remove the adjustable clamp portion 136 and position a tubing, such as an input tube, of the helmet interface 104 within the body of the male coupling member 130. The user then reconnects the adjustable clamp portion 136 to the male coupling member 130, thereby securing the male coupling member 130 to the helmet interface 104 of helmet 103. Other suitable mechanisms and fastening devices for securing the male coupling member 130 to a helmet 103 are expressly contemplated herein.

As shown in FIG. 4C, an outer fluid communication path 138 extends from the first end 132 to the second mating end 134 of the male coupling member 130. In a preferred approach, discussed in greater detail elsewhere herein, an inner fluid communication path 140 extends from the second mating end 134 into the male coupling member 130.

Figure 5:
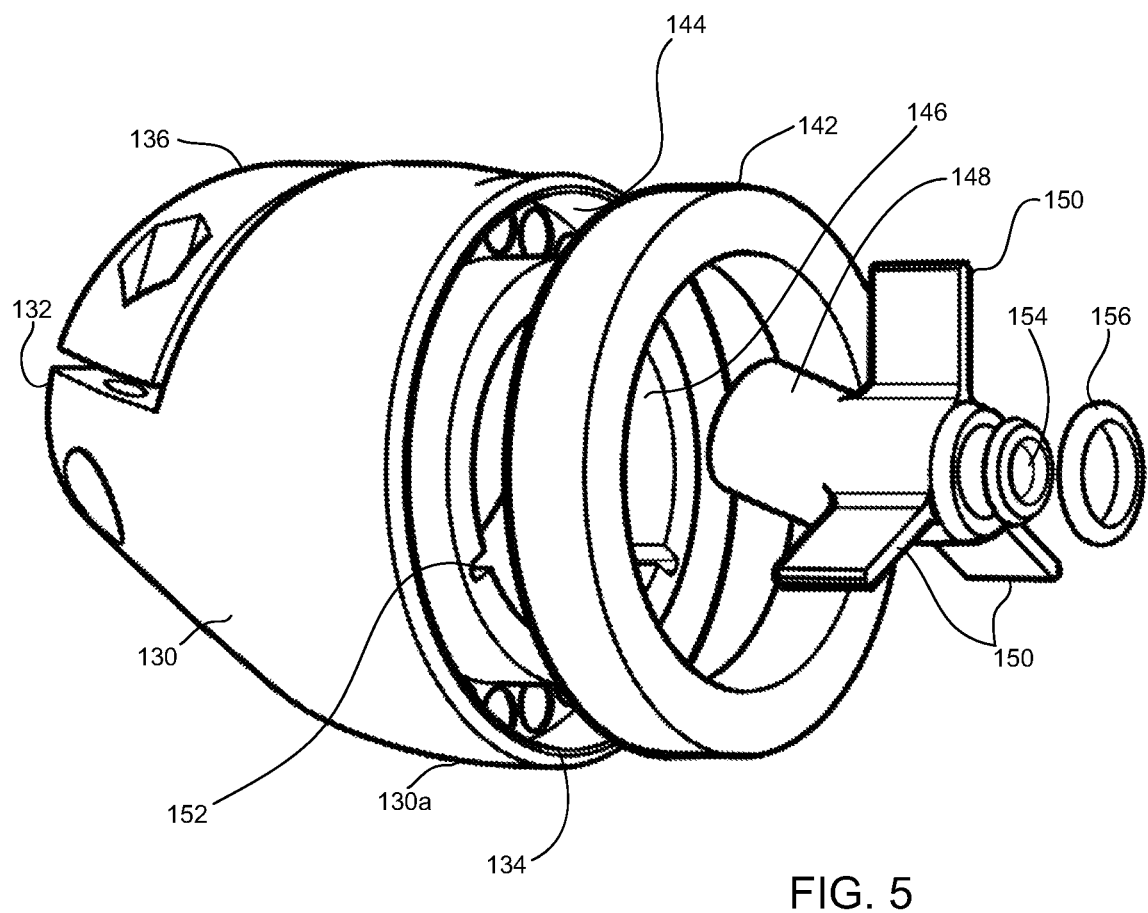
FIG. 5 is a perspective exploded view of the male coupling member of the magnetic quick connect of FIG. 4A.

Referring momentarily to FIG. 5, the male coupling member 130 includes a first magnetic material 142 disposed in a cavity 144. The first magnetic material 142 may be secured within the cavity 144 using glue or any other suitable securing fastener or adhesive.

The male coupling member 130 further includes an outer path wall 146 defining the outer fluid communication path 138. In a preferred approach, the outer fluid communication path 138 provides for the flow of atmospheric air or supplied air from first source 120 through the male coupling member 130.

The male coupling member 130 further includes an inner member 148 disposed within the outer fluid communication path 138. In a preferred approach, the inner member 148 is removably splined to the outer path wall 146. For example, the inner member 148 may be provided with one or more, and preferably three, fins 150 that are adapted to engage grooves 152 disposed in the outer path wall 146. The engagement of the fins 150 in the grooves 152 serves to hold the inner member 148 in place within the male coupling member 130. The inner member 148 may be held in place through any suitable approaches. For example, when the inner member 14 is intended to be a removable inner member 148, the fins 150 may form an interference fit with the grooves 152. When the inner member 148 is intended to remain within the male coupling member 130, an adhesive may be used to secure the fins 150 to the grooves 152. In still other approaches, the inner member 148 may be integrally formed with the male coupling member 130.

The inner member 148 defines an inner path wall 154 defining the inner fluid communication path 140. In a preferred approach, the inner fluid communication path 140 provides for the flow of water or other hydration liquids from source 122 through the male coupling member 130. In some approaches, the inner member 148 includes a receiving portion 149 adapted to receive a tubing conduit 111 within the receiving portion 149. In other approaches (not shown), the inner member 148 includes a barbed portion adapted to receive a tubing conduit 111 about the barbed portion. The tubing conduit may be connected to, for example, the mouthpiece assembly 112.

In a preferred approach, the inner member 148 provides an inner fluid communication path 140 that is coaxial with the outer fluid communication path 138 defined by the outer path wall 146. The coaxial disposition of the inner member 148 within the male coupling member 130 may be provided, for example, by the fins 150. In this way, the inner member 148 provides communication of a first fluid (e.g., water or other hydration liquid) through the inner fluid communication path 140, while the male coupling member 130 provides communication of a second fluid (e.g., air) through the outer fluid communication path 138.

While in the approach shown in FIGS. 4C and 5, the inner fluid communication path 140 of inner member 148 is coaxial with the outer fluid communication path 138 defined by the outer path wall 146, in other approaches, the inner fluid communication path 140 is not coaxial with the outer fluid communication path 138. In such approaches, a central axis of the inner fluid communication path 140 is axially offset with respect to a central axis of the outer fluid communication path 138. In a further example, the inner fluid communication path 140 may be defined by an inner path wall 154 that is disposed in proximity to, adjacent to, or in contact with an outer path wall 146 defining the outer fluid communication path 138.

In a preferred approach, the inner member 148 of the male coupling member 130 includes a protrusion 151 for engaging a corresponding recess 153 of an inner member 180 of the female coupling member 158, as discussed in greater detail elsewhere herein. In particularly preferred approaches, the protrusion 151 is tapered and the wall defining recess 153 has a corresponding taper.

In one approach, the inner member 148 is formed integrally with, or permanently secured to, the outer path wall 146 of the male coupling member 130 such that the inner member 148 and the male coupling member 130 define a unitary piece.

In another approach, the inner member 148 is adapted to be removably connectable to the male coupling member 130. For example, the fins 150 of the inner member 148 may be removably insertable into the grooves 152 of the outer path wall 146. The male coupling member 130 may further be provided with a locking mechanism to secure the inner member 148 in place within the male coupling member 130. Such a locking mechanism may provide for slight rotation of the inner member 148 relative to the outer path wall 146 of male coupling member 130 to secure the fins 150 of the inner member 148 against one or more locking tabs. In this way, a user may insert the inner member 148 into the male coupling member 130 when the user desires dual fluid flow to a helmet 103, and may remove the inner member 148 from the male coupling member 130 when dual fluid flow is not desired or unavailable.

In one approach, the male coupling member 130 is removably secured to the helmet interface 104 of helmet 103. In other approaches, a helmet-side coupling member (male or female) of the magnetic quick connect 106 is integrally formed with the helmet 103. For example, male coupling member 130 may be integrated with the helmet 103, thus providing helmet 103 with a helmet-integrated magnetic quick connect interface having an outer fluid communication path 138, and optionally an inner fluid communication path 140 disposed within the outer fluid communication path 138, and a first magnetic material 142 for detachably coupling with a tubing-side or upstream coupling member (e.g., a female coupling member 158), thereby forming a magnetic quick connect 106. In this way, the helmet-integrated magnetic quick connect interface may perform in substantially the same manner as the male coupling member 130 described herein. The helmet-integrated magnetic quick connect interface reduces the number of components within the fluid delivery system.

The magnetic quick connect 106 further includes a female coupling member 158 having a first end 160 and a second mating end 162. The second mating end 162 of the female coupling member 158 is adapted to be secured (e.g., magnetically secured) to second mating end 134 of the male coupling member 130, as discussed in greater detail elsewhere herein.

The female coupling member 158 includes an adjustable clamp portion 164. Similar to the adjustable clamp portion 136 of the male coupling member 130, the adjustable clamp portion 164 of the female coupling member 158 may take the form of a "C-clamp", and may be removably connectable to the female coupling member 158, for example, through the use of screws or other fastening devices. In this way, the adjustable clamp portion 164 allows the female coupling member 158 to be secured to a tubing such as tubing portion 118. For example, a user may remove the adjustable clamp portion 164 and position tubing portion 118 within the body of the female coupling member 158. The user may then reconnect the adjustable clamp portion 164 to the female coupling member 158, thereby securing the tubing portion 118 to the female coupling member 158. Other suitable mechanisms and fastening devices for securing tubing to the female coupling member 158 are expressly contemplated herein.

As shown in FIG. 4C, an outer fluid communication path 166 extends from the first end 160 to the second mating end 162 of the female coupling member 158. In a preferred approach, discussed in greater detail elsewhere herein, an inner fluid communication path 168 extends from the second mating end 162 into the female coupling member 158.

Figure 6:
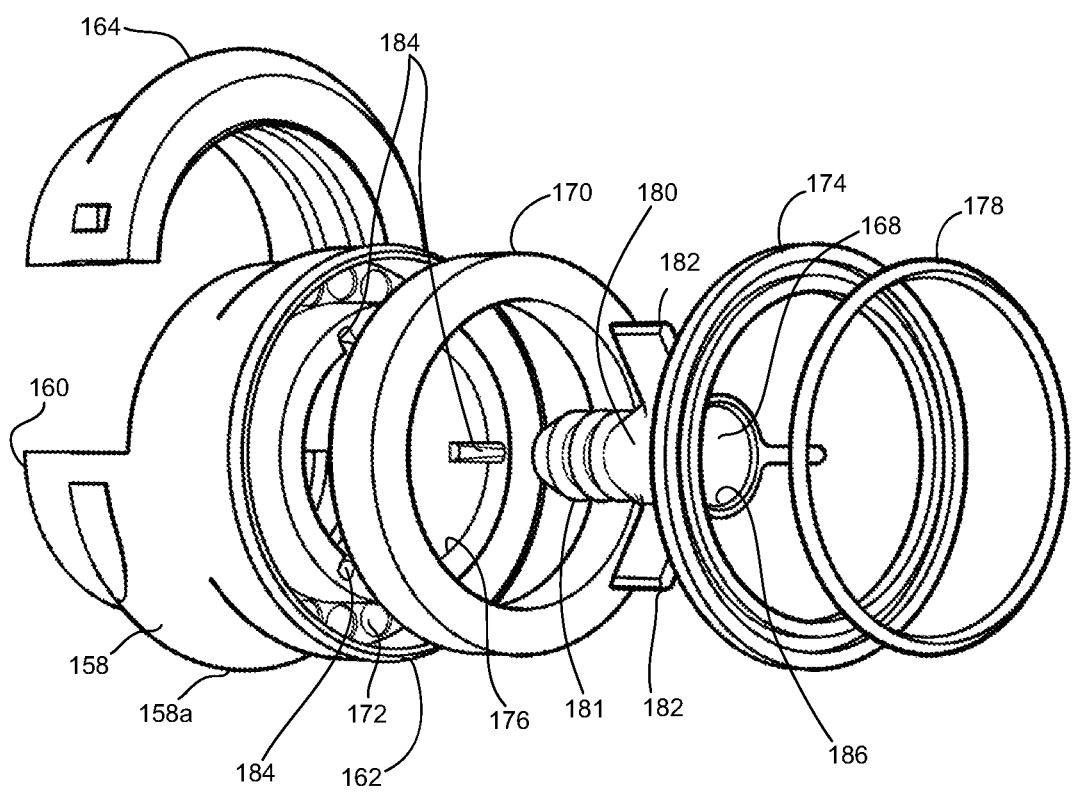
FIG. 6 is a perspective exploded view of the female coupling member of the magnetic quick connect of FIG. 4A.
Figure 8A:
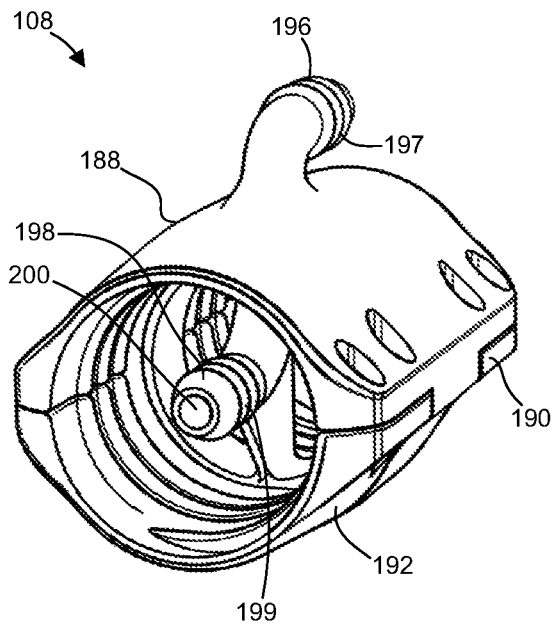
FIG. 8A is a perspective view of a splicer.
Figure 8B:
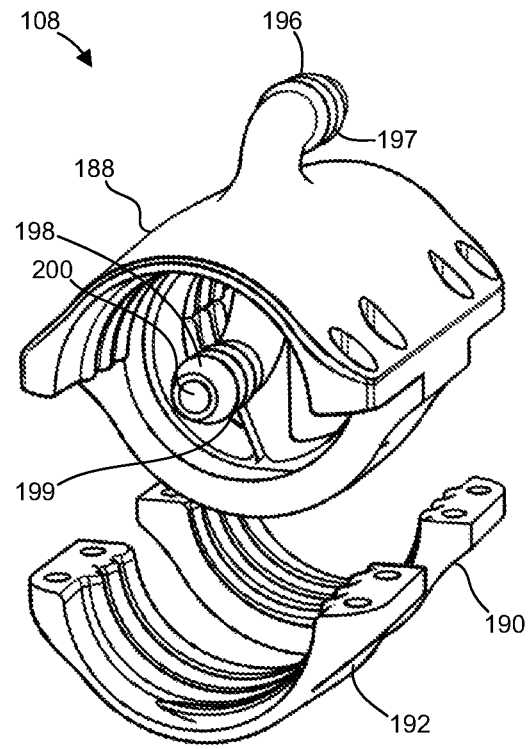
FIG. 8B is an exploded perspective view of the splicer of FIG. 8A.
Figure 8C:
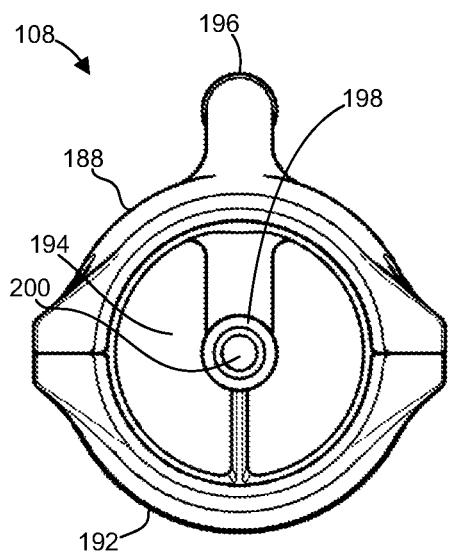
FIG. 8C is a front elevation view of the splicer of FIG. 8A.
Figure 8D:
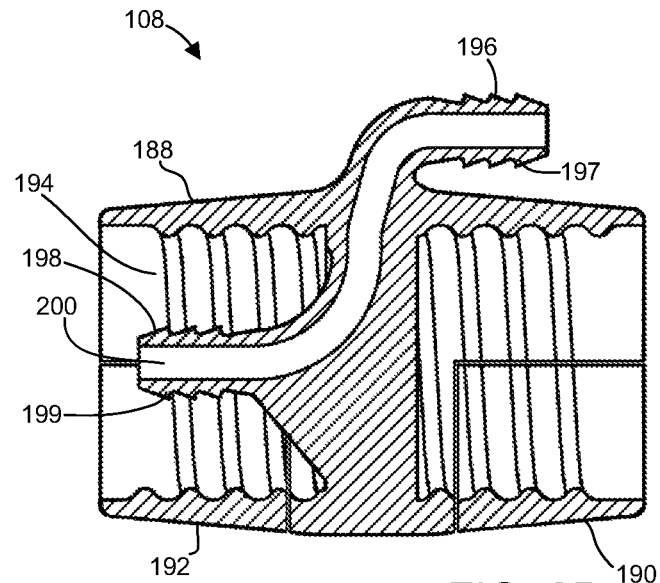
FIG. 8D is a sectioned side elevation view of the splicer of FIG. 8A.

Referring momentarily to FIG. 6, the female coupling member 158 includes a second magnetic material 170 disposed in a cavity 172. The second magnetic material 170 may be secured within the cavity 172 using glue or any other suitable securing fastener or adhesive. The second magnetic material 170 may be the same as or similar to the first magnetic material 142 of the male coupling member 130. The first and second magnetic materials may comprise a material selected from the group consisting of a ferromagnetic material and ferrimagnetic material. Preferably at least one of the first and second magnetic materials are a permanent magnet. The first and second magnetic materials 142, 170 are selected to have sufficient magnetic properties so that the magnetic force of attraction between them will detachably hold the male coupling member 130 and female coupling member 158 together, preferably with sufficient force to compress O-ring 178 sufficiently to provide a gas tight, or substantially gas tight, seal. As a result, the male and female coupling members 130, 158 of the magnetic quick connect 106 may be quickly and repeatedly connected and disconnected from one another.

The female coupling member 158 further includes an outer path wall 176 defining the outer fluid communication path 166. In a preferred approach, the outer fluid communication path 166 provides for the flow of atmospheric air or supplied air from first source 120 through the female coupling member 158.

The outer fluid communication path 166 of the female coupling member 158 is dimensioned and oriented to provide fluid communication with the outer fluid communication path 138 of the male coupling member 130, as shown for example in FIG. 4C.

The female coupling member 158 further includes an inner member 180 disposed within the outer fluid communication path 166. In a preferred approach, the inner member 180 is removably splined to the outer path wall 176. For example, the inner member 180 may be provided with one or more, and preferably three, fins 182 that are adapted to engage grooves 184 disposed in the outer path wall 176. The engagement of the fins 182 in the grooves 184 serves to hold the inner member 180 in place within the male coupling member 158.

The inner member 180 defines an inner path wall 186 defining the inner fluid communication path 168. In a preferred approach, the inner fluid communication path 168 provides for the flow of water or other hydration liquids from source 122 through the female coupling member 158. In some approaches, the inner member 180 includes a barbed portion 181 adapted to receive one end of tubing conduit 110b about the barbed portion 181. In other approaches, the inner member 180 may include a receiving portion adapted to receive the end of tubing conduit 110b within the receiving portion, similar to receiving portion 149 of male coupling member 130. The other end of tubing conduit 110b may be connected to, for example, an outlet nozzle 198 of the splicer 108, as discussed in greater detail elsewhere herein.

In a preferred approach, the inner member 180 provides an inner fluid communication path 168 that is coaxial with the outer fluid communication path 166 defined by the outer path wall 176. The coaxial disposition of the inner member 180 within the female coupling member 158 may be provided, for example, by the fins 182. In this way, the inner member 180 provides communication of a first fluid (e.g., water or other hydration liquid) through the inner fluid communication path 168, while the female coupling member 158 provides communication of a second fluid (e.g., air) through the outer fluid communication path 166.

While in the approach shown in FIGS. 4C and 6, the inner fluid communication path 168 of inner member 180 is coaxial with the outer fluid communication path 166 defined by the outer path wall 176, in other approaches, the inner fluid communication path 168 is not coaxial with the outer fluid communication path 166. In such approaches, a central axis of the inner fluid communication path 168 is axially offset with respect to a central axis of the outer fluid communication path 176. In a further example, the inner fluid communication path 168 may be defined by an inner path wall 186 that is disposed in proximity to, adjacent to, or in contact with an outer path wall 176 defining the outer fluid communication path 166. However, the male and female coupling members 130 and 158 should be configured so that when they are coupled together, the outer fluid communication paths 138, 166 are in fluid communication with one another and the inner fluid communication paths 140, 168 are in fluid communication with one another, but so that the outer fluid communication paths 138, 166 and inner fluid communication paths 140, 168 are separated from one another.

As shown in FIG. 4C, in a preferred approach, the inner member 180 of the female coupling member 158 includes a recess 153 for receiving a corresponding protrusion 151 of the inner member 148 of the male coupling member 130. In a particularly preferred approach, the recess 153 is tapered and the protrusion 151 has a corresponding taper.

The angle of taper is preferably in the range of 15° to 50° from the axis of the protrusion, more preferably, in the range of 20° to 40°, and even more preferably 25° to 35°. Tapering the protrusion 151 and protrusion receiving area, or recess 153, in this manner, helps the male and female coupling members to be self-centering with respect to one another. It also allows the quality of the seal between the O-ring 156 and the protrusion receiving surface to be increased.

To provide a liquid-tight or substantially liquid-tight seal between the male and female coupling members 130, 158, protrusion 151 on the inner member 148 may be provided with an O-ring 156. O-ring 156 is positioned and sized so that it will be compressed between protrusion 151 and the wall defining recess 153 when the male and female coupling members 130, 158 are coupled together.

To provide an airtight or substantially airtight seal between the male and female coupling members 130, 158, an O-ring 178 may be provided so that it is compressed between the two mating ends 134, 162 of the male and female coupling members 130, 158, respectively. Preferably the O-ring 178 is positioned so that when the male and female coupling members 130, 158 are coupled together it is compressed at an annular region between the outer path wall 146 of the outer fluid communication path 138 and the outer surface 130a of the male coupling member 130 and an annular region between the outer path wall 176 of outer fluid communication path 166 and the outer surface 158a of the female coupling member 158. O-ring 178 may be provided on the mating end of either male or female coupling member 130, 158, respectively. However, in the illustrated embodiment, it is disposed on the cap 174 provided at the mating end 162 of female coupling member 158. As best seen in FIG. 6, O-ring 178 is preferably disposed in an annular groove provided in cap 174.

Adhesive may be used to hold O-ring 178 within the annular groove. More desirably, the annular groove is C-shaped, so that the opening of the groove is narrower than the O-ring's diameter. This way the walls of the groove will hold the O-ring within cap 174. The C-shaped groove may be formed in cap 174 by 3D printing the cap, or alternatively using two concentric rings as described below in connection with FIGS. 27-28, and 47-49.

In one approach, the inner member 180 is formed integrally with, or permanently secured to the outer path wall 176 of the female coupling member 158 such that the inner member 180 and the female coupling member 158 define a unitary piece.

In another approach, the inner member 180 is adapted to be removably connectable to the female coupling member 158. For example, the fins 182 of the inner member 180 may be removably insertable into the grooves 184 of the outer path wall 176. The female coupling member 158 may further be provided with a locking mechanism to secure the inner member 180 in place within the female coupling member 158. Such a locking mechanism may provide for slight rotation of the inner member 180 relative to the outer path wall 176 of female coupling member 158 to secure the fins 182 of the inner member 180 against one or more locking tabs. In this way, a user may insert the inner member 180 into the female coupling member 158 when the user desires dual fluid flow to a helmet 103, and may remove the inner member 180 from the female coupling member 158 when dual fluid flow is not desired or unavailable.

While in the illustrated embodiment, the downstream end of magnetic quick connect 106 comprises a male coupling member 130, in other embodiments the downstream end of the magnetic quick connect 106 may comprise a female coupling member 158.

In the illustrated approach, magnetic quick connect 106 forms the proximal end of headgear assembly 102, but in other approaches, magnetic quick connect 106 may be interposed in the fluid delivery paths of fluid delivery system 101 in a different location. Moreover, in some approaches, a second magnetic quick connect may be included in one or both of the fluid delivery paths defined by fluid delivery system 101.

When connected, the male coupling member 130 and the female coupling member 158 collectively form the magnetic quick connect 106. Alignment of the male coupling member 130 and the female coupling member 158 may be facilitated by aligning the inner member 148 of the male coupling member 130 with the inner member 180 of the female coupling member 158. As shown, for example, in FIG. 4C, the inner member 180 of the female coupling member 158 may include a tapered recess 153 adapted to receive a tapered (e.g., conical) protrusion 151 of the inner member 148, as well as the O-ring 156, of the male coupling member 130. The angle of taper is preferably set in the range previously described.

As also shown, for example, in FIG. 4C, when connected, the outer fluid communication path 138 of the male coupling member 130 is in fluid communication with the outer fluid communication path 166 of the female coupling member 158. In this way, a fluid such as air may flow freely through a first fluid communication channel 167—that includes the outer fluid communication paths 138, 166 of the magnetic quick connect 106—to communicate the air from an air source (e.g., first fluid source 120) to the headgear assembly 102.

Similarly, when connected, the inner fluid communication path 140 of the male coupling member 130 is in fluid communication with the inner fluid communication path 168 of the female coupling member 158. In this way, a second fluid, such as water or other hydration liquid, may flow freely through a second fluid communication channel 169—that includes the inner fluid communication paths 140, 168 of the magnetic quick connect 106—to communicate the hydration liquid from a source (e.g., second fluid source 122) to the headgear assembly 102.

The male and female coupling members 130, 158 of the magnetic quick connect 106 may be configured to permit a user 126 to couple and uncouple the coupling members 130, 158 and their associated components with a single hand and without actually viewing the coupling members 130, 158 when they are to be coupled together or uncoupled. For example, the male and female coupling members 130, 158, may be configured so that magnetic force of attraction between the two coupling members 130, 158 is such that the user 126 need only bring the two coupling members into proximity with (although not necessarily even touching) one another and the magnetic force of attraction between the two coupling members 130, 158 will automatically align and couple the members 130, 158 together in a fluid tight manner. As a result, user 126 need not be able to visualize the male and female coupling members 130, 158 of magnetic quick connect 106 when coupling or uncoupling them. Furthermore, as the strength of the magnetic force of attraction between the coupling members 130, 158 is increased, then user 126 will not need to bring the coupling members 130, 158 as close together in order for the magnetic force of attraction between the two coupling members 130, 158 to automatically align and couple the members 130, 158 together in a fluid tight manner.

The user 126 can also rely on the haptic feedback provided by the magnetic force of attraction between the two coupling members 130, 158 to know when he or she has brought female coupling member 158 sufficiently close to, and sufficiently aligned with, male coupling member 130 so as to release female coupling member 158 and allow the magnetic force of attraction between the two coupling members 130, 158 to finish aligning and coupling the members 130, 158 together in a fluid-tight manner. The strength of the magnetic force of attraction between the two coupling members 130, 158 can also be set so that when the two coupling members 130, 158 couple together as a result of the magnetic force of attraction that a distinct, audible noise, such as an audible "clacking" noise, will be made due to the two coupling members coming together in a fluid-tight manner. As a result, user 126 can listen for the clacking or other distinct noise to verify that coupling members 130, 158 have been properly coupled together in a fluid-tight manner without ever visualizing the two coupling members when coupling them together.

Furthermore, the inclusion of a magnetic quick connect 106 in the fluid delivery path of fluid delivery system 101 also substantially increases the safety of fluid delivery system 101 over conventionally known hydration system designs for a wide variety of uses or applications. For example, while the male and female coupling members 130, 158 may be configured so that magnetic force of attraction between the two coupling members 130, 158 is sufficient to automatically align and couple the members 130, 158 together when they are brought into proximity to one another, the force of attraction may also be set so that the amount of force required to disconnect the male and female coupling members 130, 158 is such that the coupling members will disconnect without injuring the user 126 in the event that a portion of the tubing 114 is subjected to a force while the user 126 is operating the vehicle 128. Similarly, in the event the user 126 crashes the vehicle 128 or some other emergency occurs that requires user 126 to exit the cabin of the vehicle 128 quickly, the male and female coupling members 130, 158 will easily and automatically disconnect as the user 126 removes himself from the vehicle 128, or the user 126 is extracted from the vehicle 128 by a race track crew. These safety features may be particularly important in the event of a fire within the cabin of the vehicle 128 or a spinal injury to the user 126.

The magnetic force of attraction between coupling members 130, 158 may be increased, for example, by (i) increasing the thickness of the first and/or second magnetic materials 142, 170; (ii) increasing the cross-sectional area of the pole of the first and/or second magnetic materials 142, 170 that faces the other magnetic material ("the mating cross-sectional area"); (iii) increasing the flux density (B) and/or magnetization (M) of the first and/or second magnetic material 142, 170; and/or (iv) decreasing the thickness and/or magnetic permeability ($\mu$) of any non-magnetic material between the first and second magnetic materials 142, 170 and the mating surfaces of mating ends 134, 162 of male and female coupling members 130, 158, respectively. Conversely, the magnetic force of attraction between coupling members 130, 158 may be decreased, for example, by adjusting parameters (i)-(iv) in the opposite direction.

In some approaches, an axial pull force that is greater than 48 ounce-force and less than 128 ounce-force between the male coupling member and female coupling member is required to decouple the male and female coupling members. In other approaches, an axial pull force that is greater than 64 ounce-force and less than 96 ounce-force between the male coupling member and female coupling member is required to decouple the male and female coupling members. In still other approaches, an axial pull force that is greater than 72 ounce-force and less than 88 ounce-force between the male coupling member and female coupling member is required to decouple the male and female coupling members.

Referring again to FIG. 1, the vehicle 128 may be provided with a magnetic quick connect holder 202. The magnetic quick connect holder 202 is preferably located in the vehicle 128 near a user's head (e.g., at the roof or side wall of the vehicle). The magnetic quick connect holder 202 is preferably sized to receive the female coupling member 158. Similar to the male coupling member 130, the magnetic quick connect holder 202 includes a first magnetic material for magnetically coupling with the female coupling member 158. In this way, upon disconnecting the female coupling member 158 from the male coupling member 130, the user 126 can securely couple the female coupling member 158 to the magnetic quick connect holder 202 mounted to vehicle 128 to keep the upstream portions of the magnetic quick connect 106 (and the upstream portions of fluid delivery system 101 connected thereto) readily available for the next use. Because the female coupling member 158 is maintained in a consistent, accessible manner, the magnetic quick connect holder 202 permits quick driver departure and arrival as may be required, for example, during driver changes or when a driver intends to perform maintenance on the vehicle 128. Furthermore, by securing the female coupling member 158 to the magnetic quick connect holder 202 between uses, the inner and outer fluid communication paths 168, 166 of the female coupling member 158 are effectively sealed off. In this way, dust, debris, and gasses are inhibited from entering the hose side connector 158 of the magnetic quick connect 106 between uses.

In other approaches, the female coupling member 158 may be adapted to be secured directly to the vehicle 128. This may be the case, for example, when the vehicle 128 includes a magnetic surface, such as the interior surface of a metal roll cage.

As shown in FIG. 1, the hydration and air cooling system 100 includes a second fluid source 122 for communicating a fluid to the fluid delivery system 101. The second fluid source 122 preferably comprises a potable liquid such as water or other hydration liquid, and may include a reservoir to store the potable liquid and a pump to move the potable liquid through the tube fluid delivery system 101 to the user 126. In this way, the hydration and air cooling system 100 includes a hydration subsystem that supplies a drinkable liquid to the user 126. As described in greater detail elsewhere herein, the hydration subsystem includes hydration fluid delivery or input tube 110 and headgear assembly 102, which includes mouthpiece assembly 112 supported within the helmet 103 proximate to the user's mouth. The mouthpiece 112 of headgear assembly 102 is connected in fluid communication with the second fluid source 122 via magnetic quick connect 106 and input tube 110.

In the illustrated embodiment, hydration input tube 110 includes tube conduit 110a, tube conduit 110b, and the secondary fluid channel 200 in splicer 108, which connects tube conduits 110a, 110b in fluid communication. In other embodiments, hydration input tube 110, may include additional or fewer components that make up the fluid delivery path from the source 122 to the magnetic quick connect 106.

As shown for example in FIGS. 1, 2, 3A, and 3B, to deliver the hydration liquid (e.g., water) into a second fluid communication channel 169 disposed within a first fluid communication channel 167 defined in part by the tube 114, the fluid delivery system 101 may be provided with a splicer 108 disposed in the tube 114 between tube portions 116 and 118. Splicer 108 splices or inserts the second fluid communication channel 169 within the first fluid communication channel 167. As a result, the second fluid communication channel 169 extends within, or internal to, the first communication channel 167 from the splicer 108 downstream to at least the helmet interface 104 of headgear assembly 102.

Referring now to FIGS. 8A-8D, the splicer 108 includes a splicer body 188. The splicer 108 may further include a first splicer clamp 190 and a second splicer clamp 192. Similar to the adjustable clamp portions 136, 164 of the magnetic quick connect 106, one or both of the first splicer clamp 190 and the second splicer clamp 192 may take the form of a "C-clamp", and may be removably connectable to the splicer body 188, for example, through the use of screws or other fastening devices. In this way, the first and second splicer clamps 190, 192 allow the splicer 108 to be secured to tubing; for example, tubing portions 116 and 118, respectively. In an exemplary use, a user may remove the splicer clamp portion 190 and position a tubing portion 116 adjacent splicer body 188. The user then reconnects the first splicer clamp 190 to the splicer body 188, thereby securing the tubing portion 116 to the splicer body 188. Similarly, a user may remove the second splicer clamp 192 and position a tubing portion 118 adjacent splicer body 188. The user then reconnects the second splicer clamp 192 to the splicer body 188, thereby securing the tubing portion 118 to the splicer body 188. Other suitable mechanisms and fastening devices for securing tubing to the splicer body 188 are expressly contemplated herein.

In some approaches, the splicer body 188 and splicer clamp portions 190, 192 form a plurality of ridges and grooves. The ridges and grooves may form, for example, one or more threaded regions. The one or more threaded regions may, for example, be adapted to receive tubing portions 116 and 118. In this way, the splicer clamp portions 190, 192 may be adapted to secure the tubing portions 116 and 118 to the splicer 108 via compression and friction fit forces without the need to rotate the tubing portions 116 and 118 relative to the splicer 108.

The splicer 108 defines an outer fluid communication path 194. The outer fluid communication path 194 is adapted to communicate a fluid from the first tubing portion 116 to a second tubing portion 118. For example, the splicer 108 may receive an airflow from a first tubing portion 116, and may communicate the airflow to a second tubing portion 118.

The splicer 108 may further include a secondary fluid inlet 196, a secondary fluid outlet 198, and a secondary fluid channel 200 fluidly connecting the inlet 196 with the outlet 198. Secondary fluid inlet 196 may include a hose connector such as a barbed hose connector 197 for connecting to a portion of hydration input tube 110, namely tubing conduit 110a, which is upstream of secondary fluid channel 200. The fluid flow may be passed through the secondary fluid outlet 198 to the secondary fluid outlet 198. The secondary fluid outlet 198 may similarly include a hose connector, such as a barbed hose connector 199 for connecting to tube 110b connected at one end to the secondary fluid outlet 198 and at its other end to the barbed hose connector 181 provided on the upstream end of inner member 180 of the female coupling member 158.

In some approaches, the hydration and air cooling system 100 may also include an auxiliary communication system, including audio source 124. Depending on the application, audio source 124 may, for example, comprise an intercom or two-way radio. Similar to how the second fluid communication channel 169 is introduced into the first communication channel 167 by splicer 108, one or more wires—for connecting a microphone and/or speakers of the auxiliary communication system to the audio source 124 of the auxiliary communication system—may also be introduced to the first fluid communication channel 167 of the fluid delivery system 101 at the splicer 108, or at another splicer provided in the fluid delivery system 101. The auxiliary communication system may include electrical wiring to provide electrical power to downstream components such as the microphone 254 included in mouthpiece assembly 112 and/or speakers included within helmet 103. The auxiliary communication system may also or instead provide an audio communication link to downstream components such as the microphone 254 included in mouthpiece assembly 112 or speakers. Alternatively, as is conventional, the art, wiring of the auxiliary communication system may be disposed entirely outside of the tubing 114 of the fluid delivery system 101. For example, as illustrated in FIG. 13, the applicable wiring for microphone 254 and helmet speakers of the auxiliary communication system may be introduced to helmet 103 at the bottom of the helmet between the helmet foam and wall of the helmet 103. As described in greater detail below, the microphone boom 267 of such auxiliary audio systems may be used not only to support microphone 254 of the auxiliary audio system, but it may also be used to support the mouthpiece assembly 112 of the hydration subsystem of the fluid delivery system 101.

Figure 9:
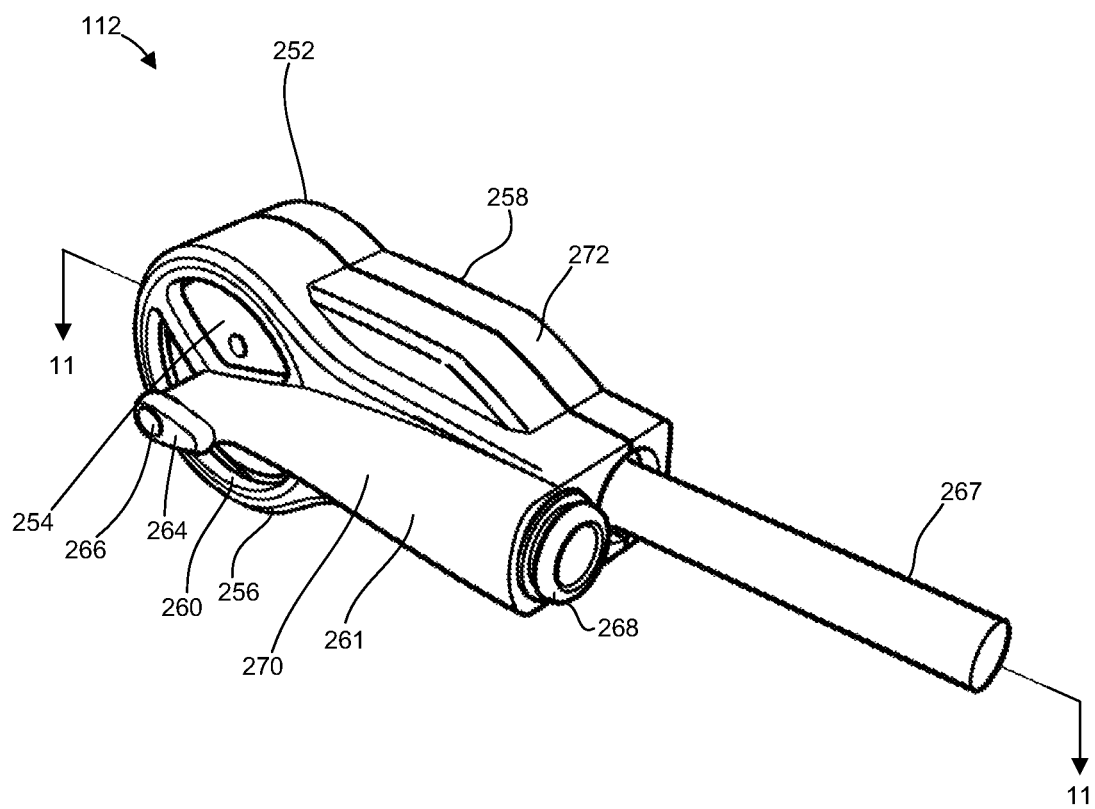
FIG. 9 is a perspective view of a mouthpiece assembly for use with a fluid delivery system of a hydration system.

FIG. 9 illustrates an example mouthpiece assembly 112. As illustrated in FIGS. 1 and 2, mouthpiece assembly 112 may be used in headgear assembly 102 of the hydration and air delivery system 100. In addition, however, mouthpiece assembly 112 may be used with other headsets that include a microphone disposed at the end of a support member, such as a microphone boom.

Figure 11:
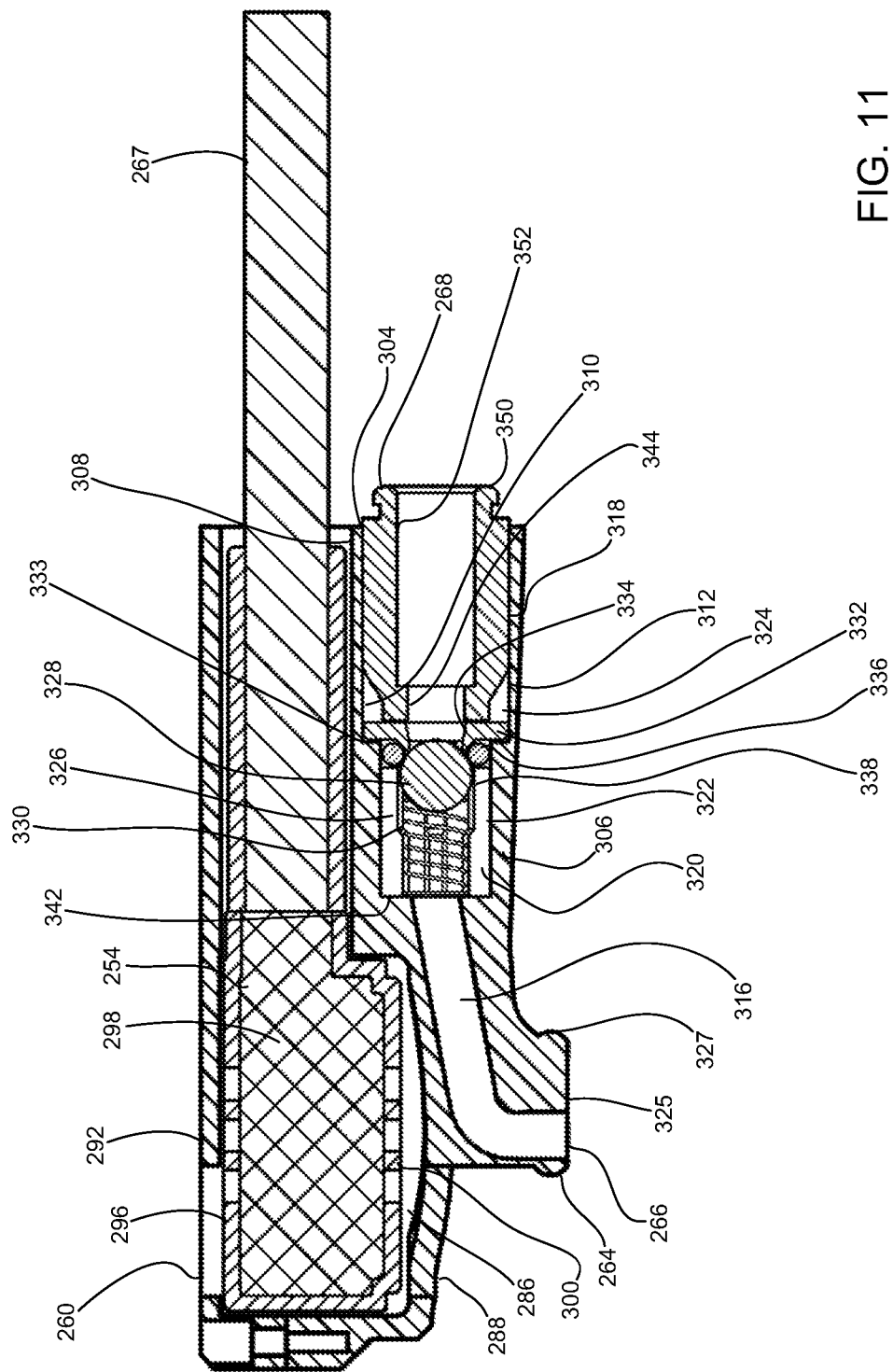
FIG. 11 is a cross-sectional top view of the mouthpiece assembly of FIG. 9 taken along cutline 11-11.

The mouthpiece assembly 112 is configured to permit audio communication from and the delivery of drinkable fluids to the user 126. To provide these functionalities, a microphone 254 is disposed at the end of a support member or microphone boom 267. A conduit 261 defining a fluid passageway 316 (as best seen in FIG. 11) is also supported by the support member 267. A mouthpiece 264 is provided at the distal end of the passageway 316 so as to be positioned in front of the microphone 254. The mouthpiece includes an outlet port 266 that is in fluid communication with the fluid conduit 261. A hose connector 268 may be provided at the proximal end of the fluid passageway 316 to connect to the fluid-delivery tube 111 shown in FIG. 2A.

Figure 10:
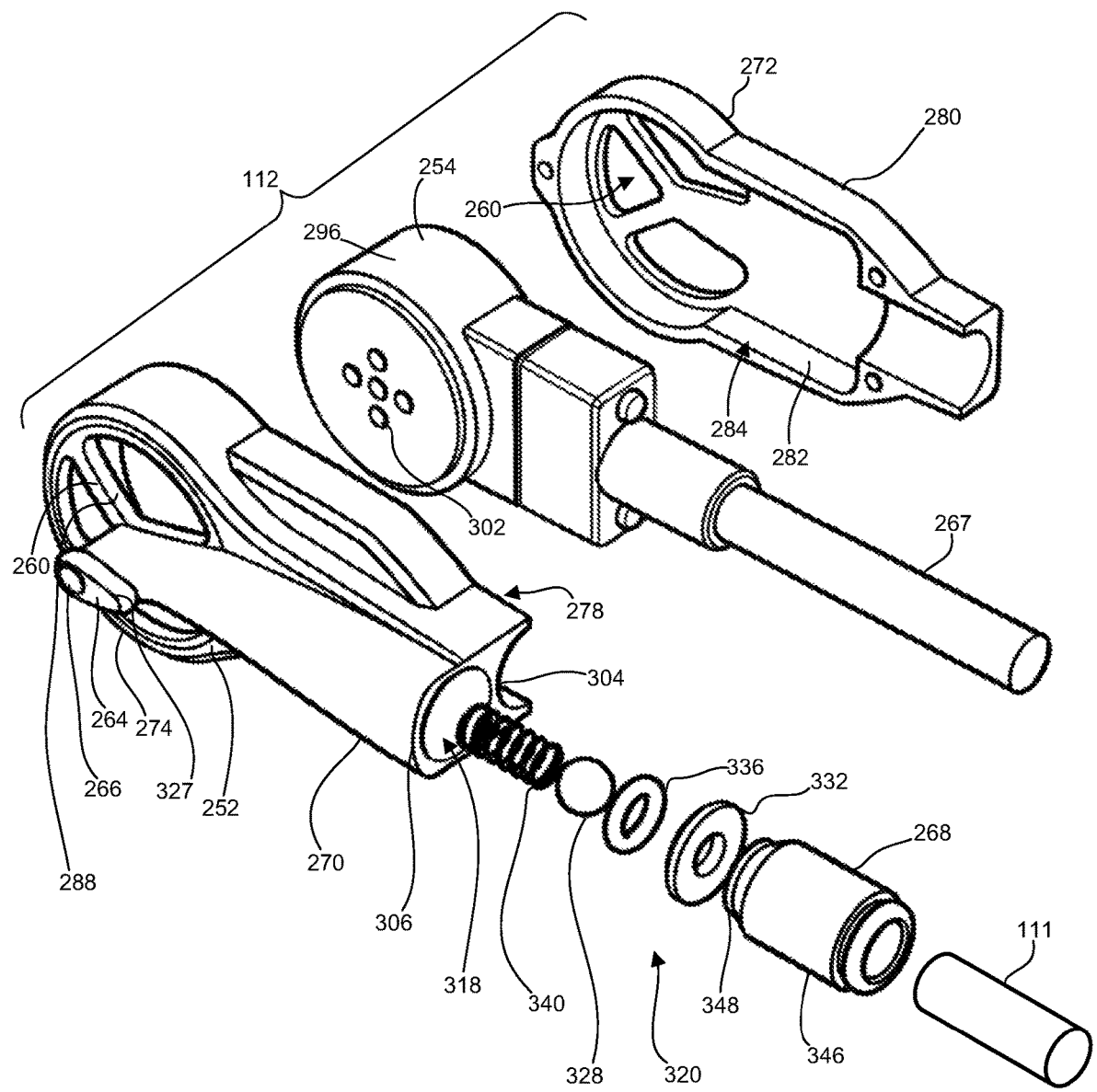
FIG. 10 is an exploded perspective view of the mouthpiece assembly of FIG. 9.

The mouthpiece assembly 112 may include a microphone case 252 that defines a microphone cavity for receiving microphone 254 therein. The microphone case 252 illustrated in FIG. 9 encases microphone 254. The case 252 of the present embodiment is formed from two halves: a front half 270 defining a front side 256 of the case that is intended to face the user 126 during use and a back half 272 defining a backside 258 of the case. The front half 270 defines a recessed area 278 and the back half 272 defines a recessed area 284 that cooperate with each other to form the microphone cavity when the halves are assembled to the microphone 254 as shown in FIG. 10. The front side 256 and backside 258 may include a plurality of openings 260 allowing sound to freely travel through the case 252 and into the microphone 254.

The microphone case 252 is supported on the support member 267. The fluid conduit 261 and the fluid supply passageway 316 it defines are in turn attached to the microphone case 252. The fluid conduit is configured to supply a drinkable fluid to the user 126. The conduit 261 may be integrally formed with the case 252, or may be a separate component attached to an outer surface of the case 252. In other approaches, however, the fluid conduit 261 and the passageway 316 it defines may be attached directly to the microphone 254 and/or support member 267.

The distal end of the fluid conduit 261 may include an integrally formed mouthpiece 264 or a separate mouthpiece. The mouthpiece is preferably disposed on the front side 256 of case 252 at a distal end of the conduit 261 so that it is positioned adjacent to and in front of microphone 254. The mouthpiece includes an outlet 266 that is in fluid communication with passageway 316 so as to be able to supply fluid to a user's mouth. As best seen in FIG. 2, fluid is supplied to the mouthpiece assembly 112 by a tube 111 that is connected at is distal end to a hose connector 268 provided at the proximal end of conduit 261. The proximal end of tube 111 may be connected to a hydration reservoir (e.g., source 122) as described above via magnetic quick connect 106 and one or more other sections of tubing and/or fluid conduits making up hydration input conduit 110.

The mouthpiece assembly 112 is disposed on a distal end of a support member 267 (also known as a microphone boom). A proximal end of the support member 267 is preferably connected to or configured to connect to headgear such as a helmet or head bracket. Support member 267 is preferably flexible in order to permit user 216 to adjust the position of the mouthpiece assembly so that it is disposed in front of his or her mouth when wearing headgear to which it is attached. Flexible support member 267 will be described in more detail below.

Referring to FIGS. 10 and 11, the front half 270 and a back half 272 of case 252 may sandwich the microphone 254 when assembled together. The halves may be secured together by fasteners, adhesive, clips, or other means known in the art. In other embodiments, the case 252 may be formed by more than two components that are assembled together. For example, the mouthpiece assembly 112 may include three or more components that are assembled together to form the case 252 and/or conduit 261.

The front half 270 may include a front face 274 and one or more sidewalls 276 extending substantially perpendicular from the front face to define the recessed area 278. The back half 272 may include a back face 280 and one or more sidewalls 282 extending substantially perpendicular from the back face to define the recessed area 284. The front face 274 may include a generally planar portion 288 that defines one or more openings 260 to permit sound to travel through the case 252 and into the microphone 254. Similarly, the back face 280 may include a generally planar portion 292 that defines one or more openings 260. The planar portions 288 and 292 may be shaped to match the shape of the microphone 254. The microphone 254 may include a housing 296 that houses the microphone electronics 298. The housing 296 may include opposing faces 300, which may be planar. One or both of the faces 300 may define one or more sound receiving holes 302 allowing soundwaves to reach the electronics 298 with less obstruction. In the illustrated embodiment, the faces 300 are circular. The planar portions 288, 292 of the case 252 may also be circular to match the shape of the microphone housing 296. Of course, the microphone 254 and case 252 may be other shapes in different embodiments.

The front half 270 may include an internal wall 304 and an external wall 306 that are spaced apart from each other. The distance between the internal wall 304 and the external wall 306 may vary along a length of the first half 270. A first surface 308 of the internal wall 304 cooperates with the sidewalls 276 to define the front receiving area 278. A second surface 310 of the internal wall 304 cooperates with the interior surface 312 of the external wall 306 to at least partially define the fluid passageway 316.

In one or more embodiments, each of the housing halves 270, 272 may be formed as a single-piece assembly with many of the above described features being integrally formed. The halves may be formed of metal, plastic, or a composite. They may also be machined, cast, injection molded, or 3-D printed. The manufacturing technique employed may dictate, however, the number of parts required to form the front half 270 and back half 272.

The fluid conduit 261 defines the fluid supply passageway 316 of the case 252 that conveys fluid from the tube 111 to the outlet 266 of mouthpiece 264. In one or more embodiments, the fluid passageway 316 includes a valve chamber 318. A valve 320 is disposed in the valve chamber 318. The valve 320 may be a check valve that permits fluid above a predetermined cracking pressure to flow to the outlet 266 of mouthpiece 264. On the other hand, when the pressure in tube 111 drops below the cracking pressure of the valve 320, fluid is prevented from flowing from the mouthpiece back towards the source 122 through tube 111. In addition, because air is prevented from entering tube 111 by valve 320, the hydration fluid pumped from source 122 and filling tube 111 will remain in tube 111 even when the pump is not energized, thus limiting the time to deliver fluid to outlet 266 the next time the pump in source 122 is energized. Further, because valve 320 is located proximate mouthpiece 264 it also helps limit the amount of hydration liquid that may flow out of the outlet 266 when the fluid pressure is below the threshold cracking pressure in tube 111.

The valve 320 includes a closing member biased, by a biasing member, to seat against a sealing surface so that fluid is inhibited from flowing to the mouthpiece when fluid pressure is below the threshold. The biasing force of the biasing member is sized or chosen so that the closing member disengages with the sealing surface in response to the pump of source 122 being energized. However, valve 320 is not limited to a valve having this structure and any check-valve, one-way valve or two-way valve exhibiting the cracking pressure characteristics described above may also be used.

The valve 320 may be a ball-type check valve. The valve chamber 318 may generally include a first portion 322 and a second portion 324 having a diameter larger than the first portion. The first portion 322 may include a ball guide having a plurality of projections 326. A check ball 328 of the valve 320 rides on the projections 326. Each of the projections may define a stopper 330 that prevents the check ball 328 from moving too far in the downstream direction. Excessive upstream movement of the check ball 328 is prevented by an annular plate 332. The annular plate 332 is disposed in the second portion 324 and is seated against a first shoulder 333. The annular plate 332 defines an inner bore that permits fluid to pass therethrough. The inner bore defines an inlet 334 of the valve 320. A sealing member 336, such as an O-ring or a gasket, is disposed between the check ball 328 and the annular plate 332. The sealing member 336 is seated against the tips 338 of the projections 326. A biasing member 340, such as a coil spring, urges the check ball 328 against the sealing member 336 to close the inlet 334. The biasing member 340 may be seated against a second shoulder 342. The biasing member is configured to firmly seat the ball 328 against the O-ring 336 when fluid pressure is below the threshold cracking pressure, and to allow the ball 328 to displace in the downstream direction allowing fluid to through the mouthpiece 264 when the fluid pressure is above the threshold.

Hose connector 268 connects the fluid supply passageway 316 of mouthpiece assembly 112 to the tube 111. The connector may be a female fitting or a male fitting. In the illustrated embodiment, the connector is a female fitting. The female fitting 268 may be received within the passageway 316 with an outside surface 346 engaging the walls of the passageway 316 and with a front end 348 disposed against the annular plate 332. The front end 348 includes a bore defining an inlet 344 to passageway 316. The rear end 350 of the fitting 268 may extend out of the passageway 316. The fitting 268 may be a quick-connect fitting (also known as a push-to-connect fitting) having an inside surface 352 that defines a bore for receiving the tube 111 therein. The fitting 268 includes features disposed within the bore that grip the tube 111 preventing the tube from being inadvertently removed from the fitting. The fitting 268 may include a release collar allowing the tube 111 to be removed from the fitting 268.

In the present embodiment, the front half 270 defines the fluid passageway 316 that extends from the outlet 266 of mouthpiece 264 to the inlet 344 defined in front end 348 and includes the valve chamber 318 disposed therein. The mouthpiece 264 extends generally away from the planar portion 288 and is located adjacent to the microphone 254. In one or more embodiments, the mouthpiece 264 is disposed within a perimeter of the front face 300. The mouthpiece 264 may include a raised ring 327 disposed around the tip 325. The raised ring 327 is ergonomically shaped to engage with a user's lips.

In one or more embodiments, the case 252 may only include one of the halves, which is attached to either the front side, the back side, or other portion of the microphone housing 296. For example, mouthpiece assembly 112 could only include the front half 270. The front half 270 may be connected to the microphone housing 296 by clips, fasteners, tape, or adhesives. The clips may be integrally formed features of the front half, the housing 296, or both.

The microphone 254 is disposed at the end of the flexible support member 267 and sometimes the two are provided as a unit together. An end portion of the flexible support member is disposed within the housing 296 of microphone 254. The housing 296 may define an opening for receiving the support member 267. The electrical wires of the microphone 254 may extend through the support member 267 and the housing 296 to connect to the microphone electronics 298. The support member 267 may include a sleeving that surrounds the microphone wires, such as a heat shrink tubing. The support member 267 may also include one or more stiffing elements internal to the sleeving or external to the sleeving. The stiffing element should be sufficiently stiff to hold the mouthpiece in place once positioned, yet sufficiently flexible to allow the position of the mouthpiece to be modified relative to the headgear so that a user can place the mouthpiece assembly 112 in a desired location. The stiffening element may also work in combination with the sleeving to provide this functionality. The stiffing element may allow the support member 267 to be bent, curved, or otherwise positioned between at least a first position and a second position, and is operable to hold the support member in the position. The stiffing element may comprise spiral wrap tubing formed of metal, plastic, or other material. The spiral wrap tubing may be disposed outside the sleeving, inside the sleeving, or may form the sleeving.

Figure 12:
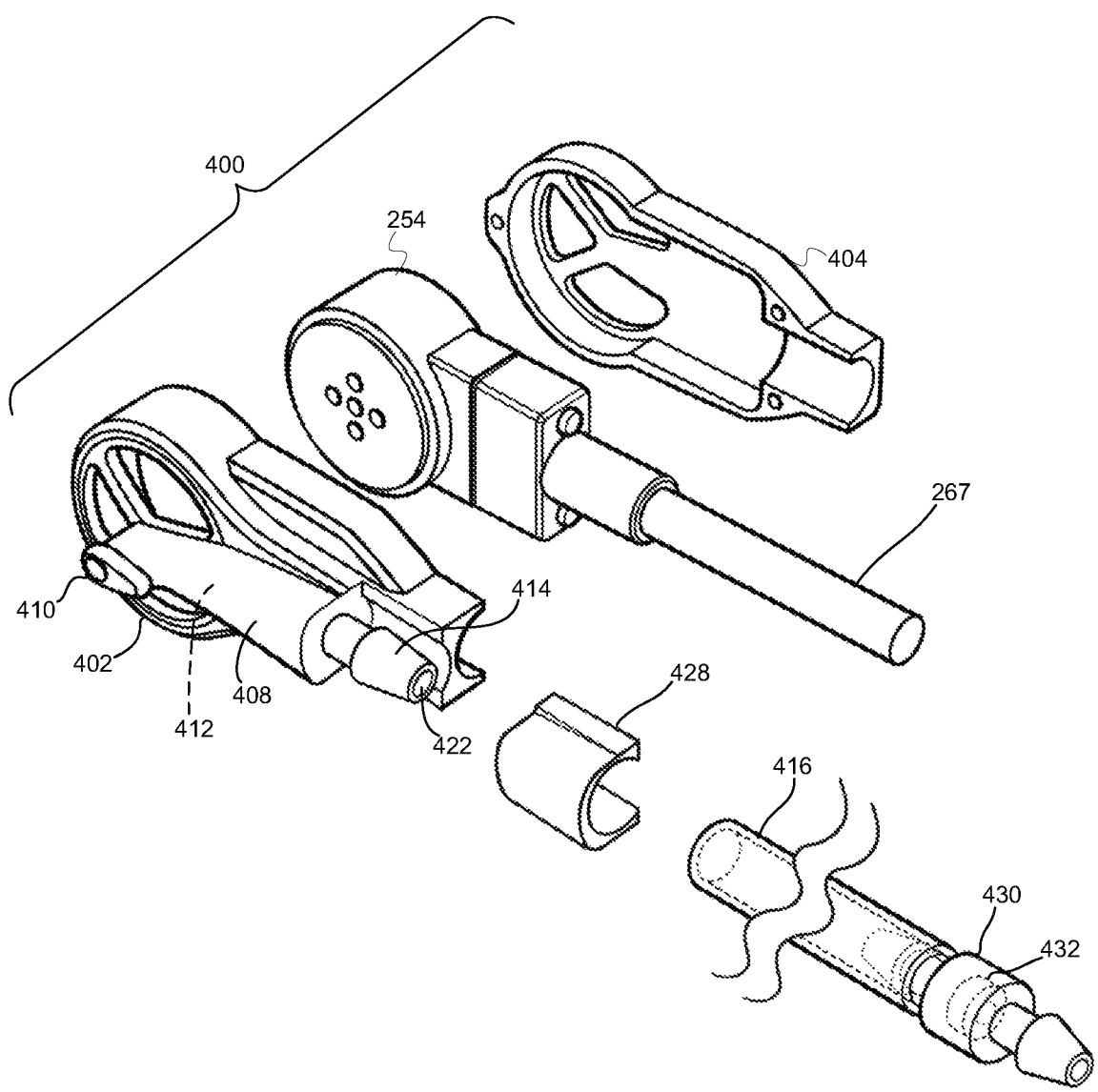
FIG. 12 is an exploded perspective view of another mouthpiece assembly for use with a fluid delivery system of a hydration system.

FIG. 12 illustrates a mouthpiece assembly 400 according to an alternative embodiment. Many features of the mouthpiece assembly 400 are similar to the mouthpiece assembly 112 and may not be described again here. Similar to the above embodiments, a front cover 402 may cooperate with a back cover 404 to encase a microphone 254 within a microphone receiving area. Alternatively, the back cover may be omitted and only the front connects to the microphone 254. The front cover 402 supports a fluid supply conduit 408. The fluid supply conduit 408 may be integrally formed with the front cover 402, or may be a separate component attached to an outer surface of the front cover or directly to the microphone 254. The fluid supply conduit 408 includes a mouthpiece 410 disposed at its distal end of the fluid supply conduit 408. Preferably the mouthpiece 410 extends from an outer surface of the front cover 402 proximate to the microphone 406. Fluid is supplied to an outlet of the mouthpiece 410 by a passageway 412 defined within the fluid supply conduit 408 and that has an inlet 422. The passageway 412 may thus be defined within the front cover 402 similar to passageway 316 of mouthpiece assembly 112. A connector 414 may be provided at the proximal end of the fluid passageway 412 to connect the fluid supply conduit 408 to a fluid-delivery tube, such as fluid delivery tube 416 or fluid delivery tube 111 of fluid delivery system 101. The connector 414 may be an integrally formed feature of the front cover 402, or maybe a separate component that attaches to the front cover. For example, the connector 414 may include threads that screw into a tapped hole of the cover 402.

In the illustrated embodiment, the connector 414 is a male connector receivable within the inside diameter of the tube 416. Preferably connector 414 is a barbed hose connector, but any suitable connector may be used. A clip 428 may be inserted over the tube to further secure the tube 416 to the connector 414 or for simply aesthetics reasons. The clip 428 may be a C-clip formed of a resilient material, e.g., spring steel or plastic that compresses the tube onto the connector 414.

Mouthpiece assemblies 112 and 400 are not limited to the illustrated connectors. Many different types of fluid connectors are known in the art and may be used to connect the fluid supply passageways provided in the mouthpiece assemblies in fluid communication with a fluid-supply tube.

A valve 430 may be provided to prevent fluid from leaking from the mouthpiece 410. Valve 430 should be disposed at a location as close as possible to mouthpiece assembly 400 to minimize the amount of water that may drip from the outlet of mouthpiece 410. The valve 430 may be disposed within the fluid passageway 412 of mouthpiece assembly 400 or may be interposed in the fluid delivery path external to the mouthpiece assembly. In the illustrated embodiment, the valve 430 is external to the mouthpiece assembly 400 and is provided at a proximal end of the tube 416. The other end of valve 430 may, for example, connect to fluid delivery tube 111 of fluid delivery system 101. The valve 430 may include a displaceable valve-closing member 432 biased to seat against a sealing surface. The valve 430 may be a check valve such as a ball check valve similar to ball check valve 320 or may be any other type of check valve, a one-way valve, or two-way valve that provides a threshold cracking pressure suitable for the fluid delivery system of the hydration subsystem.

Figure 13A:
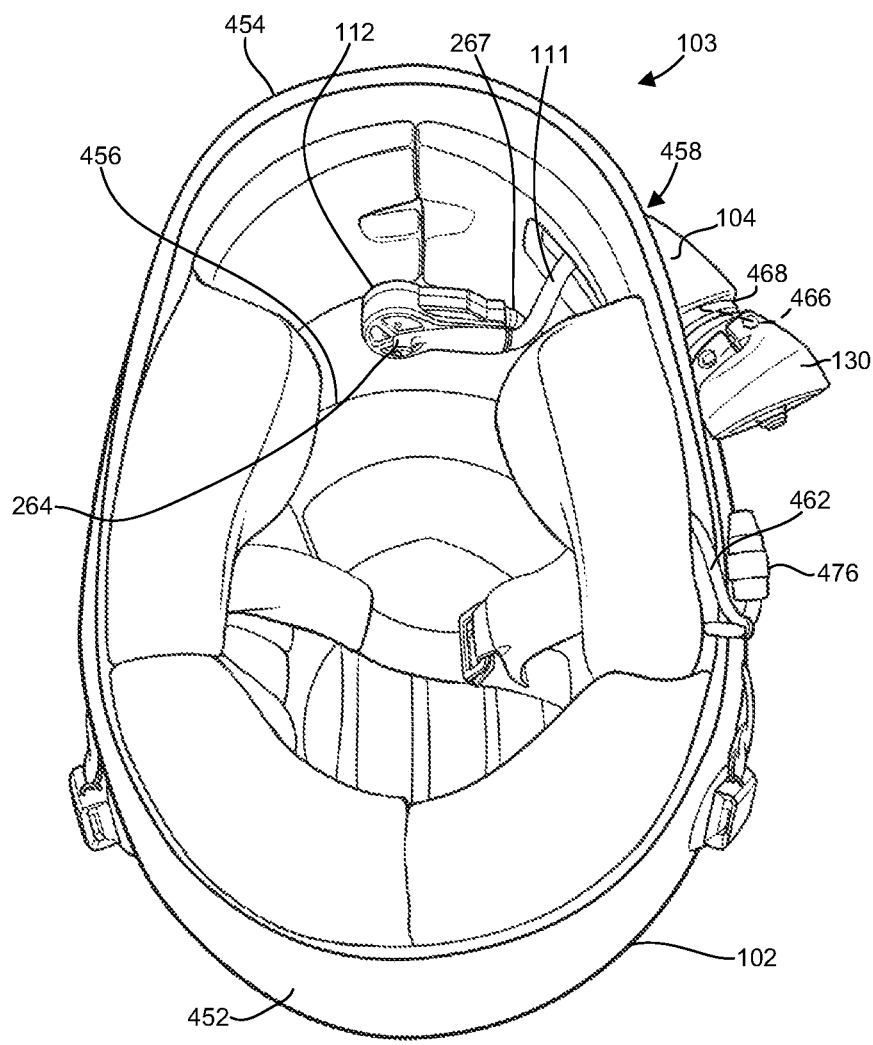
FIG. 13A is a bottom plan view of a headgear assembly including a helmet and a mouthpiece assembly.
Figure 13B:
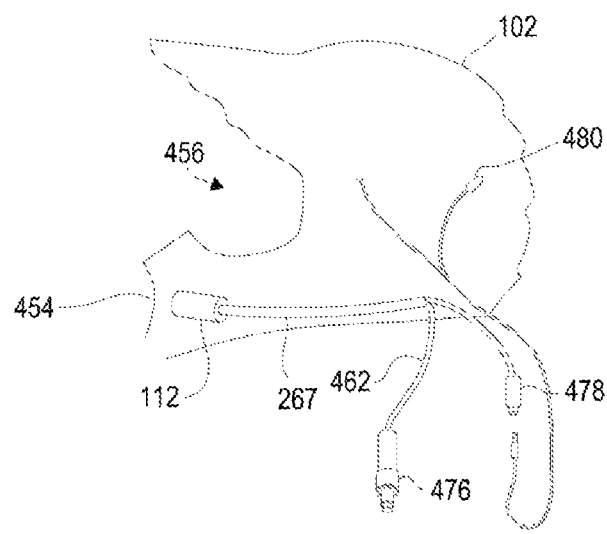
FIG. 13B is a schematic illustration of audio equipment of the headgear assembly of FIG. 13A.

Referring to FIGS. 13A and 13B, the combined fluid and audio delivery system may be integrated with headgear such as helmet 103 to form a headgear assembly 102. The helmet 103 may be a closed-face helmet having a shell 452 with a chin guard 454. The chin guard 454 cooperates with the main portion of the helmet to define an eye port 456. The helmet 1403 may include a see-through shield (not shown) pivotable to cover the eye port 456.

The helmet 103 may define a port 458 at interface 104 that provides fluid communication between the interior of helmet 103 and the primary fluid delivery tube 114 when the male coupling member 130 is coupled to the female coupling member 158 of magnetic quick connect 106 so as to form hydration and air delivery system 100. In this way, cooling and/or breathable air may be provided from source 120 to the interior of helmet 103 through port 458 by tube 114. The port 458 also allows input tube 111 of the hydration and air delivery system 100 to extend therethrough and connect to the connector 268 of mouthpiece assembly 112 at one end while also being connected to the inner communication path 140 of male coupling member 130 at inner member 148 at the other end. In this way, a hydration fluid, such as water, may be delivered from source 122 through tube 110a, splicer 108, tube 110b, the inner fluid communication paths 140, 168 of magnetic quick connect 106, tube 111, and fluid passageway 316 to outlet 266. Thus, as more fully explained below, user 216 may drink hydration fluids from outlet 266 of mouthpiece 264 when desired.

In some approaches, the port 458 may also permit the audio delivery system to be received within the interior of the helmet 103. In the illustrated embodiment, for example, an audio cord 462 enters the helmet under a bottom edge of the helmet 103, but in other embodiments, the audio cord 462 may enter the helmet through the port 458. The port 458 is provided in the chin guard 454 of helmet 103 in the embodiment shown in FIG. 13, but in the embodiment illustrated in FIG. 3B, port 458 would be located on the top of helmet 103. Other locations are also possible. The port 458 may be an opening defined through the shell and the padding at the desired location. A helmet interface 104 may be disposed on the helmet so as to be in fluid communication with the port 458 and cover the port 458.

In some embodiments, the interface 104 is a separate component connected to the helmet 103, such as at chin guard 454, by fasteners or clips to cover the port 458. In other embodiments, at least portions of the interface 104 are formed integral with the shell 452 of helmet 103.

FIG. 13B further illustrates one possible positioning of the mouthpiece assembly 112, support member 267, and the associated audio system within helmet 103. For sake of clarity other aspects of fluid delivery system 101 are omitted from FIG. 13B.

Referring to FIG. 13B, mouthpiece assembly 112 is supported on the distal end of support member 267 within the helmet 103 behind the chin guard 454 to position the mouthpiece assembly 112 in front of a user's mouth. The mouthpiece assembly 112 is arranged within the helmet 103 so that the outlet 266 of mouthpiece 264 is directed toward or faces the user as shown in FIG. 13A. The support member 267 is attached to an interior wall of shell 452 using adhesive or other suitable fasteners as is conventional in the art. Microphone cord 462 extends through the support member 267 to the microphone 254 in mouthpiece assembly 112. The support member 267 and microphone cord may be integrally formed or the support member may be wrapped around the microphone cord. As described above, the support member 267 is a stiff, yet flexible component that holds the mouthpiece assembly 112 in place while also allowing the mouthpiece assembly 112 to be repositioned to a position that is most comfortable for the user.

Once support member 267 is suitably connected to the interior wall of shell 452 an audio jack 476 may be provided on the helmet 103 to electrically connect the microphone to the audio system 124 via the cord 462. The audio jack 476 includes sufficient contacts to also allow earphones or ear buds having speakers 480 to be plugged into an earphone jack 478 that is electrically connected to audio jack 476. When audio jack 476 is mated with a connector of a second audio cord that is connected to audio system 124, which may, for example, comprise a transceiver or intercom, user 126 may communicate with and hear others (such as passengers and/or crew members) that are also connected to audio system 124. The speaker 480 may be connected to the helmet, or may be a personal speaker, e.g., head phone or ear bud, worn by the user.

It is to also be understood that any of the above described mouthpiece assemblies may be utilized in hydration systems with a wide variety of headgear that is suitable to support the mouthpiece assembly proximate to a user's mouth. The headgear may include, for example, any of a variety of conventional headsets that include a microphone boom extending from a head bracket. However, the support structure of the described mouthpiece assemblies may also be connected to or supported by a wide variety of other headgear. For example, in some embodiments, the headgear may comprise safety headgear, such as a helmet or hard hat. In other embodiments, the headgear may comprise other common headgear such as, for example, a hat, head bracket, or any other garment or device intended to be worn on a person's head. When the applicable headgear is safety headgear, the support structure may be configured to attach to the safety headgear, it may already be attached to the safety headgear, or at least a portion of the support structure may be formed integral with the safety headgear. Further, a headset of the present patent document may be attached to, or integrated with, any type of helmet, including, for example, motorcycle helmets (half, three quarter, open face, and full face), auto racing helmets, cycling helmets, snowboarding and skiing helmets, mountain climbing helmets, military and other tactical helmets, fire helmets, safety helmets, and rescue helmets. Furthermore, as will be appreciated from the disclosure below, the mouthpiece assemblies described herein may be used in hydration systems that do not also provide air to the user as does system 100.

Figure 14:
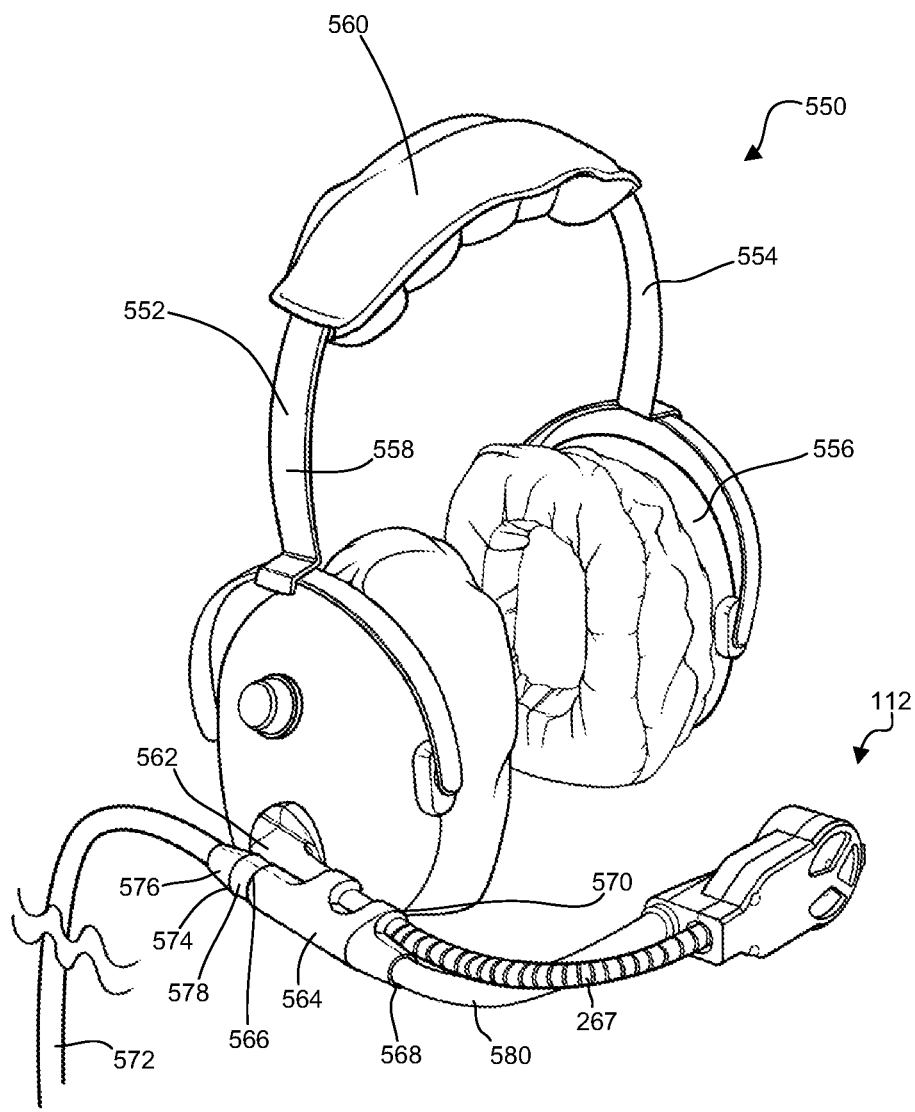
FIG. 14 illustrates a perspective view of another headgear assembly including a headset and a mouthpiece assembly.

Referring to FIG. 14, in one or more embodiments, the mouthpiece assembly 112 is utilized with a headgear 550 adapted to be worn on a user's head. The headgear 550 may include a headset 552 having a head mount bracket 554 and the head mount bracket may be configured to include two opposing support members 556 connected together by a resilient U-shaped spring member 558. The support members 556 may be adapted to cup a user's ears. When the two opposing support members are pulled away from one another, the U-shaped spring member produces a biasing force that tends to bias the opposing support members in a direction toward one another. Further, the head bracket mount is preferably configured so that when it is worn on a user's head the two opposing support members contact opposite sides of the user's head. In some embodiments, the head bracket mount is configured so that when it is worn on a user's head the two opposing support members contact opposite sides of the user's head and the U-shaped spring member wraps around the base of the user's skull. The headset may also further comprise a pad 560 disposed about at least a middle portion of the U-shaped spring member.

The boom 267 of the mouthpiece assembly 112 may be connected to one of the support members 556 by a connector 562 to attach the mouthpiece assembly 112 to the headset 552. The connector 562 may be pivotally attached to the support member 556. The connector 562 may include a tubular portion that receives a proximal portion of the boom 267 therein. The microphone wires may extend through the connector 562 and into at least one of the support members 556. Headset 552 may be wired or wireless. If wired, an audio cable with an audio plug (not shown) may extend from one of the support members 556 and be configured to connect with a conventional audio jack thereby enabling the headset 552 to be electrically connected to an audio system. One or more speakers may be provided in one or more of the support members 556.

The headset 552 is adapted for use with a hydration system including a fluid reservoir, such as source 122, via a main fluid-supply tube 572 that is in fluid communication with the fluid reservoir at a proximal end. The fluid-supply tube 572 may include multiple segments of tubing that are connected together by connectors, valves, or other hydraulic components. The headset 552 may include a support member 564 that connects the mouthpiece assembly 112 to the tube 572. In other embodiments, the tube 572 may directly connect with the connector 268 of the mouthpiece assembly 112.

The support member 564 may be supported on the connector 562 or support member 267 or both. In some embodiments, one or more portions of the support member 564 may be integrally formed with the support member 564. In other embodiments, the support member 564 and the connector 562 are separate components that are connected to each other. For example, the support member 564 may include a pair of clips 570 that define openings that receive the tubular body of the connector 562 and/or boom 267. The support member 564 has an upstream end 566 and a downstream end 568.

The upstream end 566 is connectable to the tube 572 by a conventional fitting such as a barbed hose connector or female push-to-connect connector, or by a magnetic quick connect 574 such as the magnetic quick connects described in U.S. Provisional Application 62/363,334, and U.S. application Ser. No. 15/652,847, which are incorporated by reference herein.

The magnetic quick connect 574 may, for example, include a male coupling member 576 and a female coupling member 578. It is expressly contemplated that the features described herein with respect to the male coupling member 576 and the female coupling member 578 may be incorporated in either of the male coupling member or the female coupling member. Further, the position of the male coupling member 576 and the female coupling member 578 may be reversed. Thus, for example, the coupling members of the magnetic quick connect 574 may be referred generically to as the downstream coupling member and upstream coupling member.

In the illustrated embodiment, the male member 576 is provided on the end of the tube 572 and the female member 578 is provided on the end 566 of the support member 564. In other embodiments, however, the female member 578 is provided on the tube 572 and the male member 576 is provided on the support member 564.

The male member 576 of the magnetic quick connect includes a fluid inlet port connectable to the tube 572 by a hose connector, such as a barbed hose connector or a female hose connector, formed in the male member 576. In one approach, the female member 578 includes a fluid outlet port that is in fluid communication with a fluid passageway extending through the support member 564. The downstream end of the support member 564 is connectable to a fluid delivery tube, such as tube 580 via a hose connector, such as a barbed hose connector or a female hose connector. The other end of the tube 580 is connected to the hose connector 268 of the mouthpiece assembly 112 as described above.

In the above described embodiment, support member 564 includes a fluid passageway for fluid to travel from the upstream end 566 to the downstream end 568. However, in other embodiments, the support member 564 may define a tubular cavity through which the tube 580 extends through to connect with the downstream end of female member 578. In such an embodiment, tube 580 extends through support member 564 so that its proximal end is connected to (and in fluid communication with) the female (or downstream) coupling member 578.

The male member 576 includes a fluid outlet port that connects with a fluid inlet port of the female member 578. For example, the male member 576 may have a projection that defines the fluid outlet port, and the female member 578 may have a receptacle that defines the fluid inlet port. The projection is received within the receptacle, for example as shown in FIG. 4C, and preferably with the taper angels previously described. Each of the coupling members 776 and 778 includes a magnet for selectively coupling the male member 576 to the female member 578 as described above.

Figure 15:
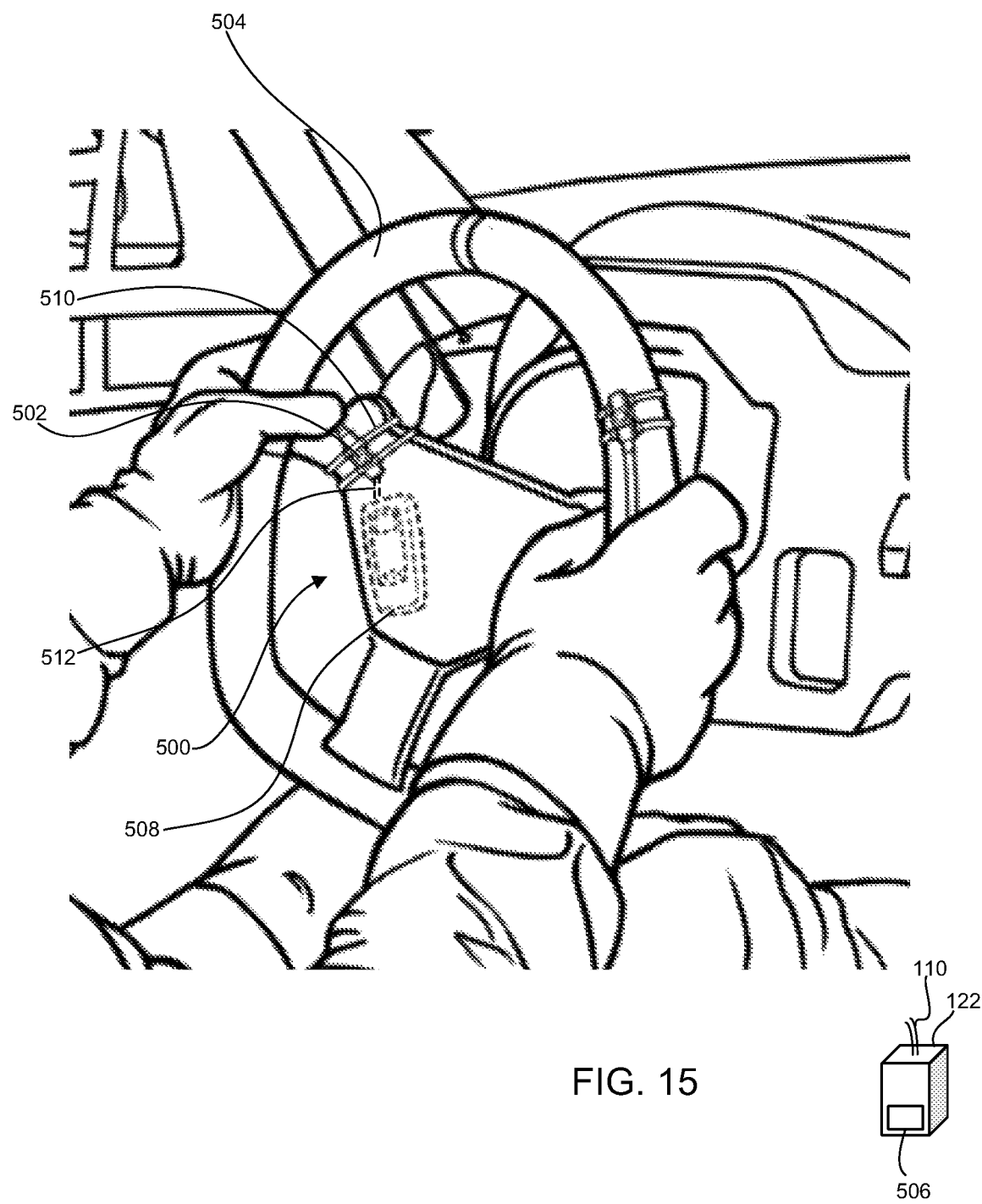
FIG. 15 illustrates an exemplary actuation system for use with a fluid delivery system.

Referring now to FIG. 15, the fluid delivery system 101 further includes a wireless actuation system 500 for remotely controlling the actuation of the second fluid source 122. A switch 502, preferably a microswitch, is operably connected to the second fluid source 122 so that operation of the microswitch 502 controls the operation of the second fluid source 122. The microswitch 502 is mounted on the steering wheel 504 in a location sufficiently proximate to where a hand of user 126 would grip the steering wheel 504 to steer the vehicle 128. In this way, the user 126 can operate the microswitch 502 without the user 126 removing his or her hand from the steering wheel 504. In the embodiment illustrated in FIG. 15, the microswitch 502 is mounted sufficiently proximate the left-hand grip. In another embodiment, the microswitch 502 may be mounted sufficiently proximate the right-hand grip. In still another embodiment, a first microswitch 502 may be mounted sufficiently proximate the left-hand grip, and a second microswitch 502 may be mounted sufficiently proximate the right-hand grip. The microswitches 502 may be mounted at a peripheral bar portion of the steering wheel 504, or may be mounted at a hub of the steering wheel 504. Furthermore, the microswitches 502 may be mounted at a front portion, at a rear portion, and/or at a side portion of the steering wheel 504.

In a preferred approach, the microswitch 502 is operably connected to the second fluid source 122 via a wireless connection between a controller 506 and a wireless transmitter 508 that is removably mounted on the steering wheel 504 proximate the microswitch 502. In other approaches, however, the microswitch 502 may be operably connected to second fluid source 122 by being hard wired to the controller 506. The controller 506 is in turn operably connected to the second fluid source 122 so as to control the operation of the second fluid source 122.

The microswitch 502 may be mounted to the steering wheel 504 using a mounting means 510 provided proximate the microswitch 502. In the approach illustrated in FIG. 15, the mounting means 510 comprises a pair of cable ties and an elongated piece of heat shrink tubing 808. In other embodiments, the mounting means may comprise other suitable structures for mounting microswitch 502 in the desired location. The wireless transmitter 508 may similarly include a mounting means attached thereto for removably attaching the wireless transmitter 508 to the steering wheel 504.

As shown in FIG. 15, a cable 512 electrically couples the microswitch 502 to the transmitter 508 to form the wireless actuation system 500. Cable 512 in the illustrated embodiment is electrically connected to the microswitch 502 at one end and includes an electrical connector, such as a conventional tip sleeve mini jack or cable jack, at a second end for selectively electrically coupling the microswitch 502 to the transmitter 508 via a mating electrical connector (such as a mating socket connector) provided in one end of the transmitter 508. The mating electrical connector provided on one end of the wireless transmitter 508 removably receives the electrical connector.

The wireless transmitter 508 is preferably in the form of a FOB and may, for example, be a Bluetooth transmitter, and more preferably a Bluetooth Low Energy ("BLE") transmitter.

The microswitch 502 is preferably a normally open switch so that it is closed when the user 126 depresses the button of the microswitch 502 and is open when the user releases the button of the microswitch 502. In some approaches, the wireless transmitter 508 is configured to transmit a first signal when the microswitch 502 is closed. The first signal may, for example, instruct controller 506 to send power to the second fluid source 122 in order to pump fluids from the second fluid source 122 through the fluid delivery system 101 to the user 126. The wireless transmitter 508 may also be configured to transmit a second signal when the microswitch is open. The second signal may, for example, instruct the controller 506 to not send power to the second fluid source 122. When the controller 506 receives the second signal, it will stop sending power to second fluid source 122 if it was previously sending power to second fluid source 122, thereby stopping the pumping of fluids from the fluid delivery system 101 to the user 126. On the other hand, if the controller 506 had previously received the second signal, such that it had already stopped sending power to the second fluid source 122, then the controller 506 will simply continue to not send power to second fluid source 122. Then when the first signal is again transmitted to the controller 506 from the wireless transmitter 508, the controller 506 will again send power to the second fluid source 122 so that it again begins to pump fluids through the fluid delivery system 101 to the user 126. In this way, the user 126 can control the delivery of fluid from the second fluid source 122 on demand by simply pressing and releasing microswitch 502. Importantly, in the illustrated embodiment, the user 126 can press and release the microswitch 502 without ever having to remove his or her hand from the steering wheel 504, so that regardless of how fast the user 126 is traveling in the vehicle 128 or the difficulty of the terrain being traversed, the user 126 is able to instruct the fluid delivery system 101 to deliver the hydration fluid contained within the second fluid source 122 as desired while maintaining both hands on the steering wheel 504 and steering the vehicle 128.

While controller 506 may be configured to provide fluids as long as the user 126 is pressing the microswitch 502 as described above, controller 506 may also be configured to provide a defined aliquot of fluids each time the controller 506 receives the first command signal (e.g., when the user 126 presses the microswitch 502, regardless of how long the user holds down the microswitch). The aliquot, for example, may be a squirt of a certain duration or volume.

In view of the fact that user 126 can safely and conveniently operate microswitch 502 while driving the vehicle 128 under various conditions, it is much more likely that the user 126 will drink fluids from the second fluid source 122 more regularly, thereby allowing the user 126 to remain hydrated during his or her ride, race, etc.

The components defining the fluid delivery path of fluid delivery system 101 shown herein are exemplary in nature, and in other embodiments of fluid delivery system 101, additional components, fewer components, or completely different components may be used to form the fluid delivery path of fluid delivery system 101. In general terms, however, the fluid delivery system 101 will typically include a fluid delivery path having a proximal end adapted to be attached to first and second fluid sources 120, 122 so that fluid communication between the fluid delivery path and the first and second fluid sources 120, 122 may be established. In addition, each fluid delivery path will include an outlet port for delivering gas and liquid fluids to a user from the first and second fluid sources 120, 122, respectively. For example, liquid may be delivered through outlet port 266 in mouthpiece assembly 112 and gas may be delivered through port 458 in helmet 103. In preferred embodiments, a magnetic quick connect, such as magnetic quick connect 106, and a secondary fluid inlet, such as splicer 108, are interposed in the fluid delivery path of the fluid delivery system 101.

Figure 16:
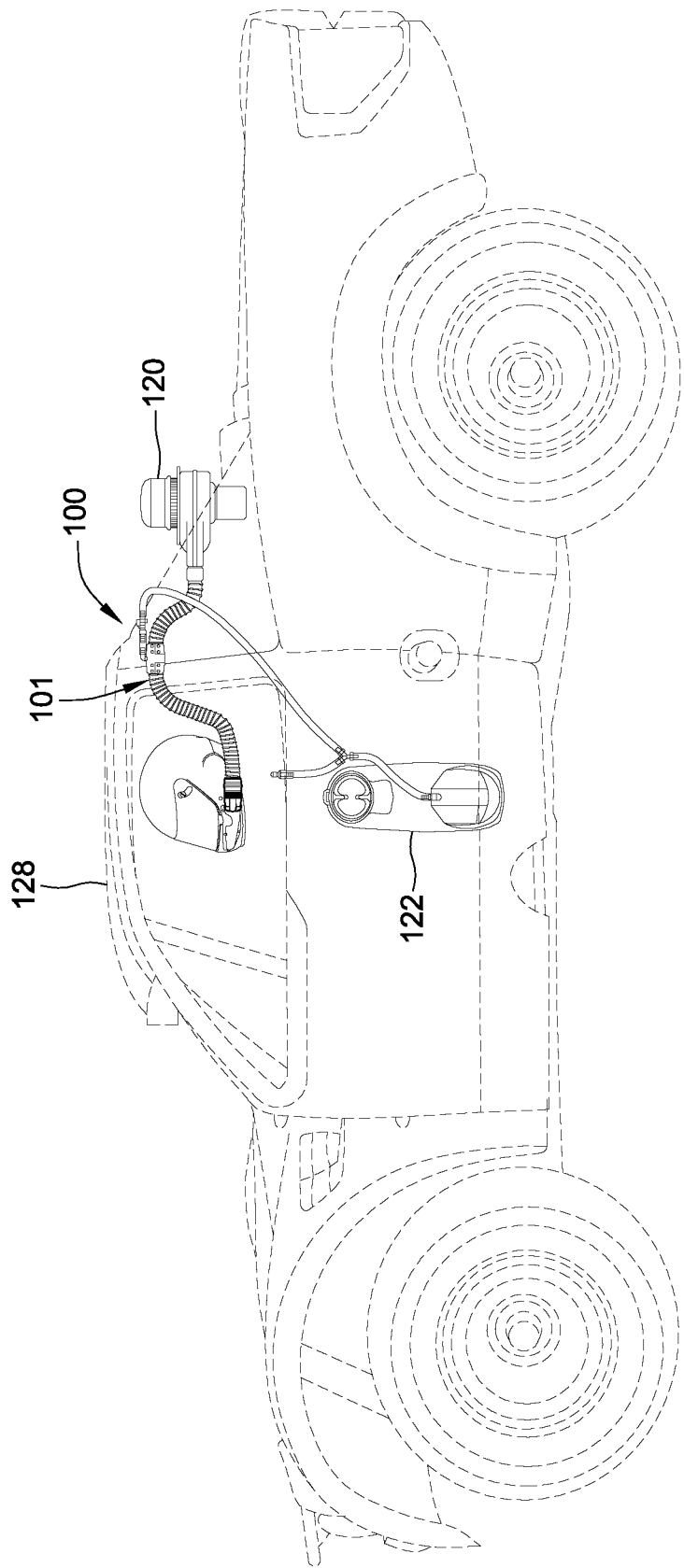
FIG. 16 illustrates an exemplary trophy truck with an alternative embodiment of a personal hydration and air cooling system that includes a two-channel fluid delivery system.
Figure 17:
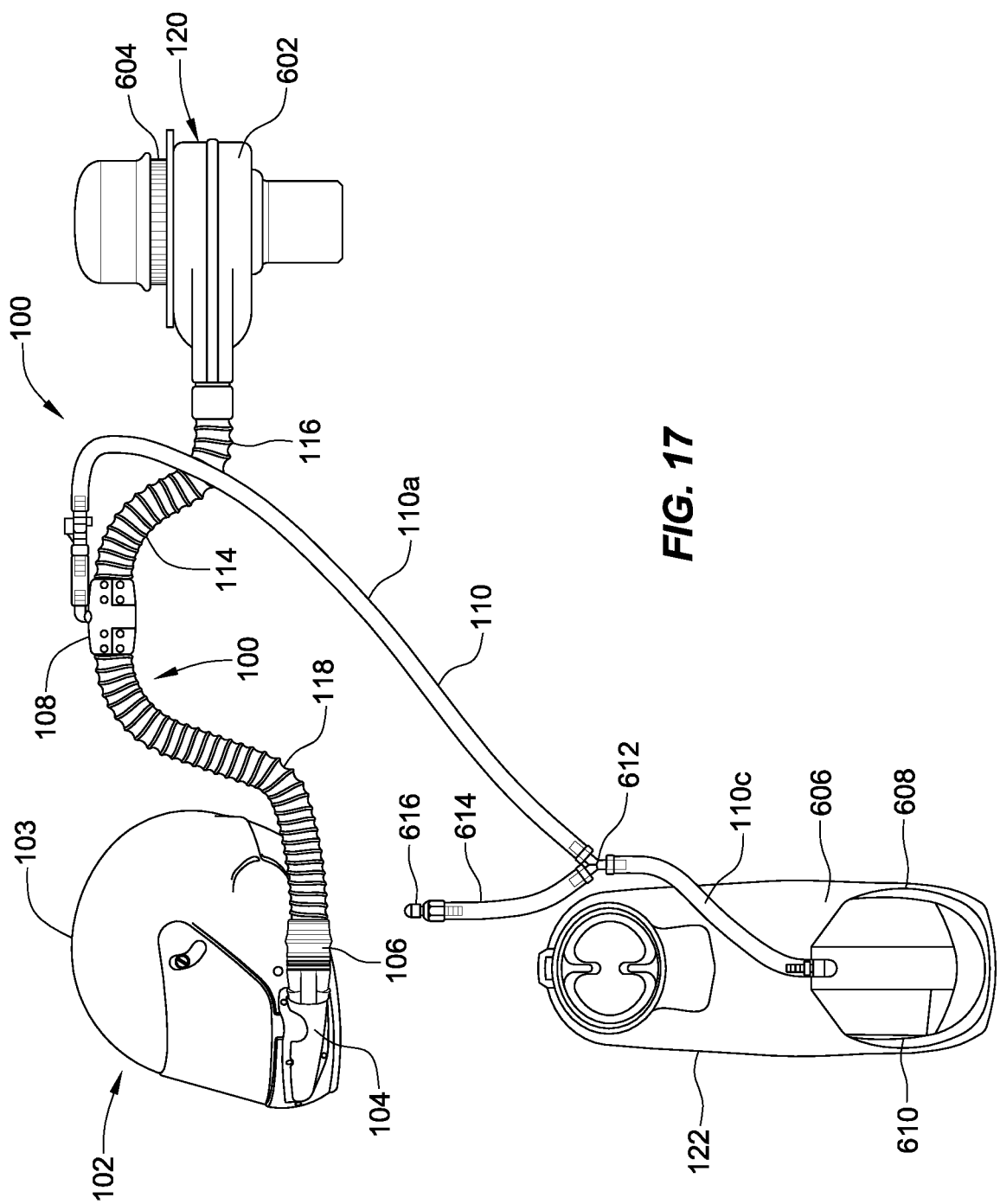
FIG. 17 is an enlarged view of the personal hydration and air cooling system of FIG. 16 with the trophy truck removed for better viewing.

Referring to FIG. 16, a vehicle 128 in the form of an exemplary trophy truck is shown. One potential layout of a personal hydration and air cooling system 100 that includes a two-channel fluid delivery system 101 for a vehicle 128 is also shown. An enlarged view of system 100 removed from the vehicle 128 is shown in FIG. 17. A similar layout may also be used for vehicles 128 other than the illustrated trophy truck. Further, the system may be replicated for a passenger.

Personal hydration and cooling system 100 of FIGS. 16 and 17 may include all of the features of the system 100 previously described above. System 100 of FIGS. 16 and 17, however, further illustrate exemplary first and second fluid sources 120, 122 that may be used in the gas and liquid subsystems, respectively, of system 100. In addition, the tubing 110 from source 122 to splicer 108 has a slightly different arrangement, because second fluid source 122 of system 100 may be refilled without having to remove source 122 from the vehicle 128.

First fluid source 120 in the present embodiment takes the form of an enclosed fan or blower 602 having a filter element 604 interposed between ambient air and the intake of the blower 602. The filter 604 removes dust and other debris delivered to user 126, thereby ensuring user 126 has a source of clean air to breathe. Fan 602 may, for example, me a Parker Pumper Fresh Air Blower, which can be obtained from RaceReady Products. Many other suitable fresh air blowers are also readily available on the market.

Second fluid source 122 may comprise a fluid reservoir 606 containing a potable liquid, such as water or a sports drink with electrolytes. Flexible reservoirs such as those provided by CAMELBAK™ are particularly well suited for use as fluid reservoir 606 of the hydration and cooling system 100 of the present patent document. As seen in FIG. 16, such reservoirs will fit well in many locations within the cabin of a vehicle 128, such as the illustrated trophy truck.

Although flexible hydration reservoirs, such as those provided by CAMELBAK™, are particularly well suited for use as fluid reservoir 606 in the system 100 of the present patent document, any suitable sealable container can be used for fluid reservoir 606. For example, depending on the application reservoir 606 may be made from rigid, semi-rigid, or flexible material. Furthermore, in some applications, it may be desirable to use a reservoir that is insulated, such as an insulated bottle or jug, for the reservoir 606. Alternatively, the reservoir 606 may be included within an insulated sleeve in some embodiments.

Regardless of the particular form of reservoir 606, the material or materials used in its construction (particularly any that will come in contact with the fluids contained within reservoir 606) should be suitable for contact with liquids that are intended for human consumption. This is also true with the other portions of liquid subsystem of hydration and cooling system 100 that may come in contact with fluid that is transported from the reservoir 606 through the liquid channel of fluid delivery system 101 to the user 126.

In the present embodiment, second fluid source 122 also includes a fluid control unit 608. Fluid control unit 608 includes a pump (not shown) contained within housing 610. The pump is in fluid communication with reservoir 606 through an output port of the reservoir. The pump is also in fluid communication with a proximal end of hydration input tube 110 of fluid delivery system 101. Fluid control unit 608 also includes a controller 506 that is in wireless communication with wireless actuation system 500. Controller 506 is in turn electrically and operably connected to the pump and power source in fluid control unit 608 so as to provide the necessary power to drive the motor of the pump when instructed by the wireless actuation system 500. As a result, wireless actuation system 500 may be used to wirelessly control the operation of the pump in fluid control unit 608 via controller 506 in the manner previously described.

Fluid control unit 608 and wireless actuation system 5000 collectively form a wireless pump system. And, while a wireless actuation system 500 is preferably employed to control the operation of the pump in fluid control unit, in other embodiments a microswitch 502 that is electrically connected to the pump or controller 506 may be used. However, in addition to eliminating the need for at least two conductors to electrically connect the switch 502 to the pump or controller 506, the wireless actuation system 500 may provide a number of advantages over a switch 502 that is electrically connected to the pump or controller 506 in controller 608.

The fluid control 106 unit and wireless actuation systems 140 described in co-pending U.S. application Ser. No. 15/652,847, the description of which is hereby incorporated by reference as if fully set forth herein, may be used for control unit 608 and wireless actuation system 500 of the present patent document.

Fluid source 122 may be suspended directly from a frame or roll cage member within the cabin of vehicle 128, or, alternatively, it may be placed in a bag, which is then suspended from the frame or roll cage member.

The hydration input tube 110 of the present embodiment includes a tube section 110c which is connected at a proximal end to the output of the pump in fluid control unit 106 and at a distal end to one branch of a Y-connector 612. A second branch of Y-connector 612 is connected to the proximal end of tube section 110a. The third branch of the Y-connector 612 is connected to the proximal end of a refill tube 614. The distal end of tube 614 is connected to a hose connector 616 that one-way valve. The hose connector 616 may connect to the distal end of tube 616 using a hose connector, such as a barbed hose connector. The distal end of hose connector 616 preferably includes a male or female mechanical quick connect or a magnetic quick connect, such as those previously described herein.

With the above configuration, when a driver 126 comes in for a pit stop or driver change, the fluids in reservoir 606 may be replenished by connecting a hose of a refill reservoir having a complementary connector to the distal end of connector 616. Liquid from the refill reservoir may then be transferred to reservoir 606 by driving the pump in control unit 608 in reverse, or using a pump on the refill system, to pump liquid from the refill reservoir to reservoir 606 via connector 614, connector 612, tube section 110c, and control unit 608.

The pump in control unit 608 may be driven in reverse, for example, when a button on transmitter 508, or another transmitter that is connected to controller 506, is depressed. In one approach, the wireless transmitter 508 is configured to transmit a third signal when a button on the transmitter 508 is pushed. The third signal may instruct controller 506 to send power with reverse polarity to the pump in fluid control unit 608 in order to drive it in the reverse direction.

Figure 18:
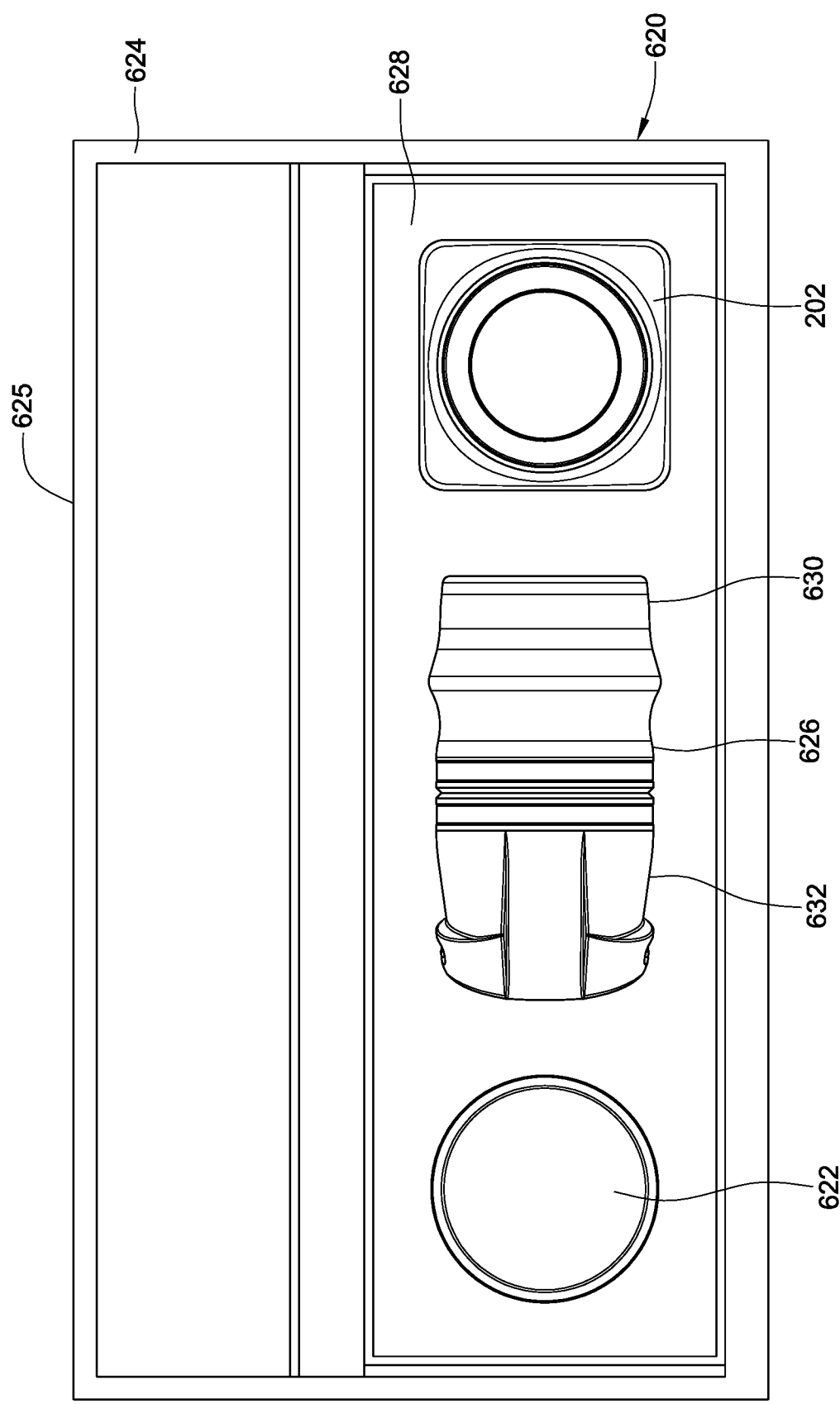
FIG. 18 illustrates a kit, including a magnetic quick connect for use with forced air headgear, such as a forced air helmet, a quick connect holder, and a dust cap.

Referring to FIG. 18, another aspect of the present patent document is now discussed. FIG. illustrates a kit 620 including a magnetic quick connect 626 for use with forced air headgear, such as a forced air helmet 103, a quick connect holder 202, and a dust cap 622. In the present embodiment, the kit elements 626, 202, and 622 are all packaged together in a package 624, such as a box 624, with a lid 625 connected to the body of the box with a living hinge. The base of box 624 may include a foam packing material 628 with cutouts for receiving the quick connect 626, quick connect holder 202, and dust cap 622.

Magnetic quick connect 626, includes an upstream coupling member 630 and a downstream coupling member 632. The upstream end 630 and downstream coupling member are also referred to herein as a hose side connector and a helmet or headgear side connector 632, respectively.

Magnetic quick connect 626 may be a two-channel quick connect for transporting a first fluid and a second fluid, such as a gas and a liquid, from a downstream end to an upstream end, it may be a single channel quick connect for transporting a single fluid, such as a gas from an upstream end to a downstream end, or it may selectively be a single channel or two-channel quick connect.

While the illustrated kit 620 includes a quick connect 626, dust cap 622, and quick connect holder 202, in other embodiments, the kit 620 may include fewer or more items. For example, the kit may only include quick connect 626, quick connect 626 and dust cap 622, or quick connect 626 and quick connect holder 202. Further, in some approaches, coupling member 63 may be integrated with a helmet 103 or other headgear, and thus the kit may only include the hose side connector 630.

Figure 19:
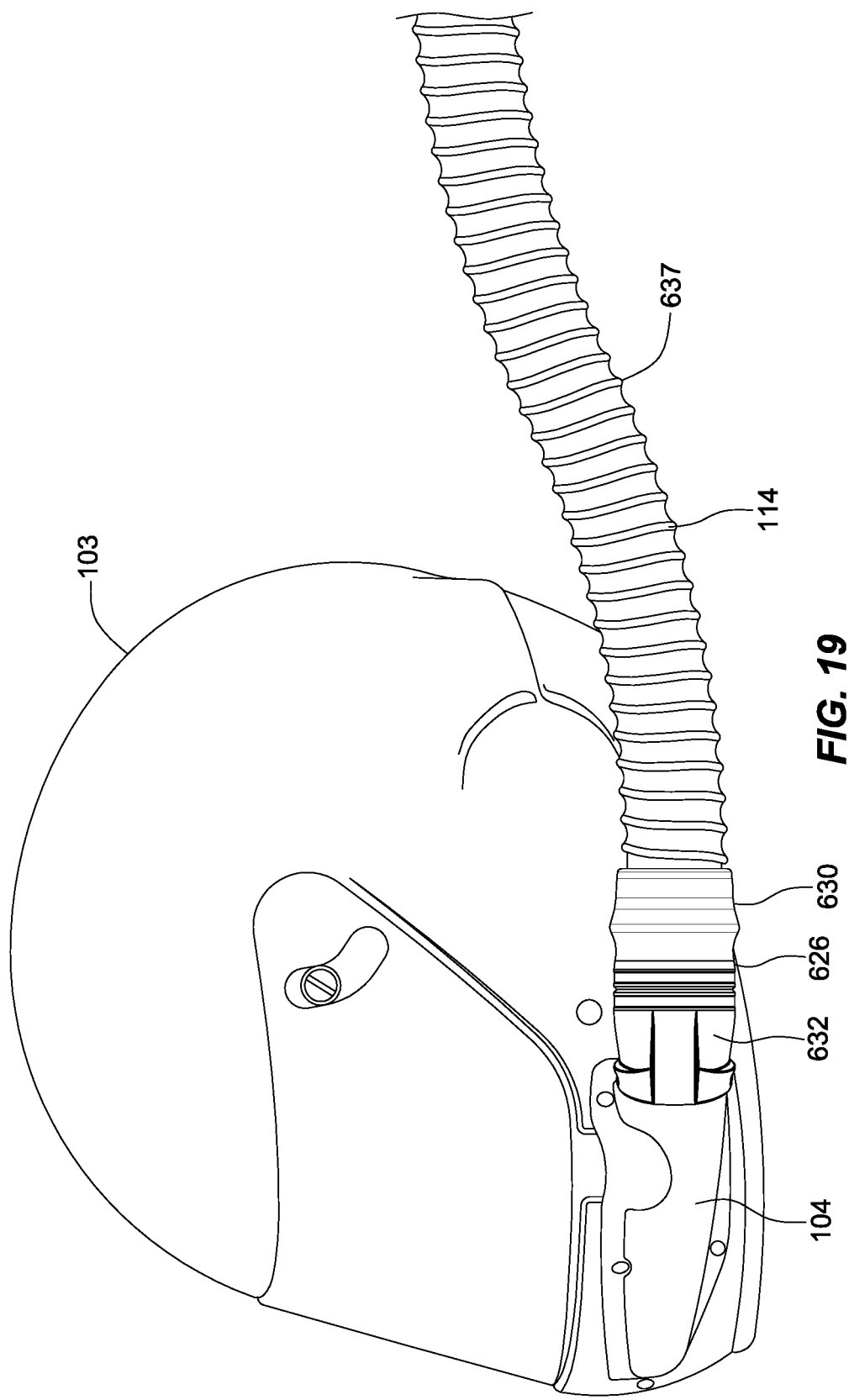
FIG. 19 illustrate the magnetic quick connect of FIG. 18 in use with one type of forced air helmet.

FIG. 19 illustrates a single-channel magnetic quick connect 626 connected to the input tube of the helmet interface 104 of a forced air helmet 103. More particularly, the helmet side connector 632 is connected to the input tube of the helmet interface 104 and the hose side connector is connected to the distal end of tube 114. The proximal end of tube 114 may be connected to a first fluid source 120, such as clean air blower 602.

With this configuration, a user 126 may be provided clean air to breath, yet the upstream and downstream connectors 630, 632 may be readily, and safely disconnected as discussed above with respect to male coupling member 130 and female coupling member 158 of magnetic quick connect 106.

While FIG. 19 illustrates magnetic quick connect 626 in use with a forced air helmet 103 with a helmet interface 104 located on its side, quick connect 626 may also be used with forced air helmets with a helmet interface 104 located in other positions as well. For example, magnetic quick connect 626 may also be used with helmet 103 shown in FIG. 3B. Further, magnetic quick connect 626 may also be used with other forced air headgear. Two non-limiting examples of other types of forced air headgear with which magnetic quick connect 626 may be used are shown in FIGS. 50 and 51.

Figure 50:
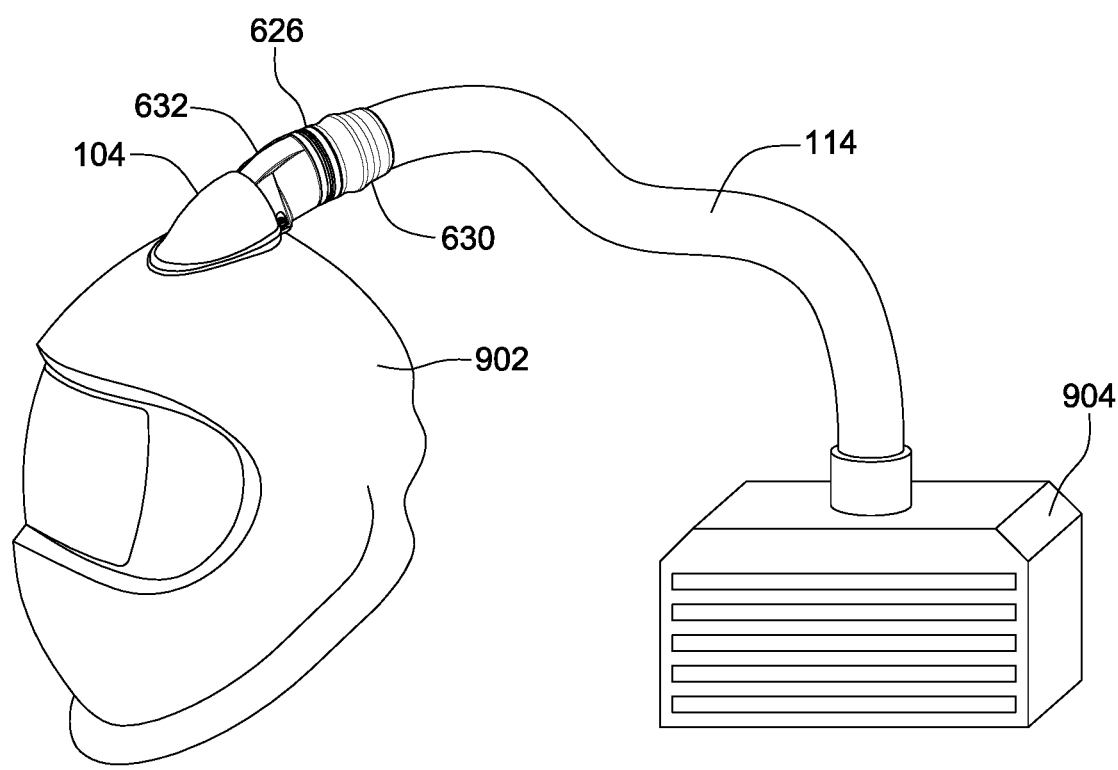
FIG. 50 illustrates the magnetic quick connect of FIG. 18 in use with another type of forced air headgear, namely a forced air welding helmet with a portable respirator fan.

FIG. 50 illustrates the magnetic quick 626 in use with another type of forced air headgear, namely a forced air welding helmet 902. In FIG. 50, the headgear side connector 632 is connected to the input tube of a visor helmet interface 906, and the hose side connector is connected to a distal end of a tube 114. The proximal end of tube 114 is connected to and in fluid communication with a portable respirator fan, such as respirator fan 904. Respirator fan 904 provides filtered air to the interior space of visor 906 around a user's face via hose 114, quick connect 626, and visor interface 908. Respirator fan 904 is preferably sized to be worn around the waist of a user 126. Further fan 904 may include a belt or means for attaching to a belt of user 126.

Figure 51:
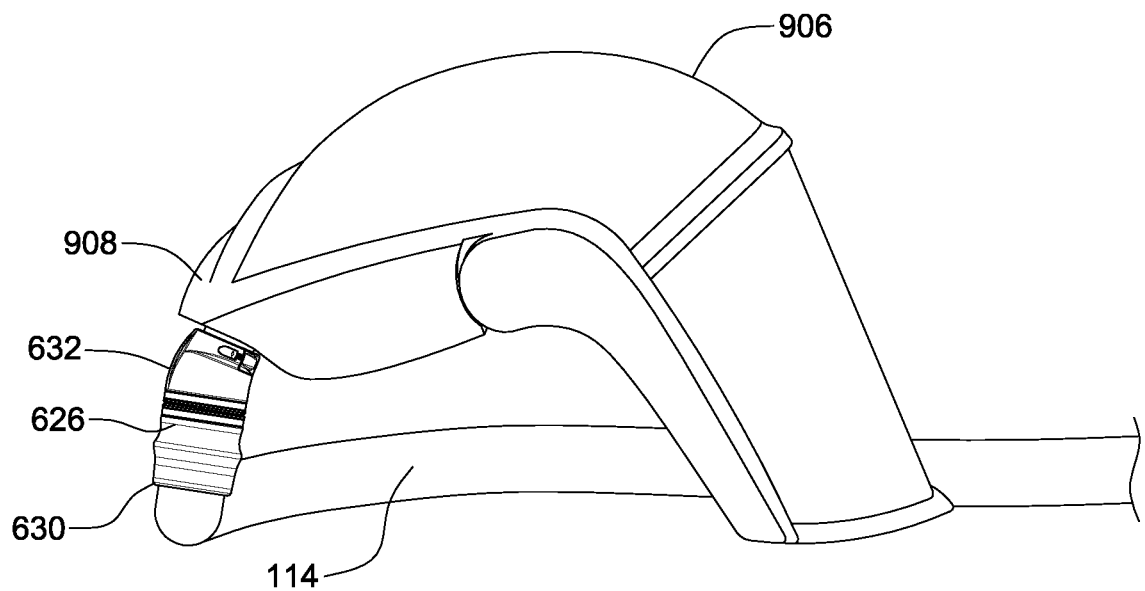
FIG. 51 illustrates the magnetic quick connect of FIG. 18 in use with another type of forced air headgear, namely a forced air respirator faceshield.

FIG. 51 illustrates the magnetic quick connect 626 in use with another type of forced air headgear, namely a forced air respirator faceshield 906. In FIG. 51, the headgear side connector 632 is connected to the input tube of interface 104, and the hose side connector is connected to a distal end of a tube 114. The proximal end of tube 114 is connected to and in fluid communication with a portable respirator fan 904, which provides filtered air to the interior of helmet 902 via hose 114, quick connect 626, and helmet interface 104.

Magnetic quick connect 626 and its respective connectors 630, and 632 are now described in connection with FIGS. 23-37. Magnetic quick connect 626 and its respective connectors 630, 632, share many of the same features as magnetic quick connect 106 and its respective connectors 130, 158. Accordingly, similar features have been labeled with common reference numbers so that the features do not need to be described again.

Unlike magnetic quick connect 106, quick connect 626 is a single channel, gas only quick connect. Inner member 148 is, therefore, not included in helmet side connector 632, and inner member 180 is not included in hose side connector 630. As a result, there is no "male" connector or "female" connector. Notwithstanding, as previously described with connectors 130, 152 of quick connect 106, the magnetic force of attraction between connectors 630, 632 will automatically align the connectors when the mating ends 134, 162 are brought into proximity with one another, thereby allowing one handed, non-visual operation of quick connect 626, just as with quick connect 106.

Further, because inner members 148, and 180 have been omitted, the magnetic quick connect 630 only has a first fluid communication channel 167 extending therethrough. The first communication channel 167 comprises communication path 136 in the helmet side connector and fluid communication path 166 in the hose side connector.

Although the illustrated coupling members 632, 630 do not include respective inner members 148, 180, the coupling members include slots 152, 184, respectively, so that if a two-channel magnetic quick connect 626 is desired, the inner members, 148, 180 may be added to the connectors 632, 630, by seating the fins 150, 182 of inner members 148, 180 in their respective slots. In this manner, quick connect 626 may be constructed as a single channel or two-channel quick connect simply by whether the inner members 150, 182 are included or omitted during the manufacturing process.

Figure 28:
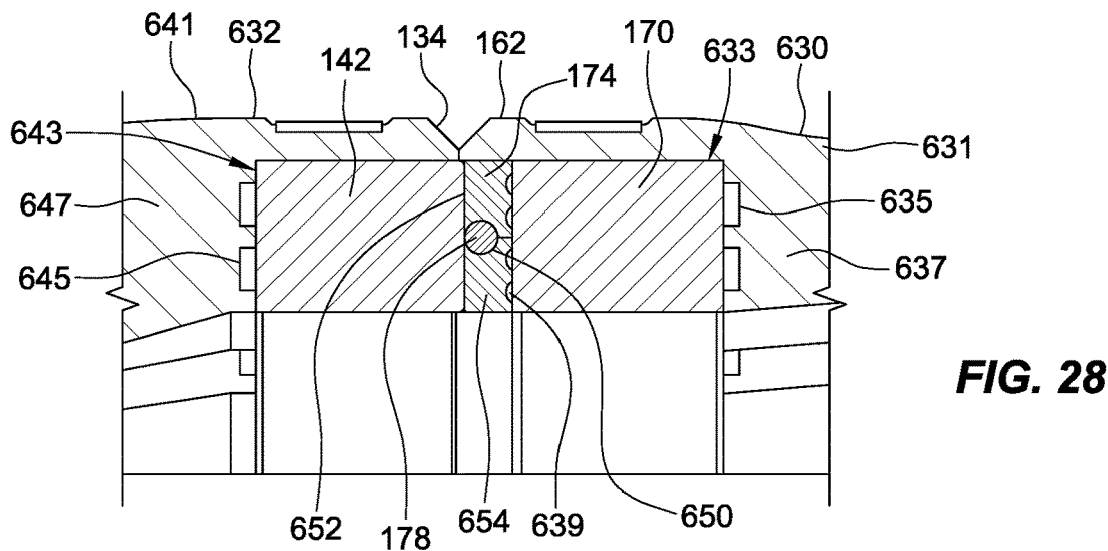
FIG. 28 is a blow up of the area circled in FIG. 27.
Figure 29:
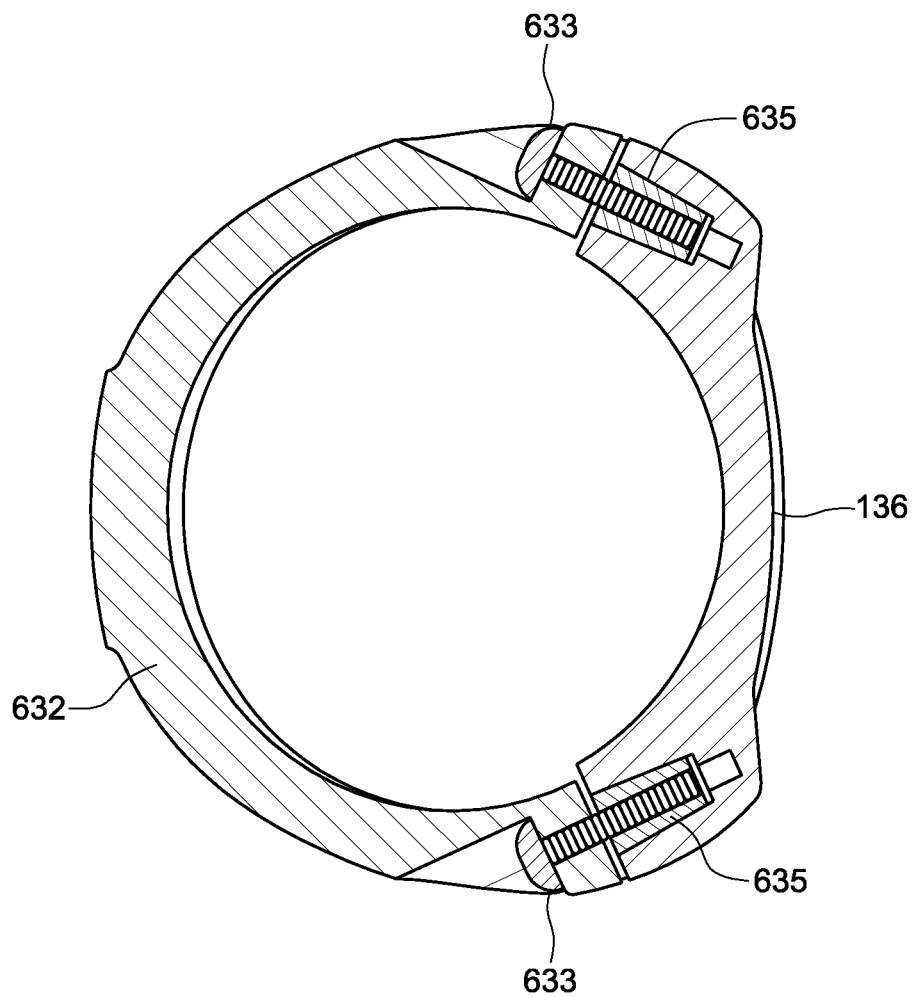
FIG. 29 is a cross-sectional view of the magnetic quick connect of FIG. 26 taken along cutline 29-29.

As with coupling member 158, coupling member 630 includes a cap 174 provided at the mating end 162 of the coupling member 630. O-ring 178 is preferably disposed in an annular groove 650 provided in cap 174. As best seen in FIGS. 28 and 49, the annular groove is preferably C-shaped so that the opening at the mating face of cap 174 is narrower than the diameter of O-ring 178. If annular ring 650 is rectangular in shape, O-ring 178 may fall out over time, even if initially secured in channel 650 with an adhesive. On the other hand, if annular channel 650 is C-shaped as described, then O-ring 178 may be safely secured within the channel, even after repeated attachments and detachments to coupling member 632 and/or quick connect holder 202.

A C-shaped annular groove cannot be machined, cast, or injection molded into a annular cap 174 made from a unitary piece. If, however, annular cap 174 is 3D printed, then a C-shaped groove 650 may be formed directly in cap 174, even if cap 174 is made from a unitary piece. On the other hand, as best seen in FIGS. 28 and 47-49, a C-shaped groove 640 may be readily formed through injection molding, casting, or machining, if cap 174 is made from two concentric rings 652, 654 as illustrated.

The downstream coupling member 632 includes an adjustable clamp portion 136 like male coupling member 130. The adjustable clamp portion 136 may take the form of a "C-clamp", and may be removably connectable to the coupling member 632, for example, through the use of screws or other fastening devices. In this way, the adjustable clamp portion 136 allows the male coupling member 632 to be secured to the input of a helmet interface 104 of helmet 103 or other headgear such as welding helmet 902. Similarly, it allows coupling member 632 to be secured to the input of visor interface 908. For example, a user may remove the adjustable clamp portion 136 and position a tubing, such as an input tube, of the helmet interface 104 within the body of the coupling member 632. The user then reconnects the adjustable clamp portion 136 to the coupling member 632, thereby securing the coupling member 632 to the helmet interface 104 of helmet 103 or other headgear. Other suitable mechanisms and fastening devices for securing the coupling member 632 to a helmet 103 are expressly contemplated herein.

In the present embodiment, adjustable clamp member is attached to coupling member 632 with screws 633, which thread into threaded inserts 635 that are co-molded into the adjustable clamp portion 136.

Adjustable clamp member 136 may include a friction pad 640 positioned on an interior surface of the clamp member 136. The friction pad 640 is sized so that when the clamp member 136 is attached to the coupling member 630, it engages with, and is compressed by, the surface of the input tube to which the coupling member 630 is being attached, thereby increasing the frictional forces securing the coupling member 630 to the input tube of the forced air headgear, such as helmet interface 104.

The first end 160 of the upstream coupling member 630 may be secured to hose 114 by screwing it onto threads 637 formed by the spiral in tube 114. This may be accomplished by providing matching threads 638 inside the body of the first end 160 of the upstream coupling member 630 to engage with the threads 637 on hose 114. Other suitable mechanisms and fastening devices for securing the coupling member 630 to hose 114 are expressly contemplated herein, including the use of an adjustable clamp portion 164 as described with coupling member 158.

As best seen in FIGS. 28 and 30-31, the tubular body 631 of coupling member 630 defines a recess 633 that is sized to receive the annular second magnetic material 170 and annular cap 174 therein. The second magnetic material 170 and annular cap 174 may be secured to the tubular body 631 with any suitable means, including, for example adhesive. Annular grooves 635 may be provided in abutting shelf 637 to facilitate the bonding of the annular second magnetic material 170 to tubular body 631. Similarly, annular grooves 639 may be provided in the back side of annular cap 174 to facilitate the adhesive bonding of annular cap 174 to the annular second magnetic material 170 and tubular body 631.

Figure 34:
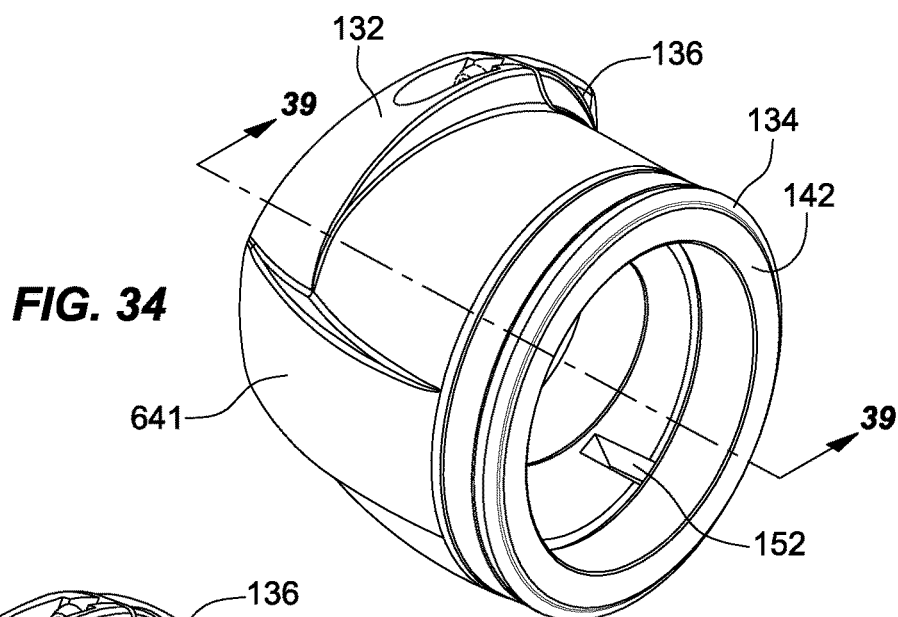
FIG. 34 illustrates a perspective view of the helmet side connector of the magnetic quick connect of FIG. 23 from its upstream end.
Figure 35:
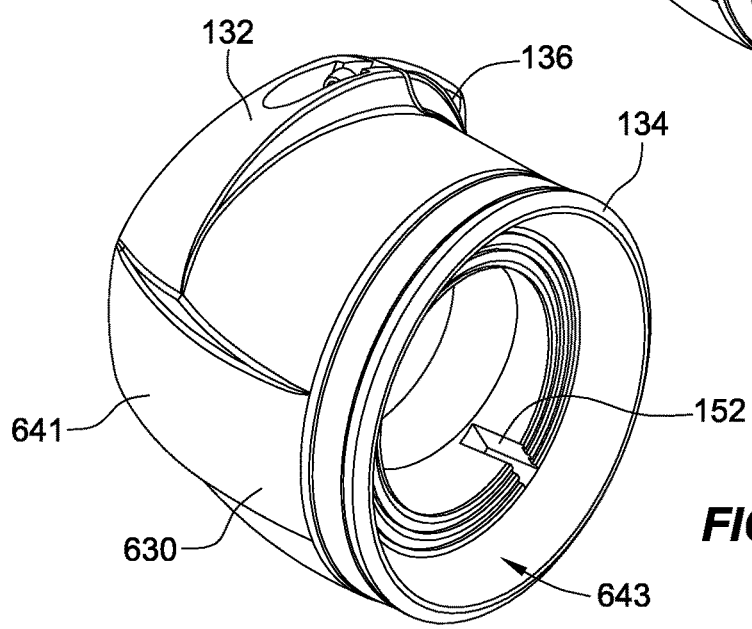
FIG. 35 illustrates a perspective view of the helmet side connector of the magnetic quick connect of FIG. 23 from its upstream end with a magnetic material removed.
Figure 36:
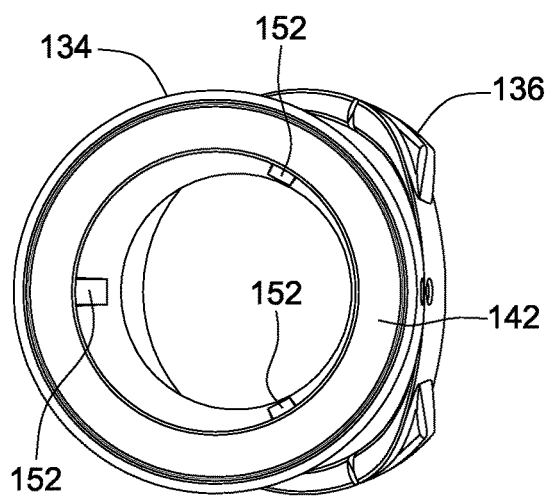
FIG. 36 illustrates an upstream end view of the helmet side connector of FIG. 34.
Figure 37:
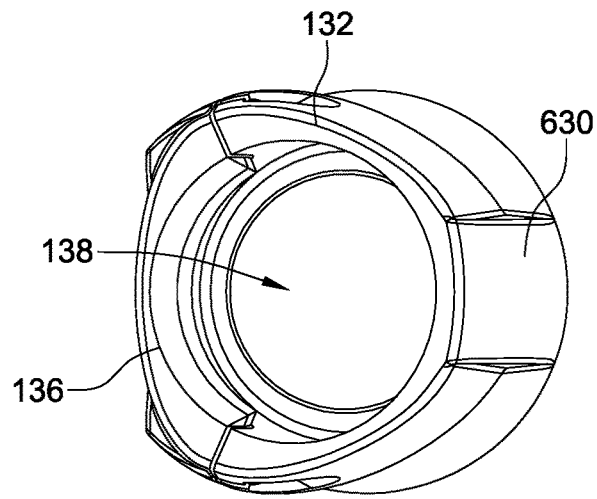
FIG. 37 illustrates a downstream end view of the helmet side connector of FIG. 34.

As best seen in FIGS. 28 and 34-35, the tubular body 641 of coupling member 632 defines a recess 643 that is sized to receive the annular first magnetic material 142 therein. The first magnetic material 142 may be secured to the tubular body 641 with any suitable means, including, for example adhesive. Annular grooves 645 may be provided in abutting shelf 647 to facilitate the bonding of the annular first magnetic material 142 to the mating end of tubular body 641.

Figure 20:
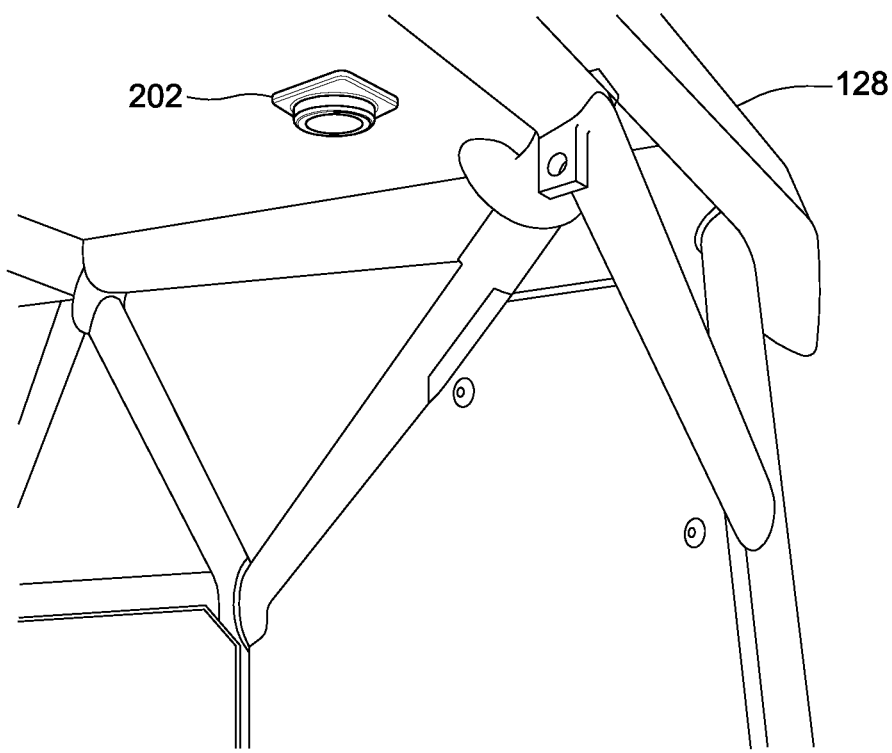
FIG. 20 illustrates the quick connect holder of FIG. 18 attached to the roof of a race car.
Figure 21:
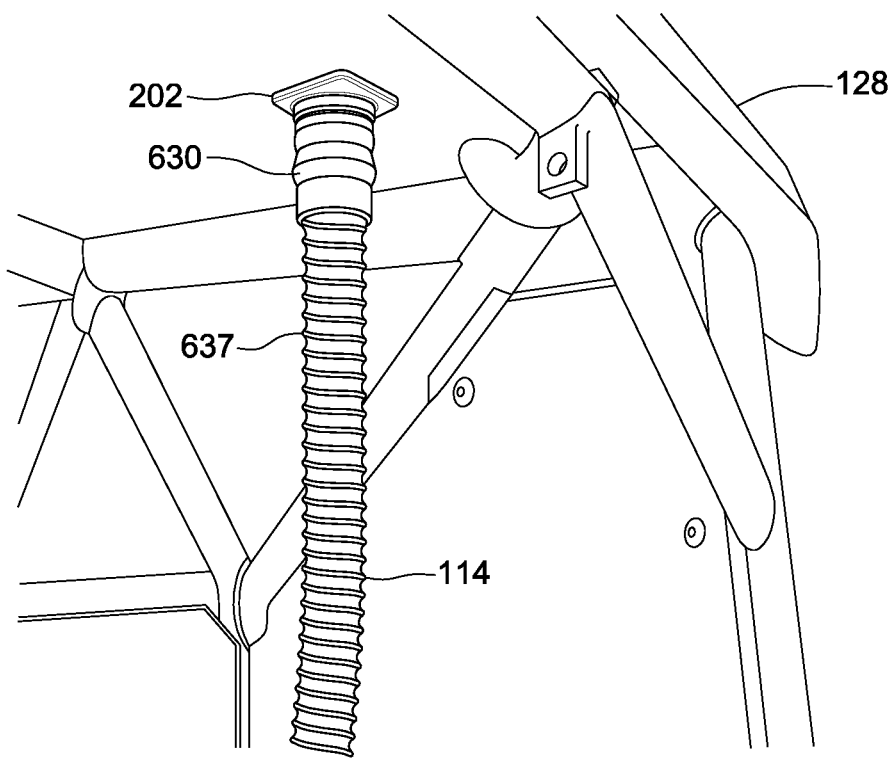
FIG. 21 illustrates the quick connect holder of FIG. 18 attached to the roof of a race car with a hose side connector of the magnetic quick connect of FIG. 18 removably attached thereto.

The operation of quick connect holder 202 is now described in connection with FIGS. 20, 21, 38 43-46. FIG. 20 illustrates the quick connect holder 202 of kit 620 attached to the roof of vehicle 128, such as a race car or trophy truck. FIG. 21 illustrates the quick connect holder 202 attached to the roof of vehicle 128 with the down steam end of hose side connector 630 of quick connect 626 removably attached to the face of quick connect holder 202. As previously described, the upstream end of the connector 630 is connected to the distal end of tube 114, and the proximal end of tube 114 is in fluid communication with a first fluid source 120, such as clean air blower 602.

With the foregoing arrangement, user 126 may detach the hose side connector 630 from the helmet side connector 632 when exiting the vehicle and place it on quick connect holder 202 for convenient storage for future use. This can minimize the damage to equipment, as well as speed potential driver changes by ensuring that the tube 114 and connector 630 remain out of the way during the driver change and that it is readily available for the new driver/user 126. Further, the driver or user 126 can easily locate tube 114 and connector 630 once seated within the cabin of vehicle 128, remove the connector from quick connect holder 202, and attach connector 630 to the helmet side connector 632 with a single hand.

As shown in FIGS. 38 and 43-46, quick connect holder 202 includes a base end 660 with a pedestal portion 662 extending therefrom. The pedestal portion 662 includes an annular channel in which an annular first magnetic material 142 is secured, such as by adhesive. Preferably the pedestal portion 662 is dimensioned to match that of the outer diameter of the mating end of coupling member 662. Further, the annular first magnetic material 142 has the same dimensions and magnetic properties as the first magnetic material 142 used in coupling member 630. In this way, coupling member 630 will automatically align with and couple with the mating end 664 of quick connect holder 202 when brought into its vicinity.

Figure 38:
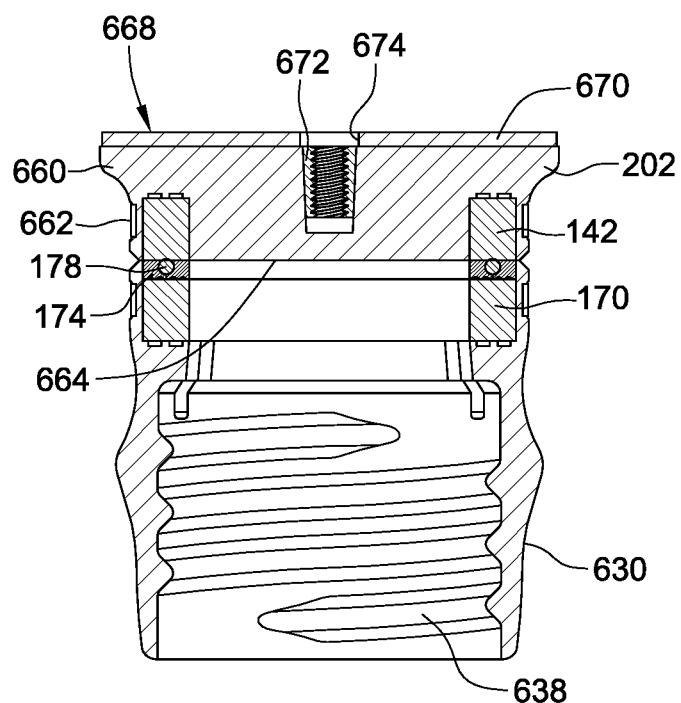
FIG. 38 is a cross-sectional side view through the hose side connector of the magnetic quick connect of FIG. 18 when removably connected to the quick connect holder of FIG. 18 as illustrated in FIG. 21.
Figure 40:
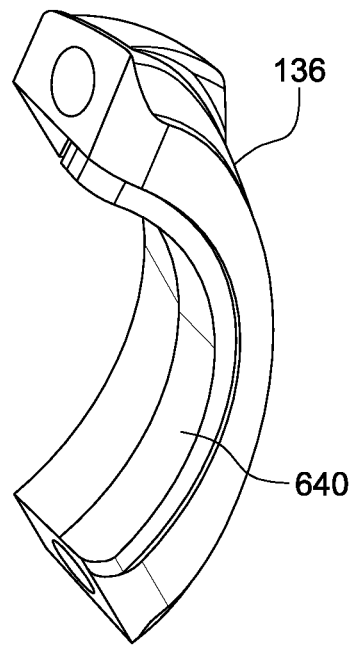
FIG. 40 illustrates a perspective view of a clamp portion of the helmet side connector.

The back side 668 of quick connect holder 202 preferably includes an adhesive pad 670. Adhesive pad 670 is preferably a double sided adhesive pad. When shipped in kit 620 the outer facing side of adhesive pad 670 may include a protective coating on it. User 126 may remove the protective coating and then secure quick connect holder 202 to the roof of a vehicle 128. Alternatively, or in addition, a threaded insert 672 may be co-molded into the base 660 so that the mouth of the insert is exposed on the backside 668 of base 660 as best seen in FIGS. 38 and 46. A hole 674 may be provided in the adhesive pad 670 so that a bolt may extend through the adhesive pad 670 into the threaded insert 672. Threaded insert 672 provides an additional or alternative means of connecting quick connect holder 202 to the roof of vehicle 128.

Figure 22:
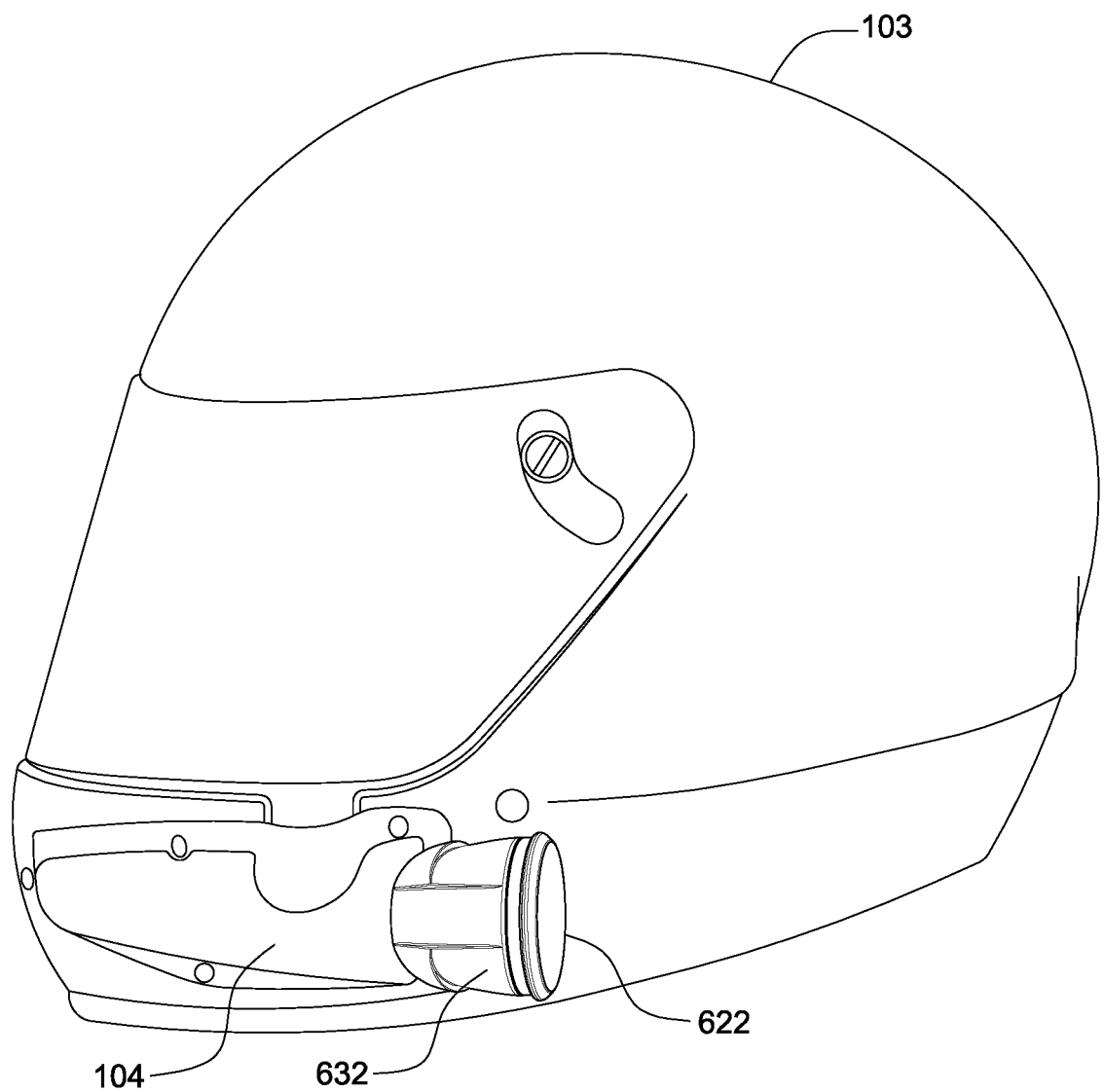
FIG. 22 illustrates the dust cap of FIG. 18 in use with the headgear side connector of the magnetic quick connect of FIG. 18 that is attached to a forced air helmet.
Figure 23:
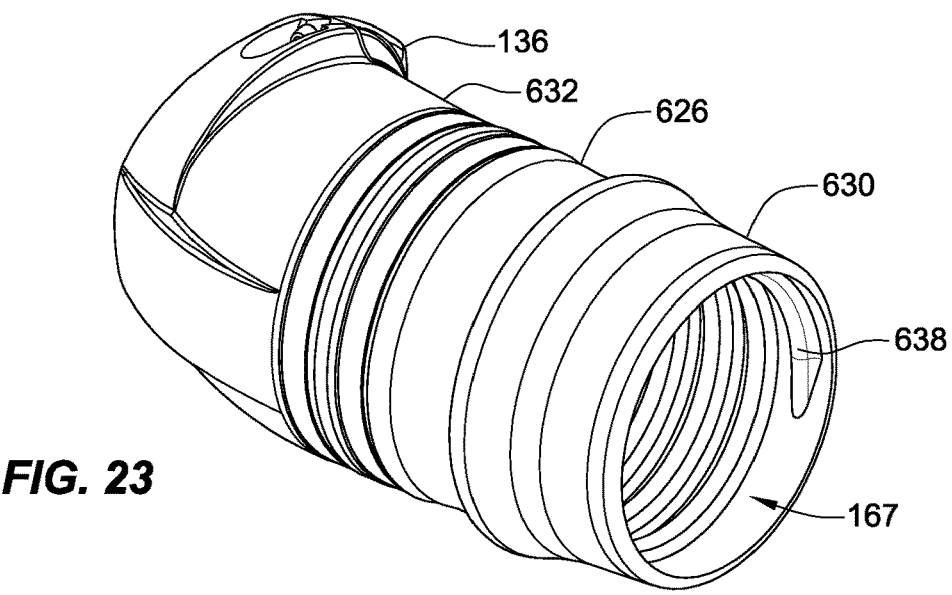
FIG. 23 illustrates a perspective view of a magnetic quick connect of FIG. 18.
Figure 24:
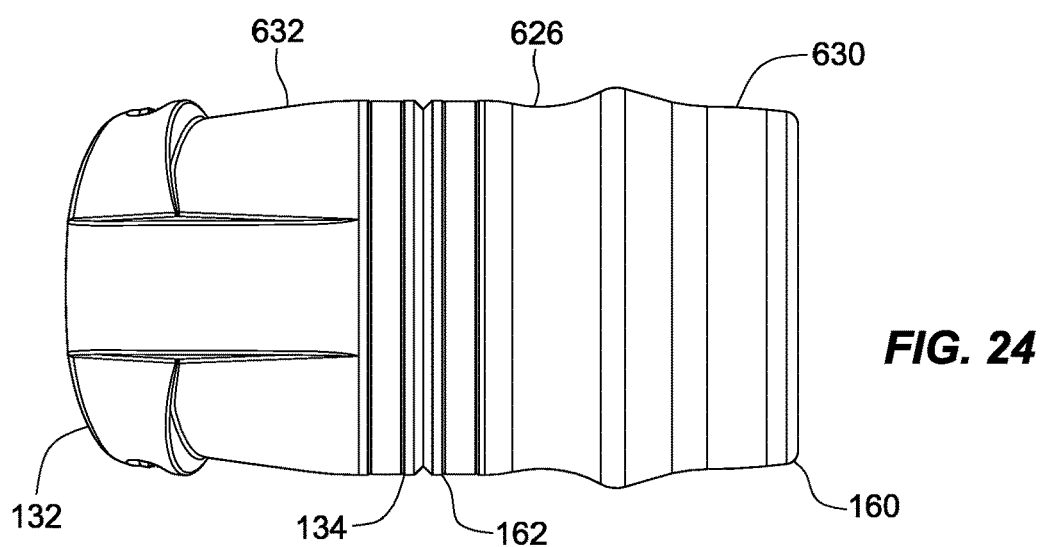
FIG. 24 is a side elevation view of the magnetic quick connect of FIG. 23.
Figure 25:
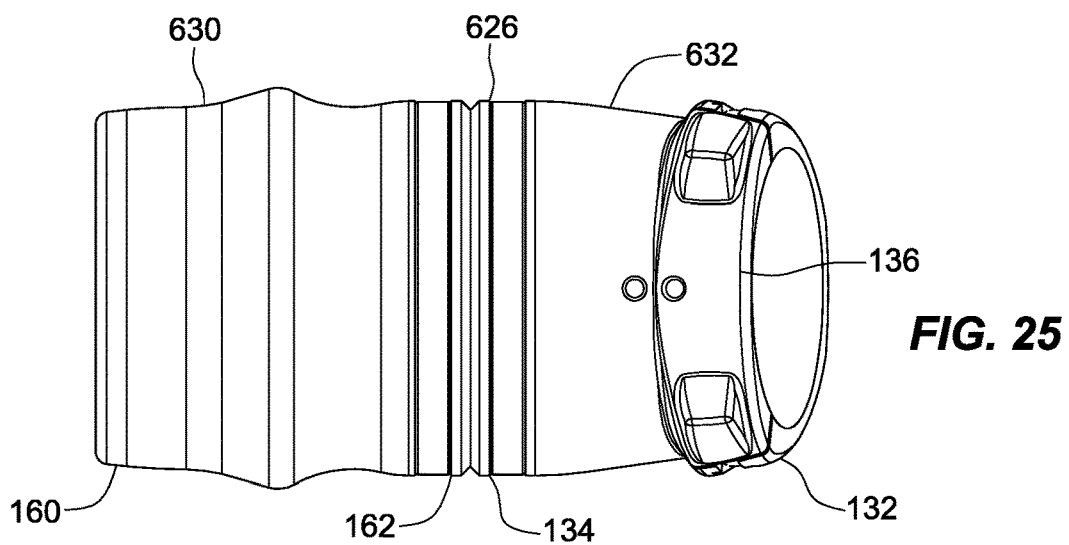
FIG. 25 is a side elevation view of the magnetic quick connect of FIG. 23 showing the opposite side shown in FIG. 24.
Figure 26:
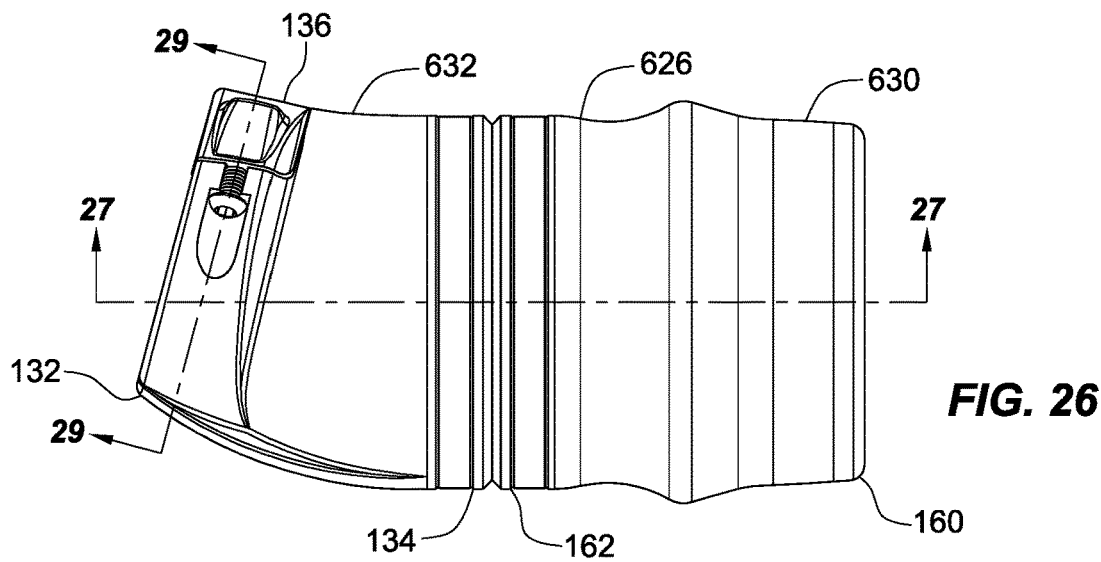
FIG. 26 is a top plane view of the magnetic quick connect of FIG. 23.
Figure 27:
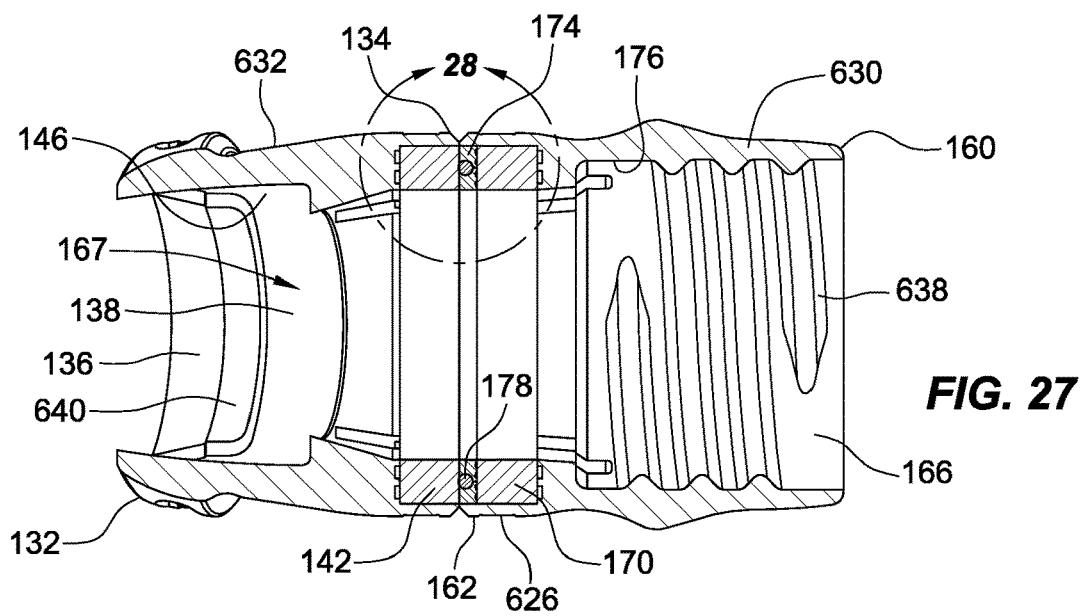
FIG. 27 is a cross-sectional side view of the magnetic quick connect of FIG. 26 taken along cutline 27-27.

FIG. 22 illustrates the dust cap 622 of kit 620 in use with the headgear side connector 632 of the magnetic quick connect 626, which in turn is attached to an input tube of a forced air helmet.

Figure 39:
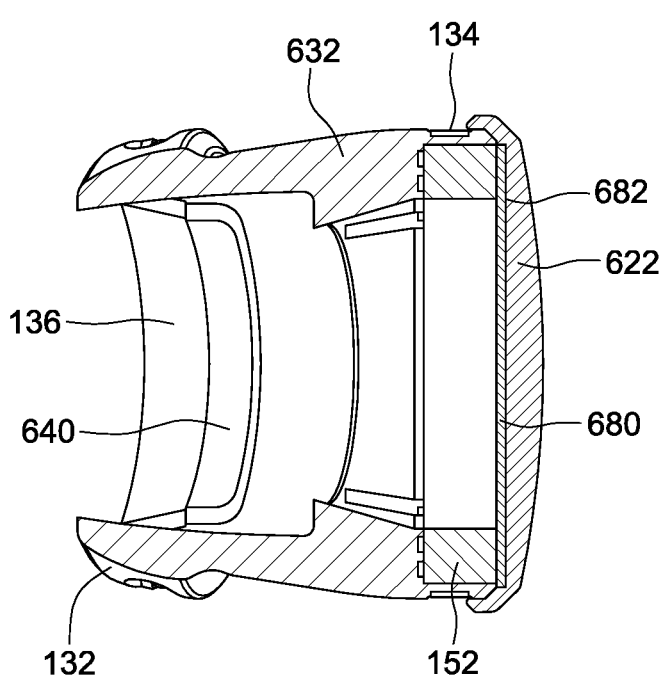
FIG. 39 is a cross-sectional view through the helmet side connector of the magnetic quick connect of FIG. 18 with the dust cap of FIG. 18 removably attached thereto. The cross-sectional view through the helmet side connector is taken along cutline 39-39 of FIG. 34.
Figure 41:
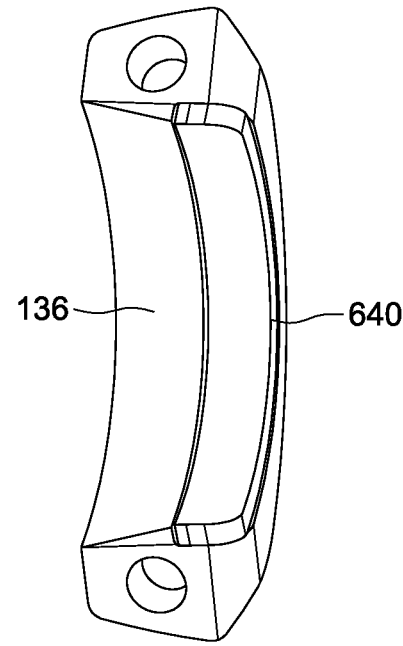
FIG. 41 illustrates a side elevation view of the clamp portion of the helmet side connector.
Figure 42:
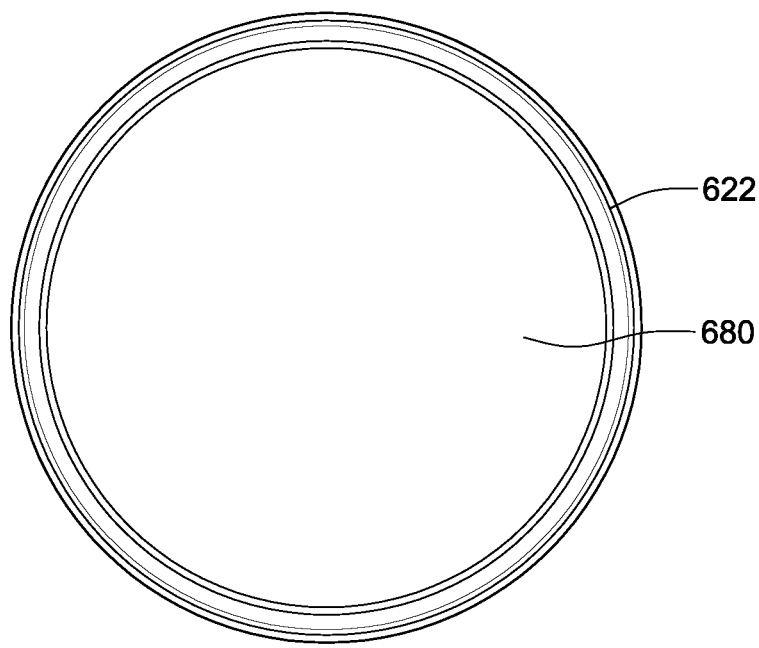
FIG. 42 illustrates a view of the mating side of the dust cap shown in FIG. 18.
Figure 43:
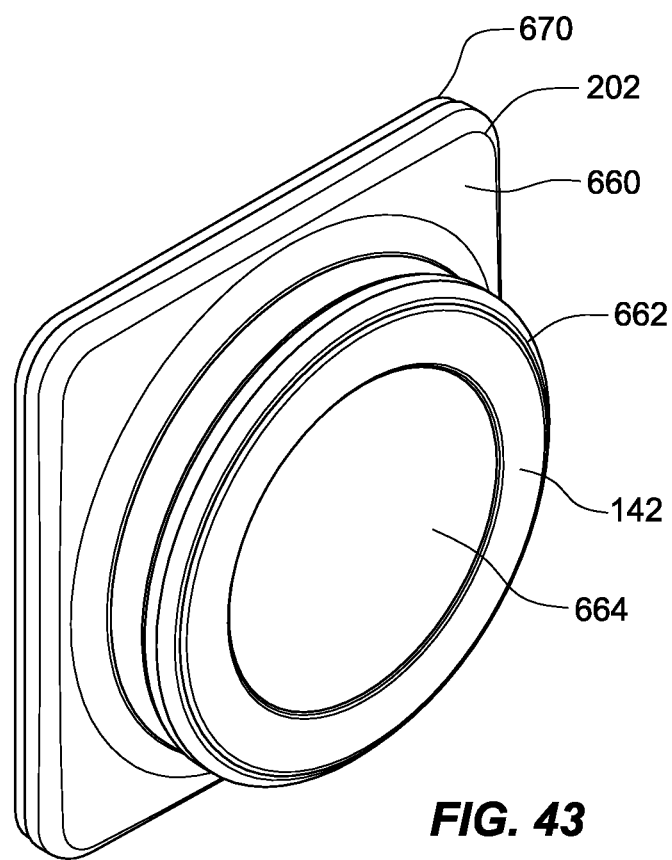
FIG. 43 illustrates a front perspective view of the quick connect holder of FIG. 18.

The back side of dust cap 622 is dimensioned to receive the mating end 134 of coupling member 632. Moreover, it is preferably dimensioned so that a portion of the dust cap extends over the sides of coupling member 632 to protect the mating end 134 thereof from unwanted dust and debris. As best seen in FIGS. 39 and 42, a piece of circular magnetic tape 680 is secured to a generally flat portion 682 of the back side of dust cap 622. Magnetic tape 680 may be secured to the generally flat portion 682 of the back side of dust cap 622 with a suitable adhesive.

With the above construction, dust cap 622 may be magnetically secured to coupling member 632 by bringing back side of dust cap 622 into proximity with the mating end 134 of coupling member 632.

In addition to the claims set forth in the claim section below, the following claims provide additional illustrative, non-limiting example of the scope of claims that may be presented with respect to various aspects of the present disclosure.

1. A magnetic quick connect for a fluid delivery system, the magnetic quick connect comprising:
   a male coupling member having a first end and a second mating end, the male coupling member having an interior wall defining a first outer fluid communication path extending within the male coupling member, the male coupling member further comprising:
      a first inner member disposed within the first outer fluid communication path, the first inner member defining a first inner communication path extending within the first outer fluid communication path, and
      a first magnetic material disposed adjacent to the second mating end; and
   a female coupling member having a first end and a second mating end, the female coupling member having an interior wall defining a second outer fluid communication path extending within the female coupling member, the female coupling member further comprising:
      a second inner member disposed within the second outer fluid communication path, the second inner member defining a second inner communication path extending within the second outer fluid communication path, and
      a second magnetic material disposed adjacent to the second mating end;
   wherein in a coupled configuration, the male and female coupling members are detachably held together by an attractive force between the first and second magnetic materials such that the first and second outer communication paths are held in fluid communication, and the first and second inner communication paths are held in fluid communication.

2. A magnetic quick connect according to claim 1, wherein at least a portion of the first inner communication path of the male coupling member extends coaxially within the first outer fluid communication path of the male coupling member.

3. A magnetic quick connect according to claim 1, wherein at least a portion of the second inner communication path of the female coupling member extends coaxially within the second outer fluid communication path of the female coupling member.

4. A magnetic quick connect according to claim 1, wherein the first inner member of the male coupling member includes a tapered protrusion, and wherein the second inner member of the female coupling member includes a tapered recess adapted to receive the tapered protrusion.

5. A magnetic quick connect according to claim 4, wherein the first inner member includes an inner O-ring disposed about the tapered protrusion, the inner O-ring forming a liquid-tight seal between the tapered protrusion and the tapered recess of the second inner member when the male and female coupling members are in the coupled configuration.

6. A magnetic quick connect according to claim 1, wherein the female coupling member further comprises an outer O-ring, the outer O-ring forming a fluid-tight seal between the male coupling member and the female coupling member when the male and female coupling members are in the coupled configuration.

7. A magnetic quick connect according to claim 6, wherein the outer O-ring is seated in an annular groove formed in a mating surface of the female magnetic coupling member.

8. A magnetic quick connect according to claim 7, wherein the annular groove is C-shaped so that the opening of the annular groove is narrower than the diameter of the O-ring.

9. A magnetic quick connect according to claim 1, wherein the female coupling member further comprises a magnet cap disposed adjacent to the second magnetic material.

10. A magnetic quick connect according to claim 9, wherein the magnet cap includes an annular groove for seating an O-ring for forming a fluid-tight seal between the male coupling member and the female coupling member when the male and female coupling members are in the coupled configuration 11. A magnetic quick connect according to claim 1, wherein the first outer and inner fluid communication paths extend coaxially with the first magnetic material, and the second outer and inner fluid communication paths extend coaxially with the second magnetic material.

12. A magnetic quick connect according to claim 1, wherein the first magnetic material is ring-shaped and extends around the first outer fluid communication path, and wherein the second magnetic material is ring-shaped and extends around the second outer fluid communication path.

13. A magnetic quick connect according to claim 1, wherein at least one of the first magnetic material and the second magnetic material comprises a permanent magnet.

14. A magnetic quick connect according to claim 1, wherein each of the first magnetic material and the second magnetic material comprises a material selected from the group consisting of a ferromagnetic material and ferrimagnetic material.

15. A magnetic quick connect according to claim 1, wherein an axial pull force that is greater than 48 ounce-force and less than 128 ounce-force between the male coupling member and female coupling member is required to decouple the male and female coupling members.

16. A magnetic quick connect according to claim 1, wherein an axial pull force that is greater than 64 ounce-force and less than 96 ounce-force between the male coupling member and female coupling member is required to decouple the male and female coupling members.

17. A magnetic quick connect according to claim 1, wherein an axial pull force that is greater than 72 ounce-force and less than 88 ounce-force between the male coupling member and female coupling member is required to decouple the male and female coupling members.

18. A magnetic quick connect according to claim 1, wherein the male coupling member further comprises a first collar disposed at the second mating end of the male coupling member, and the female coupling member further comprises a second collar disposed at the second mating end of the female coupling member.

19. A magnetic quick connect according to claim 18, wherein the first magnetic material is disposed within the first collar and the second magnetic material is disposed within the second collar.

20. A magnetic quick connect according to claim 19, wherein at least one of the first collar and second collar defines an annular channel that is open towards a mating surface of the other coupling member.

21. A magnetic quick connect according to claim 20, wherein the first magnetic material is disposed within an annular channel defined by the first collar, and the second magnetic material is disposed within an annular channel defined by the second collar.

22. A magnetic quick connect according to claim 20, wherein the first collar defines at least part of a surface of the male coupling member that abuts the female coupling member when the male and female coupling members are coupled together, and the second collar defines at least part of a surface of the female coupling member that abuts the male coupling member when the male and female coupling members are coupled together 23. A magnetic quick connect according to claim 1, wherein at least one of the male coupling member and female coupling member further comprises a clamp portion removably securable to the first end of at least one of the male coupling member and female coupling member, the clamp portion adapted to secure a fluid conduit to the at least one coupling member.

24. A magnetic quick connect according to claim 1, wherein at least one of the first inner member and second inner member further comprises a barbed hose connector adapted to secure a hose to the at least one inner member.

25. A magnetic quick connect according to claim 1, wherein at least one of the first inner member and second inner member further comprises a female connector adapted to secure a hose to the at least one inner member.

26. A magnetic quick connect for a fluid delivery system, the magnetic quick connect comprising:
a use-side coupling member having a first mating end and a first magnetic material disposed adjacent to the first mating end, the use-side coupling member having an interior wall defining a first fluid communication path extending within the use-side coupling member; and
a delivery-side coupling member having a second mating end and a second magnetic material disposed adjacent to the second mating end, the delivery-side coupling member having an interior wall defining a second fluid communication path extending within the delivery-side coupling member
wherein in a coupled configuration, the use-side and delivery-side coupling members are detachably held together by an attractive force between the first and second magnetic materials such that the first and second communication paths are held in fluid communication.

27. A magnetic quick connect according to claim 26, wherein in the coupled configuration, the use-side and delivery-side coupling members provide a substantially gas-tight communication path to communicate gas through the magnetic quick connect.

28. A magnetic quick connect according to claim 27, the communicated gas comprises air.

29. A magnetic quick connect according to claim 26, further comprising:
a removable first inner member adapted to selectively engage the interior wall of the use-side coupling member to secure the removable first inner member within the first fluid communication path of the use-side coupling member, the removable first inner member defining a first internal communication path extending within the first fluid communication path when secured within the first fluid communication path; and
a removable second inner member adapted to selectively engage the interior wall of the delivery-side coupling member to secure the removable second inner member within the second fluid communication path of the delivery-side coupling member, the removable second inner member defining a second internal communication path extending within the second fluid communication path when secured within the second fluid communication path;
wherein in the coupled configuration, the use-side and delivery-side coupling members are detachably held together by an attractive force between the first and second magnetic materials such that the first and second internal communication paths are held in fluid communication.

30. A magnetic quick connect according to claim 29, wherein in the coupled configuration, the use-side and delivery-side coupling members provide a substantially liquid-tight communication path to communicate liquid through the magnetic quick connect.

31. A magnetic quick connect according to claim 29, wherein at least a portion of the first internal communication path of the removable first inner member extends coaxially within the first fluid communication path of the use-side coupling member when the first inner member is secured within the first fluid communication path.

32. A magnetic quick connect according to claim 29, wherein at least a portion of the second internal communication path of the removable second inner member extends coaxially within the second fluid communication path of the delivery-side coupling member when the second inner member is secured within the second fluid communication path.

33. A magnetic quick connect according to claim 29, wherein the first removable inner member includes a tapered protrusion, and wherein the second removable inner member includes a tapered recess adapted to receive the tapered protrusion when the use-side and delivery-side coupling members are in the coupled configuration.

34. A magnetic quick connect according to claim 29, wherein the second removable inner member includes a tapered protrusion, and wherein the first removable inner member includes a tapered recess adapted to receive the tapered protrusion when the use-side and delivery-side coupling members are in the coupled configuration.

35. A magnetic quick connect according to claim 26 wherein the use-side coupling member is removably connectable to a headgear assembly.

36. A magnetic quick connect according to claim 26 wherein the use-side coupling member is integrally formed with a headgear assembly.

37. A splicer for introducing a second fluid path into a first fluid path in a fluid delivery system, the splicer comprising:
a splicer body defining the first fluid path;
a first connector configured to connect a first conduit to the splicer body in fluid communication with a first end of the first fluid path;
a second connector configured to connect a second conduit to the splicer body in fluid communication with a second end of the first fluid path;
a fluid inlet conduit defining a second fluid path that extends through a wall of the splicer body from an exterior port disposed outside of the splicer body to an interior port disposed within the first fluid path, the exterior port adapted to connect to a third conduit outside of the splicer body and the interior port adapted to connect to a fourth conduit within the first fluid path.

38. A splicer according to claim 37, wherein:
the first connector comprises a first adjustable fastener; and
the second connector comprises a second adjustable fastener.

39. A splicer according to claim 38, wherein the first connector and the second connector form a substantially airtight seal between the first and second conduits and the splicer body to facilitate passage of air through the splicer body.

40. A splicer according to claim 37, wherein at least one of the first connector and the second connector comprises a clamp.

41. A splicer according to claim 37, wherein the interior and exterior ports of the fluid inlet conduit are adapted to form a substantially liquid-tight seal with the third and fourth conduits to facilitate passage of a liquid through the splicer body.

42. A splicer according to claim 37, wherein at least a portion of the interior port of the fluid inlet conduit is disposed at a central region of the first fluid path.

43. A splicer according to claim 37, wherein at least a portion of the second fluid path extends coaxially with the first fluid path within the splicer body.

44. A splicer according to claim 37, wherein at least one of the interior port and the exterior port of the fluid inlet conduit includes a barbed hose connector for connecting to the third or fourth conduit.

45. A splicer according to claim 37, wherein at least one of the first connector and the second connector include helical grooves for receiving helical protrusions of the first or second conduit.

56. A splicer according to claim 37, wherein at least one of the first connector and the second connector include at least one threaded hole for receiving a fastener for securing the at least one first connector and the second connector to the splicer body.

47. A splicer according to claim 37, wherein the exterior port of the fluid inlet conduit extends in a substantially longitudinal direction parallel to a longitudinal direction of the splicer body.

48. A splicer according to claim 37, further comprising a support member extending from an interior surface of the splicer body to the interior port of the fluid inlet conduit to support the interior port in place.

49. A kit, the kit comprising:
a hose-side coupling member of a magnetic quick connect having a first fluid communication path extending from a first end to a mating end of the upstream coupling member, the mating end configured to magnetically engage with a corresponding headgear-side coupling member of the magnetic quick connect, and the first end of the hose-side coupling member is adapted to connect to an air delivery hose; and
a dust cap or a magnetic quick connect holder, or both.

50. A kit according to claim 49, further comprising a headgear-side coupling member of the magnetic quick connect, the headgear-side coupling member including a second fluid communication path extending from a first end to a mating end of the headgear-side coupling member, the mating end configured to selectively magnetically engage with the hose-side coupling member and the dust cap, and the first end of the headgear-side coupling member is adapted to engage with an input tube of a headgear interface; and wherein when the coupling members are in a coupled configuration, the first and second fluid communication paths are in fluid communication.

While exemplary embodiments and claims are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed:

1. A gas delivery system for delivering a gas into headgear adapted to be worn by a user, the gas delivery system comprising:
    headgear having an internal region configured to receive at least the nose and/or mouth of a user;
    an interface attached to the headgear and defining a first fluid communication path, the interface including a first magnetic quick connect coupling member at a first end of the first fluid communication path, and a second end of the first fluid communication path being in fluid communication with the internal region of the headgear;
    a second magnetic quick connect coupling member adapted to magnetically engage the first magnetic quick connect coupling member; and
    a conduit for communicating an airflow, the conduit and the second magnetic quick connect coupling member defining a second fluid communication path;
    a first inner member adapted to engage an interior wall of the first magnetic quick connect coupling member to secure the removable first inner member within the first fluid communication path of the first magnetic quick connect coupling member, the first inner member defining a first internal communication path extending within the first fluid communication path; and
    a second inner member adapted to engage an interior wall of the second magnetic quick connect coupling member to secure the removable second inner member within the second fluid communication path of the second magnetic quick connect coupling member, the second inner member defining a second internal communication path extending within the second fluid communication path;
    wherein in a coupled configuration, the first fluid communication path is in fluid communication with the second fluid communication path; and
    wherein in the coupled configuration, the first magnetic quick connect coupling member and the second magnetic quick connect coupling member are detachably held together by an attractive force such that the first and second internal communication paths are held in fluid communication.

2. A gas delivery system according to claim 1, wherein the first internal communication path extends coaxially with the first fluid communication path at at least one coaxial region when secured within the first fluid communication path of the first magnetic quick connect coupling member.

3. A gas delivery system according to claim 1, wherein the second internal communication path extends coaxially with the second fluid communication path at least one coaxial region when secured within the second fluid communication path of the second magnetic quick connect coupling member.

4. A gas delivery system according to claim 1, further comprising:
    a liquid conduit for communicating liquid, the liquid conduit in fluid communication with the second internal communication path.

5. A gas delivery system according to claim 1, further comprising a liquid pump in fluid communication with the liquid conduit for delivering a liquid to the second internal communication path.

* * * * *